United States Patent
Asai et al.

(10) Patent No.: US 8,796,320 B2
(45) Date of Patent: Aug. 5, 2014

(54) 1,3,4-OXADIAZOLE-2-CARBOXAMIDE COMPOUND

(75) Inventors: Akira Asai, Shizuoka (JP); Kenji Matsuno, Okayama (JP); Naohisa Ogo, Shizuoka (JP); Osamu Takahashi, Chuo-ku (JP); Yoshiaki Masuda, Chuo-ku (JP); Ayumu Muroya, Chuo-ku (JP); Yasuto Akiyama, Sunto-gun (JP); Tadashi Ashizawa, Sunto-gun (JP); Tadashi Okawara, Kumamoto (JP)

(73) Assignees: General Incorporated Association Pharma Valley Project Supporting Organization, Mishima-shi (JP); Pharma Design, Tokyo (JP); Shizuoka Prefecture, Shizuoka (JP); Kumamoto Health Science University, Kumamoto-shi (JP); Kabushiki Kaisha Yakult Honsha, Tokyo (JP)

( * ) Notice: Subject to any disclaimer, the term of this patent is extended or adjusted under 35 U.S.C. 154(b) by 0 days.

(21) Appl. No.: 13/519,707

(22) PCT Filed: Dec. 28, 2010

(86) PCT No.: PCT/JP2010/073787
§ 371 (c)(1),
(2), (4) Date: Jun. 28, 2012

(87) PCT Pub. No.: WO2011/081205
PCT Pub. Date: Jul. 7, 2011

(65) Prior Publication Data
US 2012/0302524 A1    Nov. 29, 2012

(30) Foreign Application Priority Data
Dec. 28, 2009  (JP) ............................... 2009-297960

(51) Int. Cl.
*A61K 31/4245* (2006.01)
*C07D 271/10* (2006.01)
*C07D 413/14* (2006.01)

(52) U.S. Cl.
USPC ............ 514/364; 514/378; 544/138; 548/143

(58) Field of Classification Search
None
See application file for complete search history.

(56) References Cited

U.S. PATENT DOCUMENTS

| | | | |
|---|---|---|---|
| 7,429,593 B2* | 9/2008 | Yamamori et al. ............. | 514/256 |
| 2004/0038992 A1 | 2/2004 | Bemis et al. | |
| 2007/0004701 A1* | 1/2007 | Murphy et al. ............ | 514/210.2 |
| 2009/0018145 A1 | 1/2009 | Kanne et al. | |
| 2009/0163545 A1* | 6/2009 | Goldfarb ........................ | 514/312 |
| 2010/0210661 A1 | 8/2010 | Sekiguchi et al. | |
| 2011/0172429 A1 | 7/2011 | Asai et al. | |
| 2011/0178087 A1 | 7/2011 | Kanne et al. | |

FOREIGN PATENT DOCUMENTS

| | | | |
|---|---|---|---|
| JP | 2006 513192 | 4/2006 | |
| JP | 2008 516989 | 5/2008 | |
| WO | WO 2006/022955 A2 | 3/2006 | |
| WO | WO 2006044975 A2 * | 4/2006 | ........... C07D 213/75 |
| WO | 2008 044667 | 4/2008 | |
| WO | 2009 036059 | 3/2009 | |
| WO | WO 2009/149192 A1 | 12/2009 | |
| WO | 2010 004761 | 1/2010 | |

OTHER PUBLICATIONS

Neidle Stephen, Cancer Drug Design and Discovery, ed. (Elsevier/Academic Press, 2008) pp. 427-431.*
Matsuno, K., et al, "Identification of a New Series of STAT3 Inhibitors by Virtual Screening", ACS Medicinal Chemistry Letters, vol. 1, pp. 371-375. (2010).
Ihle, J., et al., "Jaks and Stats in signaling by the cytokine receptor superfamily", TIG, vol. 11, No. 2, pp. 69-74. (Feb. 1995).
Chuan-He, Y., et al., "STAT3 complements defect in an interferon-resistant cell line: Evidence for an essential role for STAT3 in interferon signaling and biological activities", Proc. Natl. Acad. Sci. USA, vol. 95, pp. 5568-5572. (May 1998).
International Search Report issued on Mar. 22, 2011 in PCT/JP10/73787 filed on Dec. 28, 2010.
Darnell, Jr., et al., "Jak-STAT Pathways and Transcriptional Activation in Response to IFNs and Other Extracellular Signaling Proteins", Science, vol. 264, pp. 1415-1421. (Jun. 3, 1994).
Zhong, Z., et al., "Stat3 and Stat4: Members of the family of signal transducers and activators of transcription", Proc. Natl. Acad. Sci. USA., vol. 91, pp. 4806-4810. (May 1994).
Niu, G., et al., "Gene Therapy with Dominant-negative Stat3 Suppresses Growth of the Murine Melanona B16 Tumor in Vivo", Cancer Research, vol. 59, pp. 5059-5063. (Oct. 15, 1999).
Santini, G., et al., "Mobilization/Transplantation of Peripheral Blood Progenitor Cells for Aggressive Non-Hodgkin's Lymphoma with Marrow Involvement", Leukemia and Lymphoma, vol. 26, suppl. 1, pp. 83-88 (1997).

(Continued)

*Primary Examiner* — Brandon Fetterolf
*Assistant Examiner* — Ana Z Muresan
(74) *Attorney, Agent, or Firm* — Oblon, Spivak, McClelland, Maier & Neustadt, L.L.P.

(57) ABSTRACT

Provided is a 1,3,4-oxadiazole-2-carboxamide compound which has STAT3 inhibitory activity and is useful as an anti-cancer agent. Provided is a 1,3,4-oxadiazole-2-carboxamide compound represented by formula (I) or a pharmacologically acceptable salt thereof (in the formula, Ar represents a furyl group or the like; $R^1$ represents a hydrogen atom or the like; and —X—Y represents a diaryl group such as a biphenyl group).

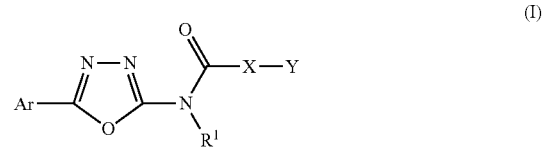

(I)

20 Claims, No Drawings

(56) References Cited

OTHER PUBLICATIONS

Yu, C-L., et al., "Constitutive Activation of the Janus Kinase-STAT Pathway in T Lymphoma Overexpressing the Lck Protein Tyrosine Kinase", The Journal of Immunology, pp. 5206-5210. (1997).
Yu, C-L., et al., "Enhanced DNA-Binding Activity of a Stat3-Related Protein in Cells Transformed by the Src Oncoprotein", Science, vol. 269, pp. 81-83. (Jul. 7, 1995).
Turkson, J., et al., "Stat 3 Activation by Src Induces Specific Gene Regulation and Is Required for Cell Transformation", Molecular and Cellular Biology, vol. 18, No. 5, pp. 2545-2552. (May 1998).
Migone, T-S., et al., "Constitutively Activated Jak-STAT Pathway in T Cells Transformed with HTLV-I", Science, vol. 269, pp. 79-81. (Jul. 7, 1995).
Rubin Grandis, J. et al., "Requirement of Stat3 but not Stat1 Activation for Epidermal Growth Factor Receptor-mediated Cell Growth In Vitro", J. Clin. Invest., vol. 102, No. 7., pp. 1385-1392 (Oct. 1998).
Schust, J., et al., "Stattic: A Small-Molecule Inhibitor of STAT3 Activation and Dimerization", Chemistry and Biology, vol. 13, pp. 1235-1242, (Nov. 2006).
Coleman, D., et al., "Investigation of the Binding Determinants of Phosphopeptides Targeted to the Src. Homology 2 Domain of the Signal Transducer and Activator of Transcription 3. Development of a High-Affinity Peptide Inhibitor", J. Med. Chem, vol. 48, pp. 6661-6670. (2005).
Database Registry[Online] Chemical Abstracts Service, Columbus, Ohio, US: May 25, 2005, XP002715070, Database Accesion No. 851094-47-8.
Database Registry[Online] Chemical Abstracts Service, Columbus, Ohio, US: Dec. 14, 2005, XP002715071, Database Accesion No. 865288-17-1.
Database Registry[Online] Chemical Abstracts Service, Columbus, Ohio, US: Jun. 20, 2006, XP002715072, Database Accesion No. 888410-10-4.
Database Registry[Online] Chemical Abstracts Service, Columbus, Ohio, US: Feb. 20, 2007, XP002715073, Database Accesion No. 922042-53-3.
Database Registry[Online] Chemical Abstracts Service, Columbus, Ohio, US: Feb. 20, 2007, XP002715080, Database Accesion No. 922069-66-7.
Database Registry[Online] Chemical Abstracts Service, Columbus, Ohio, US: Feb. 20, 2007, XP002715081, Database Accesion No. 922075-31-8.
Database Registry[Online] Chemical Abstracts Service, Columbus, Ohio, US: Nov. 11, 2007, XP002715083, Database Accesion No. 952868-27-8.
Database Registry[Online] Chemical Abstracts Service, Columbus, Ohio, US: May 29, 2008, XP002715085, Database Accesion No. 1023476-81-4.
Database Registry[Online] Chemical Abstracts Service, Columbus, Ohio, US: Sep. 14, 2008, XP002715086, Database Accesion No. 1049540-68-2.
Database Registry[Online] Chemical Abstracts Service, Columbus, Ohio, US: Sep. 14, 2008, XP002715087, Database Accesion No. 1049544-33-3.
Database Registry[Online] Chemical Abstracts Service, Columbus, Ohio, US: Sep. 14, 2008, XP002715089, Database Accesion No. 1049502-11-5.
Database Registry[Online] Chemical Abstracts Service, Columbus, Ohio, US: Oct. 8, 2008, XP002715090, Database Accesion No. 1058435-68-9.
Database Registry[Online] Chemical Abstracts Service, Columbus, Ohio, US: Feb. 13, 2009, XP002715091, Database Accesion No. 1105221-55-3.
Database Registry[Online] Chemical Abstracts Service, Columbus, Ohio, US: Feb. 13, 2009, XP002715092, Database Accesion No. 1105234-28-3.
Database Registry[Online] Chemical Abstracts Service, Columbus, Ohio, US: Jul. 29, 2009, XP002715093, Database Accesion No. 1170019-64-3.
Database Registry[Online] Chemical Abstracts Service, Columbus, Ohio, US: Jul. 31, 2009, XP002715094, Database Accesion No. 1170844-21-9.
Database Registry[Online] Chemical Abstracts Service, Columbus, Ohio, US: Aug. 2, 2009, XP002715095, Database Accesion No. 1171662-95-5.
Database Registry[Online] Chemical Abstracts Service, Columbus, Ohio, US: Aug. 3, 2009, XP002715097, Database Accesion No. 1172038-34-4.
Database Registry[Online] Chemical Abstracts Service, Columbus, Ohio, US: Aug. 3, 2009, XP002715096, Database Accesion No. 1172034-43-3.
Database Registry[Online] Chemical Abstracts Service, Columbus, Ohio, US: Aug. 3, 2009, XP002715098, Database Accesion No. 1172085-74-3.
Database Registry[Online] Chemical Abstracts Service, Columbus, Ohio, US: Aug. 3, 2009, XP002715099, Database Accesion No. 1171844-16-8.
Database Registry[Online] Chemical Abstracts Service, Columbus, Ohio, US: Aug. 4, 2009, XP002715100, Database Accesion No. 1172554-39-0.
Database Registry[Online] Chemical Abstracts Service, Columbus, Ohio, US: Aug. 4, 2009, XP002715101, Database Accesion No. 1172227-28-9.
Database Registry[Online] Chemical Abstracts Service, Columbus, Ohio, US: Aug. 4, 2009, XP002715203, Database Accesion No. 1172394-21-6.
Database Registry[Online] Chemical Abstracts Service, Columbus, Ohio, US: Aug. 5, 2009, XP002715204, Database Accesion No. 1172827-07-4.
Extended European Search Report issued on Nov. 13, 2013 for European Patent Application No. 10841060.6.

* cited by examiner

1,3,4-OXADIAZOLE-2-CARBOXAMIDE COMPOUND

TECHNICAL FIELD

The present invention relates to a novel 1,3,4-oxadiazole-2-carboxamide compound which has STAT3 inhibitory activity and is useful as an anticancer agent.

BACKGROUND ART

STAT (signal transducers and activators of transcription), a transcriptional regulator, is a DNA-binding protein whose activity is regulated by stimulations of various cytokines (IL-6, interferon, etc.) or growth factors (EGF, PDGF, etc.). Upon binding of cytokines to their receptors, JAK (Janus protein tyrosine kinase) kinase is activated to phosphorylate tyrosine in STAT (see e.g., Non Patent Documents 1 and 2). Moreover, upon binding of growth factors to their receptors, tyrosine kinase possessed by the growth factor receptors themselves phosphorylates STAT (see e.g., Non Patent Document 3). The phosphorylated STAT is activated by dimerization via its Src homology 2 (SH2) domain. The activated STAT moves into the nucleus where it specifically recognizes and binds particular DNA sequences in the gene promoter regions to induce the transcriptions of many genes. Specifically, STAT is a mediator essential for signal transduction pathways from cell surface to the nucleus and is deeply involved in cell growth or differentiation, etc.

For STAT, 6 different members (STAT1, STAT2, STAT3, STAT4, STAT5, and STAT6) and some isoforms (STAT1α, STAT1β, STAT3α, and STAT3β) are known.

Of them, STAT3, is expressed in the majority of cytomas (see e.g., Non Patent Document 4). Its constitutive activation and overexpression are observed in various cancer cells such as breast cancer, lung cancer, prostatic cancer, head and neck cancer, skin cancer, pancreatic cancer, and ovarian cancer cells, and in cancer cells such as myeloma, brain tumor, melanoma, leukemia lymphoma, and multiple myeloma cells (see e.g., Non Patent Documents 5, 6, and 7). The growth or invasion of these cancer cells is considered to depend on STAT3. Moreover, the abnormal or constitutive expression of STAT3 is also involved in cellular transformation (see e.g., Non Patent Documents 8, 9, and 10). Thus, STAT3 is probably useful as a target molecule for these cancers. Its inhibitor is therefore useful as an anticancer agent.

It has been reported that an antisense oligonucleotide complementary to the translation initiation region of STAT3 actually inhibits TGF-α-stimulated cell growth induced by an epidermal growth factor receptor (EGFR) (see e.g., Non Patent Document 11). It has also been reported that inhibition of STAT3 functions (using antisense, RNAi, peptides, or the like) can suppress the growth of cancer cells and induce apoptosis. This suggests that a STAT3 inhibitor can serve as a therapeutic or preventive drug for cancer.

For example, 6-nitrobenzo[b]thiophene-1,1-dioxide (see e.g., Non Patent Document 12) and a phosphorylated oligopeptide (see e.g., Non Patent Document 13) are known as compounds inhibiting STAT3.

A 1,3,4-oxadiazole-2-carboxamide compound represented by the following formula (A):

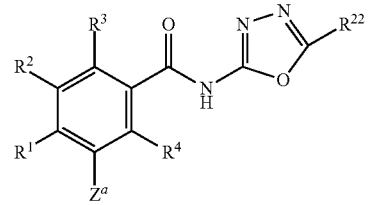

(A)

(wherein $R^1$ to $R^4$ represent a hydrogen atom, a halogen atom, or the like, $R^{22}$ represents a hydrogen atom, lower alkyl, aryl, heteroaryl, or the like, and $Z^a$ represents biaryl, or the like)
is known to be useful as a therapeutic drug for cancer (see e.g., Patent Document 1). The following compound represented by the formula (A) wherein $R^{22}$ is a phenyl group, and $Z^a$ is a biphenyl group is illustrated.

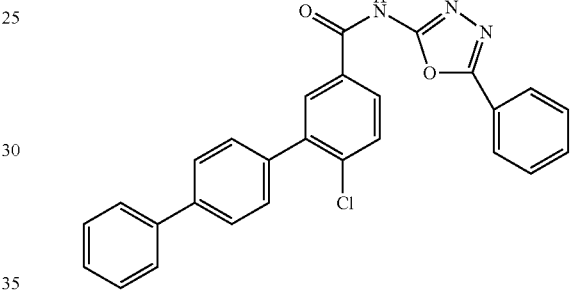

PRIOR ART DOCUMENT

Patent Document

Patent Document 1: JP-A-2008-516989

Non Patent Document

Non Patent Document 1: Trends in Genetics, 1995, 11, 69-74
Non Patent Document 2: Proc. Natl. Acad. Sci. USA, 1998, 95, 5568-5572
Non Patent Document 3: Science, 1994, 264, 1415-1421
Non Patent Document 4: Proc. Natl. Acad. Sci. USA, 1994, 91, 4806-4810
Non Patent Document 5: Cancer Res., 1999, 59, 5059-5063
Non Patent Document 6: Leuk. Lymphoma, 1997, 28, 83-88
Non Patent Document 7: J. Immunol., 1997, 159, 5206-5210
Non Patent Document 8: Science, 1995, 269, 81-83
Non Patent Document 9: Mol. Cell. Biol., 1998, 18, 2545-2552
Non Patent Document 10: Science, 1995, 269, 79-81
Non Patent Document 11: J. Clin., Invest. 1998, 102, 1385-1392
Non Patent Document 12: Chemistry & Biology, 2006, 13, 1235-1242

Non Patent Document 13: J. Med. Chem., 2005, 48, 6661-6670

SUMMARY OF INVENTION

Problems to be Solved by the Invention

An object of the present invention is to provide a novel 1,3,4-oxadiazole-2-carboxamide compound which has STAT3 inhibitory activity and is useful as an anticancer agent.

Means for Solving the Problems

As described above, the constitutive activation and overexpression of STAT3 are observed in many cancer cells, and the growth or invasion of these cancer cells is thought to depend on STAT3. Therefore, the present inventors have searched for a compound inhibiting STAT3 and consequently completed the present invention by finding that a 1,3,4-oxadiazole-2-carboxamide compound represented as a compound (I) has excellent STAT3 inhibitory activity and is useful as a medicine such as an anticancer agent.

Specifically, the present invention relates to:

(1) a 1,3,4-oxadiazole-2-carboxamide compound represented by formula (I):

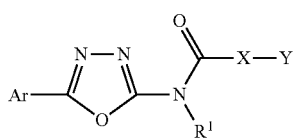

(I)

wherein
$R^1$ represents a hydrogen atom or a substituted or unsubstituted alkyl group;
Ar represents

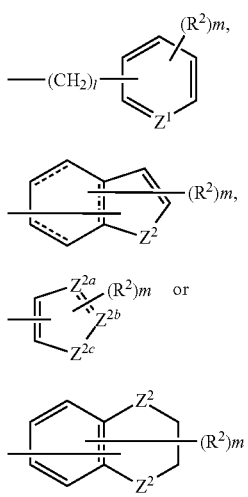

[wherein $R^2$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted alicyclic alkyl group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{11}$ (wherein $R^{11}$ represents a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted alicyclic heterocyclic alkyl group, a substituted or unsubstituted aryl group, a substituted or unsubstituted aralkyl group, a substituted or unsubstituted aromatic heterocyclic group, or a substituted or unsubstituted aromatic heterocyclic alkyl group), $COOR^{12}$ (wherein $R^{12}$ is as defined above in $R^{11}$), $C(=Q^1)NR^{13}R^{14}$ [wherein $Q^1$ represents an oxygen atom, a sulfur atom, or $NR^{15}$ (wherein $R^{15}$ is as defined above in $R^{11}$); and $R^{13}$ and $R^{14}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted alicyclic heterocyclic alkyl group, a substituted or unsubstituted aryl group, a substituted or unsubstituted aralkyl group, a substituted or unsubstituted aromatic heterocyclic group, or a substituted or unsubstituted aromatic heterocyclic alkyl group; or a group which is formed by linking $R^{13}$ and $R^{14}$ together represents a nitrogen-containing heterocyclic group], $OR^{16}$ (wherein $R^{16}$ is as defined above in $R^{11}$), $OCOR^{17}$ (wherein $R^{17}$ is as defined above in $R^{11}$), $S(O)pR^{18}$ (wherein p represents an integer of 0 to 3, and $R^{18}$ is as defined above in $R^{11}$), $SO_2NR^{19}R^{20}$ (wherein $R^{19}$ and $R^{20}$ are the same or different and are as defined above in $R^{13}$ and $R^{14}$ respectively), $NR^{21}R^{22}$ [wherein $R^{21}$ and $R^{22}$ are the same or different and each represent a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted alicyclic heterocyclic group, a substituted or unsubstituted alicyclic heterocyclic alkyl group, a substituted or unsubstituted aryl group, a substituted or unsubstituted aralkyl group, a substituted or unsubstituted aromatic heterocyclic group, a substituted or unsubstituted aromatic heterocyclic alkyl group, $COR^{23}$ (wherein $R^{23}$ is as defined above in $R^{11}$), $COOR^{24}$ (wherein $R^{24}$ is as defined above in $R^{11}$), or $SO_2R^{25}$ (wherein $R^{25}$ is as defined above in $R^{11}$); or a group which is formed by linking $R^{21}$ and $R^{22}$ together represents a nitrogen-containing heterocyclic group], $N(R^{26})C(=Q^2)NR^{27}R^{28}$ [wherein, $Q^2$, represents an oxygen atom, a sulfur atom, or $NR^{29}$ (wherein $R^{29}$ is as defined above in $R^{11}$), NCN, $CHNO_2$, or $C(CN)_2$; $R^{26}$ is as defined above in $R^{11}$; and $R^{27}$ and $R^{28}$ are the same or different and are as defined above in $R^{13}$ and $R^{14}$ respectively], $N(R^{30})SO_2NR^{31}R^{32}$ (wherein $R^{30}$ is as defined above in $R^{11}$; and $R^{31}$ and $R^{32}$ are the same or different and are as defined above in $R^{13}$ and $R^{14}$, respectively), $SiR^{33}R^{34}R^{35}$ (wherein $R^{33}$, $R^{34}$, and $R^{35}$ are the same or different and are each as defined above in $R^{11}$), a nitro group, a cyano group, a halogen atom, or a pentahalogenothio group; $Z^1$ represents —CH= or —N=; $Z^2$ represents —O— or —S—; one or two of $Z^{2a}$, $Z^{2b}$, and $Z^{2c}$, are —O—, —S—, —N($R^{1a}$)— (wherein $R^{1a}$ represents a hydrogen atom or an alkyl group), or —N=, and the rest represents —CH=; l and m are each an integer of 0 to 3; and each dashed line in formula (2) indicates that the portion may be a double bond];

X represents

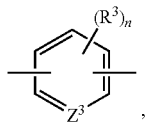
(a)

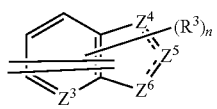
(b)

or

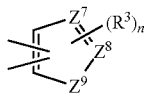
(c)

[wherein $R^3$ are the same or different and are each as defined above in $R^2$; $Z^3$, $Z^5$, $Z^7$, and $Z^8$, are the same or different and each represent —CH= or —N=; one of $Z^4$ and $Z^6$ represents —O— or —S—, and the other represents —CH= or —N=; $Z^9$ represents —O—, —S—, or —N($R^4$)— [wherein $R^4$ represents a hydrogen atom or a substituted or unsubstituted alkyl group or may form a ring together with an adjacent carbon atom through —(CH$_2$)$_r$— (wherein r represents an integer of 3 to 6)]; and n represents an integer of 0 to 2];

Y represents an aryl, aromatic heterocyclic, or dioxaborolanyl group which may have one to three substituents selected from substituted or unsubstituted alkyl groups, cycloalkyl groups, alkenyl groups, alkynyl groups, substituted or unsubstituted alicyclic heterocyclic groups, substituted or unsubstituted alicyclic heterocyclic alkyl groups, COR$^{41}$ (wherein R$^{41}$ is as defined above in R$^{11}$), COOR$^{42}$ (wherein R$^{42}$ is as defined above in R$^{11}$), C(=Q$^3$)NR$^{43}$R$^{44}$ (wherein Q$^3$ is as defined above in Q$^1$; and R$^{43}$ and R$^{44}$ are the same or different and are as defined above in R$^{13}$ and R$^{14}$, respectively), OR$^{45}$ (wherein R$^{45}$ is as defined above in R$^{11}$), OCOR$^{46}$ (wherein R$^{46}$ is as defined above in R$^{11}$), S(O)qR$^{47}$ (wherein q represents an integer of 0 to 3; and R$^{47}$ is as defined above in R$^{11}$), SO$_2$NR$^{48}$R$^{49}$ (wherein R$^{48}$ and R$^{49}$ are the same or different and are as defined above in R$^{13}$ and R$^{14}$, respectively), NR$^{50}$R$^{51}$ (wherein R$^{50}$ and R$^{51}$ are the same or different and are as defined above in R$^{21}$ and R$^{22}$, respectively), N(R$^{52}$)C(=Q$^4$)NR$^{53}$R$^{54}$ (wherein Q$^4$ is as defined above in Q$^2$; R$^{52}$ is as defined above in R$^{11}$; and R$^{53}$ and R$^{54}$ are the same or different and are as defined above in R$^{13}$ and R$^{14}$, respectively), N(R$^{55}$)SO$_2$NR$^{56}$R$^{57}$ (wherein R$^{55}$, is as defined above in R$^{11}$; and R$^{56}$ and R$^{57}$ are the same or different and are as defined above in R$^{13}$ and R$^{14}$, respectively), SiR$^{58}$R$^{59}$R$^{60}$ (wherein R$^{58}$, R$^{59}$, and R$^{60}$, are the same or different and are each as defined above in R$^{11}$), nitro groups, cyano groups, and halogen atoms; and when Ar is group (1), X is group (b), or a pharmaceutically acceptable salt thereof.

Moreover, the present invention relates to:

(2) the 1,3,4-oxadiazole-2-carboxamide compound according to (1) or a pharmaceutically acceptable salt thereof, wherein Ar is

(wherein $R^2$ and m are as defined above);

(3) the 1,3,4-oxadiazole-2-carboxamide compound according to (1) or (2) or a pharmaceutically acceptable salt thereof, wherein the compound represented by formula (I) wherein Ar represents a furyl group, $R^1$ represents a hydrogen atom, and X represents group (a) is represented by the following formula (Ia):

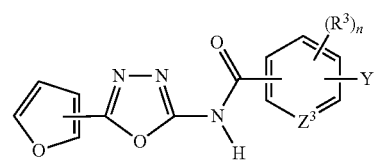
(Ia)

(wherein $R^3$, Y, $Z^3$, and n are as defined above);

(4) the 1,3,4-oxadiazole-2-carboxamide compound according to (3) or a pharmaceutically acceptable salt thereof, wherein the compound represented by formula (Ia) wherein $Z^3$ represents —CH= is represented by the following formula (Iaa):

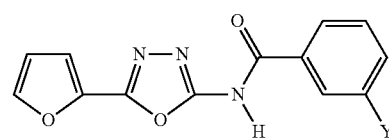
(Iaa)

(wherein Y is as defined above);

(5) the 1,3,4-oxadiazole-2-carboxamide compound according to (1) or (2) or a pharmaceutically acceptable salt thereof, wherein the compound represented by formula (I) wherein Ar represents a furyl group, $R^1$ represents a hydrogen atom, and X represents group (b) is represented by the following formula (Ib):

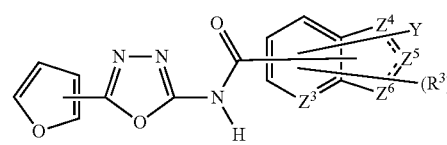
(Ib)

(wherein $R^3$, Y, $Z^3$, to $Z^6$, and n are as defined above);

(6) the 1,3,4-oxadiazole-2-carboxamide compound according to (5) or a pharmaceutically acceptable salt thereof, wherein the compound represented by formula (Ib) wherein $Z^3$ and $Z^6$ represent —N=, $Z^5$ represents —CH=, and $Z^4$ represents —S— is represented by the following formula (Iba):

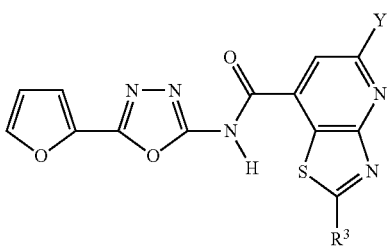

(wherein R³ and Y are as defined above);

(7) the 1,3,4-oxadiazole-2-carboxamide compound according to (1) or (2) or a pharmaceutically acceptable salt thereof, wherein the compound represented by formula (I) wherein Ar represents a furyl group, R¹ represents a hydrogen atom, and X represents group (c) is represented by the following formula (Ic):

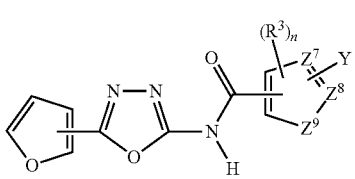

(wherein R³, Y, Z⁷, to Z⁹, and n are as defined above);

(8) the 1,3,4-oxadiazole-2-carboxamide compound according to (7) or a pharmaceutically acceptable salt thereof, wherein the compound represented by formula (Ic) wherein Z⁷ and Z⁸ represent —CH═, and Z⁹ represents —O— is represented by the following formula (Ica):

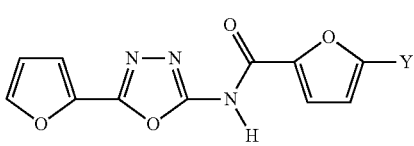

(wherein Y is as defined above); and (9) the 1,3,4-oxadiazole-2-carboxamide compound according to (7) or a pharmaceutically acceptable salt thereof, wherein the compound represented by formula (Ic) wherein Z⁷ and Z⁸ represent —CH═, and Z⁹ represents —S— is represented by the following formula (Icb):

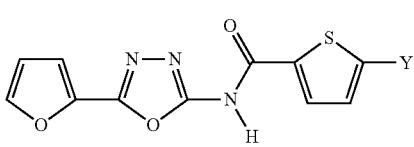

(wherein Y is as defined above).

(10) Moreover, the present invention relates to the following compounds or pharmaceutically acceptable salts thereof:
N-[5-(2-furyl)-1,3,4-oxadiazol-2-yl]-3-biphenylcarboxamide (Compound Ia-1)
N-[5-(2-furyl)-1,3,4-oxadiazol-2-yl]-2'-hydroxy-3-biphenylcarboxamide (Compound Ia-2)
2'-formyl-N-[5-(2-furyl)-1,3,4-oxadiazol-2-yl]-3-biphenylcarboxamide (Compound Ia-3)
N-[5-(2-furyl)-1,3,4-oxadiazol-2-yl]-3'-hydroxy-3-biphenylcarboxamide (Compound Ia-4)
N-[5-(2-furyl)-1,3,4-oxadiazol-2-yl]-3'-nitro-3-biphenylcarboxamide (Compound Ia-5)
3'-formyl-N-[5-(2-furyl)-1,3,4-oxadiazol-2-yl]-3-biphenylcarboxamide (Compound Ia-6)
N-[5-(2-furyl)-1,3,4-oxadiazol-2-yl]-3'-methoxycarbonyl-3-biphenylcarboxamide (Compound Ia-7)
3'-carboxy-N-[5-(2-furyl)-1,3,4-oxadiazol-2-yl]-3-biphenylcarboxamide (Compound Ia-8)
3'-cyano-N-[5-(2-furyl)-1,3,4-oxadiazol-2-yl]-3-biphenylcarboxamide (Compound Ia-9)
4'-fluoro-N-[5-(2-furyl)-1,3,4-oxadiazol-2-yl]-3-biphenylcarboxamide (Compound Ia-10)
4'-chloro-N-[5-(2-furyl)-1,3,4-oxadiazol-2-yl]-3-biphenylcarboxamide (Compound Ia-11)
N-[5-(2-furyl)-1,3,4-oxadiazol-2-yl]-4'-methyl-3-biphenylcarboxamide (Compound Ia-12)
N-[5-(2-furyl)-1,3,4-oxadiazol-2-yl]-4'-vinyl-3-biphenylcarboxamide (Compound Ia-13)
4'-tert-butyl-N-[5-(2-furyl)-1,3,4-oxadiazol-2-yl]-3-biphenylcarboxamide (Compound Ia-14)
N-[5-(2-furyl)-1,3,4-oxadiazol-2-yl]-4'-hydroxy-3-biphenylcarboxamide (Compound Ia-15)
N-[5-(2-furyl)-1,3,4-oxadiazol-2-yl]-4'-methoxy-3-biphenylcarboxamide (Compound Ia-16)
4'-formyl-N-[5-(2-furyl)-1,3,4-oxadiazol-2-yl]-3-biphenylcarboxamide (Compound Ia-17)
4'-acetyl-N-[5-(2-furyl)-1,3,4-oxadiazol-2-yl]-3-biphenylcarboxamide (Compound Ia-18)
4'-benzoyl-N-[5-(2-furyl)-1,3,4-oxadiazol-2-yl]-3-biphenylcarboxamide (Compound Ia-19)
4'-carbamoyl-N-[5-(2-furyl)-1,3,4-oxadiazol-2-yl]-3-biphenylcarboxamide (Compound Ia-20)
4'-cyano-N-[5-(2-furyl)-1,3,4-oxadiazol-2-yl]-3-biphenylcarboxamide (Compound Ia-21)
4'-cyanomethyl-N-[5-(2-furyl)-1,3,4-oxadiazol-2-yl]-3-biphenylcarboxamide (Compound Ia-22)
4'-n-butoxycarbonyl-N-[5-(2-furyl)-1,3,4-oxadiazol-2-yl]-3-biphenylcarboxamide (Compound Ia-23)
N-[5-(2-furyl)-1,3,4-oxadiazol-2-yl]-4'-nitro-3-biphenylcarboxamide (Compound Ia-24)
N-[5-(2-furyl)-1,3,4-oxadiazol-2-yl]-4'-sulfamoyl-3-biphenylcarboxamide (Compound Ia-25)
N-[5-(2-furyl)-1,3,4-oxadiazol-2-yl]-4'-(N-methylsulfamoyl)-3-biphenylcarboxamide (Compound Ia-26)
N-[5-(2-furyl)-1,3,4-oxadiazol-2-yl]-4'-(N,N-dimethylsulfamoyl)-3-biphenylcarboxamide (Compound Ia-27)
N-[5-(2-furyl)-1,3,4-oxadiazol-2-yl]-4'-methanesulfonyl-3-biphenylcarboxamide (Compound Ia-28)
4'-cyano-N-[5-(2-furyl)-1,3,4-oxadiazol-2-yl]-2'-methyl-3-biphenylcarboxamide (Compound Ia-29)
4'-acetyl-3'-fluoro-N-[5-(2-furyl)-1,3,4-oxadiazol-2-yl]-3-biphenylcarboxamide (Compound Ia-30)
N-[5-(2-furyl)-1,3,4-oxadiazol-2-yl]-4'-sulfamoyl-4-biphenylcarboxamide (Compound Ia-31)
N-[5-(2-furyl)-1,3,4-oxadiazol-2-yl]-3-(1-naphthyl)benzenecarboxamide (Compound Ia-32)
N-[5-(2-furyl)-1,3,4-oxadiazol-2-yl]-3-(2-naphthyl)benzenecarboxamide (Compound Ia-33)
N-[5-(2-furyl)-1,3,4-oxadiazol-2-yl]-3-(5-methyl-2-furyl)benzenecarboxamide (Compound Ia-34)
3-(2-cyano-5-pyridyl)-N-[5-(2-furyl)-1,3,4-oxadiazol-2-yl]benzenecarboxamide (Compound Ia-35)

N-[5-(2-furyl)-1,3,4-oxadiazol-2-yl]-3-(5-sulfamoyl-2-thienyl)benzenecarboxamide (Compound Ia-36)
N-[5-(2-furyl)-1,3,4-oxadiazol-2-yl]-3-(3-pyridyl)benzenecarboxamide trifluoroacetate (Compound Ia-37)
N-[5-(2-furyl)-1,3,4-oxadiazol-2-yl]-3-(2-hydroxy-5-pyridyl)benzenecarboxamide (Compound Ia-38)
3-(2-amino-5-pyridyl)-N-[5-(2-furyl)-1,3,4-oxadiazol-2-yl]benzenecarboxamide (Compound Ia-39)
N-[5-(2-furyl)-1,3,4-oxadiazol-2-yl]-3-(2-methylthio-5-pyridyl)benzenecarboxamide (Compound Ia-40)
N-[5-(2-furyl)-1,3,4-oxadiazol-2-yl]-3-(4-pyridyl)benzenecarboxamide (Compound Ia-41)
N-[5-(2-furyl)-1,3,4-oxadiazol-2-yl]-3-(3,4-methylenedioxyphenyl)benzenecarboxamide (Compound Ia-42)
N-[5-(2-furyl)-1,3,4-oxadiazol-2-yl]-3-(1-methyl-6-indolyl)benzenecarboxamide (Compound Ia-43)
N-[5-(2-furyl)-1,3,4-oxadiazol-2-yl]-3-(1-methyl-5-indolinyl)benzenecarboxamide (Compound Ia-44)
N-[5-(2-furyl)-1,3,4-oxadiazol-2-yl]-3-(1-methyl-5-indazolyl)benzenecarboxamide (Compound Ia-45)
N-[5-(2-furyl)-1,3,4-oxadiazol-2-yl]-3-(1-methyl-6-benzimidazolyl)benzenecarboxamide (Compound Ia-46)
3-(5-benzothienyl)-N-[5-(2-furyl)-1,3,4-oxadiazol-2-yl]benzenecarboxamide (Compound Ia-47)
3-(5-benzothiazolyl)-N-[5-(2-furyl)-1,3,4-oxadiazol-2-yl]benzenecarboxamide (Compound Ia-48)
N-[5-(2-furyl)-1,3,4-oxadiazol-2-yl]-3-[9-methyl-3-(9H-carbazolyl)]benzenecarboxamide (Compound Ia-49)
N-[5-(2-furyl)-1,3,4-oxadiazol-2-yl]-3-(1-methyl-5-indolyl)benzenecarboxamide (Compound Ia-50)
2-fluoro-N-[5-(2-furyl)-1,3,4-oxadiazol-2-yl]-3-(1-methyl-5-indolyl)benzenecarboxamide (Compound Ia-51)
5-fluoro-N-[5-(2-furyl)-1,3,4-oxadiazol-2-yl]-3-(1-methyl-5-indolyl)benzenecarboxamide (Compound Ia-52)
2-fluoro-N-[5-(2-furyl)-1,3,4-oxadiazol-2-yl]-5-(1-methyl-5-indolyl)benzenecarboxamide (Compound Ia-53)
N-[5-(2-furyl)-1,3,4-oxadiazol-2-yl]-2-phenyl-4-pyridinecarboxamide (Compound Ia-54)
N-[5-(2-furyl)-1,3,4-oxadiazol-2-yl]-2,6-diphenyl-4-pyridinecarboxamide (Compound Ia-55)
2-(4-bromophenyl)-6-(4-chlorophenyl)-N-[5-(2-furyl)-1,3,4-oxadiazol-2-yl]-4-pyridinecarboxamide (Compound Ia-56)
N-[5-(2-furyl)-1,3,4-oxadiazol-2-yl]-2-phenyl-5-pyridinecarboxamide (Compound Ia-57)
N-[5-(2-furyl)-1,3,4-oxadiazol-2-yl]-5-(1-methyl-5-indolyl)-3-pyridinecarboxamide (Compound Ia-58)
4'-cyano-3'-fluoro-N-[5-(2-furyl)-1,3,4-oxadiazol-2-yl]-3-biphenylcarboxamide (Compound Ia-59)
4'-(2-cyano-2-propyl)-N-[5-(2-furyl)-1,3,4-oxadiazol-2-yl]-3-biphenylcarboxamide (Compound Ia-60)
4'-tert-butyl-N-[5-(2-furyl)-1,3,4-oxadiazol-2-yl]-3'-nitro-3-biphenylcarboxamide (Compound Ia-61)
N-[5-(2-furyl)-1,3,4-oxadiazol-2-yl]-4'-trimethylsilyl-3-biphenylcarboxamide (Compound Ia-62)
N-[5-(2-furyl)-1,3,4-oxadiazol-2-yl]-4'-trifluoromethyl-3-biphenylcarboxamide (Compound Ia-63)
N-[5-(2-furyl)-1,3,4-oxadiazol-2-yl]-4'-trifluoromethoxy-3-biphenylcarboxamide (Compound Ia-64)
4'-benzyl-N-[5-(2-furyl)-1,3,4-oxadiazol-2-yl]-3-biphenylcarboxamide (Compound Ia-65)
N-[5-(2-furyl)-1,3,4-oxadiazol-2-yl]-4'-phenoxy-3-biphenylcarboxamide (Compound Ia-66)
4'-diphenylamino-N-[5-(2-furyl)-1,3,4-oxadiazol-2-yl]-3-biphenylcarboxamide (Compound Ia-67)
N-[5-(2-furyl)-1,3,4-oxadiazol-2-yl]-4'-ureido-3-biphenylcarboxamide (Compound Ia-68)
N-[5-(2-furyl)-1,3,4-oxadiazol-2-yl]-4'-methoxycarbonyl-3-biphenylcarboxamide (Compound Ia-69)
N-[5-(2-furyl)-1,3,4-oxadiazol-2-yl]-4'-propionyl-3-biphenylcarboxamide (Compound Ia-70)
N-[5-(2-furyl)-1,3,4-oxadiazol-2-yl]-4'-piperidinosulfonyl-3-biphenylcarboxamide (Compound Ia-71)
N-[5-(2-furyl)-1,3,4-oxadiazol-2-yl]-4'-sulfo-3-biphenylcarboxamide (Compound Ia-72)
N-[5-(2-furyl)-1,3,4-oxadiazol-2-yl]-3-(o-terphenyl)carboxamide (Compound Ia-73)
N-[5-(2-furyl)-1,3,4-oxadiazol-2-yl]-3-(m-terphenyl)carboxamide (Compound Ia-74)
N-[5-(2-furyl)-1,3,4-oxadiazol-2-yl]-3-(p-terphenyl)carboxamide (Compound Ia-75)
3'-fluoro-N-[5-(2-furyl)-1,3,4-oxadiazol-2-yl]-3-(p-terphenyl)carboxamide (Compound Ia-76)
4''-chloro-N-[5-(2-furyl)-1,3,4-oxadiazol-2-yl]-3-(p-terphenyl)carboxamide (Compound Ia-77)
4''-ethyl-N-[5-(2-furyl)-1,3,4-oxadiazol-2-yl]-3-(p-terphenyl)carboxamide (Compound Ia-78)
4''-ethoxy-N-[5-(2-furyl)-1,3,4-oxadiazol-2-yl]-3-(p-terphenyl)carboxamide (Compound Ia-79)
N-[5-(2-furyl)-1,3,4-oxadiazol-2-yl]-4''-propoxy-3-(p-terphenyl)carboxamide (Compound Ia-80)
N-[5-(2-furyl)-1,3,4-oxadiazol-2-yl]-4''-isopropoxy-3-(p-terphenyl)carboxamide (Compound Ia-81)
N-[5-(2-furyl)-1,3,4-oxadiazol-2-yl]-4'-(1-naphthyl)-3-biphenylcarboxamide (Compound Ia-82)
N-[5-(2-furyl)-1,3,4-oxadiazol-2-yl]-4'-(2-naphthyl)-3-biphenylcarboxamide (Compound Ia-83)
4'-cyclohexyl-N-[5-(2-furyl)-1,3,4-oxadiazol-2-yl]-3-biphenylcarboxamide (Compound Ia-84)
N-[5-(2-furyl)-1,3,4-oxadiazol-2-yl]-4'-(trans-4-n-propylcyclohexyl)-3-biphenylcarboxamide (Compound Ia-85)
N-[5-(2-furyl)-1,3,4-oxadiazol-2-yl]-3'-morpholino-3-biphenylcarboxamide (Compound Ia-86)
N-[5-(2-furyl)-1,3,4-oxadiazol-2-yl]-4'-morpholino-3-biphenylcarboxamide (Compound Ia-87)
4'-(4-tert-butoxycarbonyl-1-piperazinyl)-N-[5-(2-furyl)-1,3,4-oxadiazol-2-yl]-3-biphenylcarboxamide (Compound Ia-88)
N-[5-(2-furyl)-1,3,4-oxadiazol-2-yl]-4'-(1-piperazinyl)-3-biphenylcarboxamide (Compound Ia-89)
N-[5-(2-furyl)-1,3,4-oxadiazol-2-yl]-4'-(2-morpholinoethyl)-3-biphenylcarboxamide (Compound Ia-90)
N-[5-(2-furyl)-1,3,4-oxadiazol-2-yl]-3-(2-pyridyl)benzenecarboxamide (Compound Ia-91)
3-(2-cyano-5-pyridyl)-N-[5-(2-furyl)-1,3,4-oxadiazol-2-yl]benzenecarboxamide (Compound Ia-92)
N-[5-(2-furyl)-1,3,4-oxadiazol-2-yl]-3-(2-trifluoromethyl-5-pyridyl)benzenecarboxamide (Compound Ia-93)
N-[5-(2-furyl)-1,3,4-oxadiazol-2-yl]-3-(2-morpholino-3-pyridyl)benzenecarboxamide (Compound Ia-94)
N-[5-(2-furyl)-1,3,4-oxadiazol-2-yl]-3-(2-morpholino-4-pyridyl)benzenecarboxamide (Compound Ia-95)
N-[5-(2-furyl)-1,3,4-oxadiazol-2-yl]-3-[2-(1-piperazinyl)-5-pyridyl]benzenecarboxamide (Compound Ia-96)
N-[5-(2-furyl)-1,3,4-oxadiazol-2-yl]-3-(5-phenyl-2-thienyl)benzenecarboxamide (Compound Ia-97)
N-[5-(2-furyl)-1,3,4-oxadiazol-2-yl]-3-(2-morpholino-5-pyrimidinyl)benzenecarboxamide (Compound Ia-98)
N-[5-(2-furyl)-1,3,4-oxadiazol-2-yl]-3-(3-quinolyl)benzenecarboxamide (Compound Ia-99)
N-[5-(2-furyl)-1,3,4-oxadiazol-2-yl]-3-(6-quinoxalinyl)benzenecarboxamide (Compound Ia-100)
3-(5-benzofurazanyl)-N-[5-(2-furyl)-1,3,4-oxadiazol-2-yl]benzenecarboxamide (Compound Ia-101)

3-(3,4-ethylenedioxyphenyl)-N-[5-(2-furyl)-1,3,4-oxadiazol-2-yl]benzenecarboxamide (Compound Ia-102)
N-[5-(2-furyl)-1,3,4-oxadiazol-2-yl]-3-(4-methyl-1-naphthyl)benzenecarboxamide (Compound Ia-103)
3-(2-ethoxy-1-naphthyl)-N-[5-(2-furyl)-1,3,4-oxadiazol-2-yl]benzenecarboxamide (Compound Ia-104)
3-(4-fluoro-1-naphthyl)-N-[5-(2-furyl)-1,3,4-oxadiazol-2-yl]benzenecarboxamide (Compound Ia-105)
N-[5-(2-furyl)-1,3,4-oxadiazol-2-yl]-3-(3-methoxy-2-naphthyl)benzenecarboxamide (Compound Ia-106)
N-[5-(2-furyl)-1,3,4-oxadiazol-2-yl]-3-(6-methoxy-2-naphthyl)benzenecarboxamide (Compound Ia-107)
3-(6-ethoxy-2-naphthyl)-N-[5-(2-furyl)-1,3,4-oxadiazol-2-yl]benzenecarboxamide (Compound Ia-108)
3-(6-benzyloxy-2-naphthyl)-N-[5-(2-furyl)-1,3,4-oxadiazol-2-yl]benzenecarboxamide (Compound Ia-109)
3-(9-anthryl)-N-[5-(2-furyl)-1,3,4-oxadiazol-2-yl]benzenecarboxamide (Compound Ia-110)
3-(5-acenaphthenyl)-N-[5-(2-furyl)-1,3,4-oxadiazol-2-yl]benzenecarboxamide (Compound Ia-111)
N-[5-(2-furyl)-1,3,4-oxadiazol-2-yl]-3-(4,4,5,5-tetramethyl-1,3,2-dioxaborolane-2-yl)benzenecarboxamide (Compound Ia-112)
4"-ethyl-2-fluoro-N-[5-(2-furyl)-1,3,4-oxadiazol-2-yl]-3-(p-terphenyl)carboxamide (Compound Ia-113)
4"-ethyl-4-fluoro-N-[5-(2-furyl)-1,3,4-oxadiazol-2-yl]-3-(p-terphenyl)carboxamide (Compound Ia-114)
4"-ethyl-N-[5-(2-furyl)-1,3,4-oxadiazol-2-yl]-4-methyl-3-(p-terphenyl)carboxamide (Compound Ia-115)
4"-ethyl-5-fluoro-N-[5-(2-furyl)-1,3,4-oxadiazol-2-yl]-3-(p-terphenyl)carboxamide (Compound Ia-116)
6-(4-biphenylyl)-N-[5-(2-furyl)-1,3,4-oxadiazol-2-yl]-2-pyridinecarboxamide (Compound Ia-117)
6-(4'-ethyl-4-biphenylyl)-N-[5-(2-furyl)-1,3,4-oxadiazol-2-yl]-2-pyridinecarboxamide (Compound Ia-118)
5-(4-biphenylyl)-N-[5-(2-furyl)-1,3,4-oxadiazol-2-yl]-3-pyridinecarboxamide (Compound Ia-119)
5-(4'-ethyl-4-biphenylyl)-N-[5-(2-furyl)-1,3,4-oxadiazol-2-yl]-3-pyridinecarboxamide (Compound Ia-120)
4'-bromo-N-[5-(2-furyl)-1,3,4-oxadiazol-2-yl]-3-biphenylcarboxamide (Compound Ia-121)
2"-fluoro-N-[5-(2-furyl)-1,3,4-oxadiazol-2-yl]-3-(p-terphenyl)carboxamide (Compound Ia-122)
2"-chloro-N-[5-(2-furyl)-1,3,4-oxadiazol-2-yl]-3-(p-terphenyl)carboxamide (Compound Ia-123)
N-[5-(2-furyl)-1,3,4-oxadiazol-2-yl]-2"-methyl-3-(p-terphenyl)carboxamide (Compound Ia-124)
N-[5-(2-furyl)-1,3,4-oxadiazol-2-yl]-2"-methoxy-3-(p-terphenyl)carboxamide (Compound Ia-125)
N-[5-(2-furyl)-1,3,4-oxadiazol-2-yl]-2"-trifluoromethyl-3-(p-terphenyl)carboxamide (Compound Ia-126)
N-[5-(2-furyl)-1,3,4-oxadiazol-2-yl]-2"-trifluoromethoxy-3-(p-terphenyl)carboxamide (Compound Ia-127)
2"-cyano-N-[5-(2-furyl)-1,3,4-oxadiazol-2-yl]-3-(p-terphenyl)carboxamide (Compound Ia-128)
N-[5-(2-furyl)-1,3,4-oxadiazol-2-yl]-3-(1,1':4',1":2",1'''-quaterphenyl)carboxamide (Compound Ia-129)
3"-fluoro-N-[5-(2-furyl)-1,3,4-oxadiazol-2-yl]-3-(p-terphenyl)carboxamide (Compound Ia-130)
3"-chloro-N-[5-(2-furyl)-1,3,4-oxadiazol-2-yl]-3-(p-terphenyl)carboxamide (Compound Ia-131)
N-[5-(2-furyl)-1,3,4-oxadiazol-2-yl]-3"-methyl-3-(p-terphenyl)carboxamide (Compound Ia-132)
N-[5-(2-furyl)-1,3,4-oxadiazol-2-yl]-3"-methoxy-3-(p-terphenyl)carboxamide (Compound Ia-133)
N-[5-(2-furyl)-1,3,4-oxadiazol-2-yl]-3"-trifluoromethyl-3-(p-terphenyl)carboxamide (Compound Ia-134)
N-[5-(2-furyl)-1,3,4-oxadiazol-2-yl]-3"-trifluoromethoxy-3-(p-terphenyl)carboxamide (Compound Ia-135)
3"-cyano-N-[5-(2-furyl)-1,3,4-oxadiazol-2-yl]-3-(p-terphenyl)carboxamide (Compound Ia-136)
N-[5-(2-furyl)-1,3,4-oxadiazol-2-yl]-3-(1,1':4',1":3",1'''-quaterphenyl)carboxamide (Compound Ia-137)
4"-fluoro-N-[5-(2-furyl)-1,3,4-oxadiazol-2-yl]-3-(p-terphenyl)carboxamide (Compound Ia-138)
N-[5-(2-furyl)-1,3,4-oxadiazol-2-yl]-4"-methyl-3-(p-terphenyl)carboxamide (Compound Ia-139)
N-[5-(2-furyl)-1,3,4-oxadiazol-2-yl]-4"-methoxy-3-(p-terphenyl)carboxamide (Compound Ia-140)
N-[5-(2-furyl)-1,3,4-oxadiazol-2-yl]-4"-trifluoromethyl-3-(p-terphenyl)carboxamide (Compound Ia-141)
N-[5-(2-furyl)-1,3,4-oxadiazol-2-yl]-4"-trifluoromethoxy-3-(p-terphenyl)carboxamide (Compound Ia-142)
4"-cyano-N-[5-(2-furyl)-1,3,4-oxadiazol-2-yl]-3-(p-terphenyl)carboxamide (Compound Ia-143)
N-[5-(2-furyl)-1,3,4-oxadiazol-2-yl]-3-(1,1':4',1":4",1'''-quaterphenyl)carboxamide (Compound Ia-144)
N-[5-(2-furyl)-1,3,4-oxadiazol-2-yl]-4"-trimethylsilyl-3-(p-terphenyl)carboxamide (Compound Ia-145)
4'-(1-cyclohexenyl)-N-[5-(2-furyl)-1,3,4-oxadiazol-2-yl]-3-biphenylcarboxamide (Compound Ia-146)
4'-(4,4-dimethyl-1-cyclohexenyl)-N-[5-(2-furyl)-1,3,4-oxadiazol-2-yl]-3-biphenylcarboxamide (Compound Ia-147)
4'-(4-tert-butyl-1-cyclohexenyl)-N-[5-(2-furyl)-1,3,4-oxadiazol-2-yl]-3-biphenylcarboxamide (Compound Ia-148)
N-[5-(2-furyl)-1,3,4-oxadiazol-2-yl]-4'-(2,2,6,6-tetramethyl-3,6-dihydro-4-pyranyl)-3-biphenylcarboxamide (Compound Ia-149)
N-[5-(2-furyl)-1,3,4-oxadiazol-2-yl]-4'-(1-methyl-1,2,3,6-tetrahydro-4-pyridyl)-3-biphenylcarboxamide (Compound Ia-150)
4'-(2-furyl)-N-[5-(2-furyl)-1,3,4-oxadiazol-2-yl]-3-biphenylcarboxamide (Compound Ia-151)
N-[5-(2-furyl)-1,3,4-oxadiazol-2-yl]-4'-(2-thienyl)-3-biphenylcarboxamide (Compound Ia-152)
N-[5-(2-furyl)-1,3,4-oxadiazol-2-yl]-4'-(3-thienyl)-3-biphenylcarboxamide (Compound Ia-153)
N-[5-(2-furyl)-1,3,4-oxadiazol-2-yl]-4'-(1-methyl-4-pyrazolyl)-3-biphenylcarboxamide (Compound Ia-154)
N-[5-(2-furyl)-1,3,4-oxadiazol-2-yl]-4'-(4-pyridyl)-3-biphenylcarboxamide (Compound Ia-155)
N-[5-(2-furyl)-1,3,4-oxadiazol-2-yl]-4'-(1-methyl-5-indolyl)-3-biphenylcarboxamide (Compound Ia-156)
N-[5-(2-furyl)-1,3,4-oxadiazol-2-yl]-3"-hydroxy-3-(p-terphenyl)carboxamide (Compound Ia-157)
N-[5-(2-furyl)-1,3,4-oxadiazol-2-yl]-4"-(1-propyl)-3-(p-terphenyl)carboxamide (Compound Ia-158)
N-[5-(2-furyl)-1,3,4-oxadiazol-2-yl]-4"-isopropyl-3-(p-terphenyl)carboxamide (Compound Ia-159)
4"-(1-butyl)-N-[5-(2-furyl)-1,3,4-oxadiazol-2-yl]-3-(p-terphenyl)carboxamide (Compound Ia-160)
4"-tert-butyl-N-[5-(2-furyl)-1,3,4-oxadiazol-2-yl]-3-(p-terphenyl)carboxamide (Compound Ia-161)
N-[5-(2-furyl)-1,3,4-oxadiazol-2-yl]-4"-hydroxy-3-(p-terphenyl)carboxamide (Compound Ia-162)
4"-(N,N-dimethylamino)-N-[5-(2-furyl)-1,3,4-oxadiazol-2-yl]-3-(p-terphenyl)carboxamide (Compound Ia-163)
N-[5-(2-furyl)-1,3,4-oxadiazol-2-yl]-4"-methanesulfonyl-3-(p-terphenyl)carboxamide (Compound Ia-164)
N-[5-(2-furyl)-1,3,4-oxadiazol-2-yl]-4"-sulfamoyl-3-(p-terphenyl)carboxamide (Compound Ia-165)
5-chloro-4"-ethyl-N-[5-(2-furyl)-1,3,4-oxadiazol-2-yl]-3-(p-terphenyl)carboxamide (Compound Ia-166)

4"-ethyl-N-[5-(2-furyl)-1,3,4-oxadiazol-2-yl]-5-nitro-3-(p-terphenyl)carboxamide (Compound Ia-167)

5-acetylamino-4"-ethyl-N-[5-(2-furyl)-1,3,4-oxadiazol-2-yl]-3-(p-terphenyl)carboxamide (Compound Ia-168)

4"-ethyl-N-[5-(2-furyl)-1,3,4-oxadiazol-2-yl]-5-trifluoromethyl-3-(p-terphenyl)carboxamide (Compound Ia-169)

4"-ethyl-N-[5-(2-furyl)-1,3,4-oxadiazol-2-yl]-5-trifluoromethoxy-3-(p-terphenyl)carboxamide (Compound Ia-170)

5-cyano-4"-ethyl-N-[5-(2-furyl)-1,3,4-oxadiazol-2-yl]-3-(p-terphenyl)carboxamide (Compound Ia-171)

4"-ethyl-N-[5-(2-furyl)-1,3,4-oxadiazol-2-yl]-5-pentafluorothio-3-(p-terphenyl)carboxamide (Compound Ia-172)

N-[5-(2-furyl)-1,3,4-oxadiazol-2-yl]-5-phenyl-2-piperidino-7-thiazolo[4,5-b]pyridinecarboxamide (Compound Ib-1)

5-(3-chlorophenyl)-N-[5-(2-furyl)-1,3,4-oxadiazol-2-yl]-2-piperidino-7-thiazolo[4,5-b]pyridinecarboxamide (Compound Ib-2)

N-[5-(2-furyl)-1,3,4-oxadiazol-2-yl]-5-(4-methylphenyl)-2-piperidino-7-thiazolo[4,5-b]pyridinecarboxamide (Compound Ib-3)

N-[5-(2-furyl)-1,3,4-oxadiazol-2-yl]-5-(3,4-dimethoxyphenyl)-2-piperidino-7-thiazolo[4,5-b]pyridinecarboxamide (Compound Ib-4)

N-[5-(2-furyl)-1,3,4-oxadiazol-2-yl]-3-methyl-6-phenyl-4-benzo[d]isoxazolecarboxamide (Compound Ib-5)

N-[5-(2-furyl)-1,3,4-oxadiazol-2-yl]-5-(2-naphthyl)-2-piperidino-7-thiazolo[4,5-b]pyridinecarboxamide (Compound Ib-6)

N-[5-(2-furyl)-1,3,4-oxadiazol-2-yl]-2-(4-methylpiperidino)-5-phenyl-7-thiazolo[4,5-b]pyridinecarboxamide (Compound Ib-7)

5-phenyl-N-(5-phenyl-1,3,4-oxadiazol-2-yl)-2-piperidino-7-thiazolo[4,5-b]pyridinecarboxamide (Compound Ib-8)

N-[5-(2-chlorophenyl)-1,3,4-oxadiazol-2-yl]-5-phenyl-2-piperidino-7-thiazolo[4,5-b]pyridinecarboxamide (Compound Ib-9)

N-[5-(4-chlorophenyl)-1,3,4-oxadiazol-2-yl]-5-phenyl-2-piperidino-7-thiazolo[4,5-b]pyridinecarboxamide (Compound Ib-10)

N-[5-(4-methoxyphenyl)-1,3,4-oxadiazol-2-yl]-5-phenyl-2-piperidino-7-thiazolo[4,5-b]pyridinecarboxamide (Compound Ib-11)

N-[5-(4-nitrophenyl)-1,3,4-oxadiazol-2-yl]-5-phenyl-2-piperidino-7-thiazolo[4,5-b]pyridinecarboxamide (Compound Ib-12)

N-(5-benzyl-1,3,4-oxadiazol-2-yl)-5-phenyl-2-piperidino-7-thiazolo[4,5-b]pyridinecarboxamide (Compound Ib-13)

N-[5-(2-methyl-3-furyl)-1,3,4-oxadiazol-2-yl]-5-phenyl-2-piperidino-7-thiazolo[4,5-b]pyridinecarboxamide (Compound Ib-14)

N-[5-(2,5-dimethyl-3-furyl)-1,3,4-oxadiazol-2-yl]-5-phenyl-2-piperidino-7-thiazolo[4,5-b]pyridinecarboxamide (Compound Ib-15)

5-phenyl-2-piperidino-N-[5-(2-thienyl)-1,3,4-oxadiazol-2-yl]-7-thiazolo[4,5-b]pyridinecarboxamide (Compound Ib-16)

N-[5-(3-methyl-2-thienyl)-1,3,4-oxadiazol-2-yl]-5-phenyl-2-piperidino-7-thiazolo[4,5-b]pyridinecarboxamide (Compound Ib-17)

N-[5-(5-methyl-2-thienyl)-1,3,4-oxadiazol-2-yl]-5-phenyl-2-piperidino-7-thiazolo[4,5-b]pyridinecarboxamide (Compound Ib-18)

5-phenyl-2-piperidino-N-[5-(3-thienyl)-1,3,4-oxadiazol-2-yl]-7-thiazolo[4,5-b]pyridinecarboxamide (Compound Ib-19)

N-[5-(5-isoxazolyl)-1,3,4-oxadiazol-2-yl]-5-phenyl-2-piperidino-7-thiazolo[4,5-b]pyridinecarboxamide (Compound Ib-20)

N-[5-(1-methyl-3-pyrazolyl)-1,3,4-oxadiazol-2-yl]-5-phenyl-2-piperidino-7-thiazolo[4,5-b]pyridinecarboxamide (Compound Ib-21)

N-[5-(2,4-dimethyl-5-thiazolyl)-1,3,4-oxadiazol-2-yl]-5-phenyl-2-piperidino-7-thiazolo[4,5-b]pyridinecarboxamide (Compound Ib-22)

N-[5-(3-pyridyl)-1,3,4-oxadiazol-2-yl]-5-phenyl-2-piperidino-7-thiazolo[4,5-b]pyridinecarboxamide (Compound Ib-23)

N-{5-[2-(2,3-dihydrobenzo[1,4], dioxinyl)]-1,3,4-oxadiazol-2-yl}-5-phenyl-2-piperidino-7-thiazolo[4,5-b]pyridinecarboxamide (Compound Ib-24)

5-phenyl-2-piperidino-N-{5-[2-(4,5,6,7-tetrahydrobenzothienyl)]-1,3,4-oxadiazol-2-yl}-7-thiazolo[4,5-b]pyridinecarboxamide (Compound Ib-25)

N-[5-(2-furyl)-1,3,4-oxadiazol-2-yl]-2-(1-pyrrolidinyl)-5-(2-thienyl)-7-thiazolo[4,5-b]pyridinecarboxamide (Compound Ib-26)

N-[5-(2-furyl)-1,3,4-oxadiazol-2-yl]-2-piperidino-5-(2-thienyl)-7-thiazolo[4,5-b]pyridinecarboxamide (Compound Ib-27)

N-[5-(2-furyl)-1,3,4-oxadiazol-2-yl]-2-morpholino-5-(2-thienyl)-7-thiazolo[4,5-b]pyridinecarboxamide (Compound Ib-28)

N-[5-(2-furyl)-1,3,4-oxadiazol-2-yl]-2-(1-pyrrolidinyl)-5-(3-pyridyl)-7-thiazolo[4,5-b]pyridinecarboxamide (Compound Ib-29)

N-[5-(2-furyl)-1,3,4-oxadiazol-2-yl]-5-phenyl-2-(4-thiomorpholinyl)-7-thiazolo[4,5-b]pyridinecarboxamide (Compound Ib-30)

N-[5-(2-furyl)-1,3,4-oxadiazol-2-yl]-2-(1-methyl-4-piperazinyl)-5-phenyl-7-thiazolo[4,5-b]pyridinecarboxamide (Compound Ib-31)

2-(4,4-difluoropiperidino)-N-[5-(2-furyl)-1,3,4-oxadiazol-2-yl]-5-phenyl-7-thiazolo[4,5-b]pyridinecarboxamide (Compound Ib-32)

(dl)-N-[5-(2-furyl)-1,3,4-oxadiazol-2-yl]-2-(2-methylpiperidino)-5-phenyl-7-thiazolo[4,5-b]pyridinecarboxamide (Compound Ib-33)

(dl)-N-[5-(2-furyl)-1,3,4-oxadiazol-2-yl]-5-phenyl-2-(3-trifluoromethylpiperidino)-7-thiazolo[4,5-b]pyridinecarboxamide (Compound Ib-34)

N-[5-(2-furyl)-1,3,4-oxadiazol-2-yl]-5-phenyl-2-(4-trifluoromethylpiperidino)-7-thiazolo[4,5-b]pyridinecarboxamide (Compound Ib-35)

2-(4-cyanopiperidino)-N-[5-(2-furyl)-1,3,4-oxadiazol-2-yl]-5-phenyl-7-thiazolo[4,5-b]pyridinecarboxamide (Compound Ib-36)

N-[5-(2-furyl)-1,3,4-oxadiazol-2-yl]-2-morpholino-5-phenyl-7-thiazolo[4,5-b]pyridinecarboxamide (Compound Ib-37)

2-(1-azetidinyl)-N-[5-(2-furyl)-1,3,4-oxadiazol-2-yl]-5-phenyl-7-thiazolo[4,5-b]pyridinecarboxamide (Compound Ib-38)

N-[5-(2-furyl)-1,3,4-oxadiazol-2-yl]-5-phenyl-2-(1-pyrrolidinyl)-7-thiazolo[4,5-b]pyridinecarboxamide (Compound Ib-39)

N-[5-(2-furyl)-1,3,4-oxadiazol-2-yl]-5-phenyl-2-(1,2,3,4-tetrahydro-1-quinolyl)-7-thiazolo[4,5-b]pyridinecarboxamide (Compound Ib-40)

2-acetylamino-N-[5-(2-furyl)-1,3,4-oxadiazol-2-yl]-5-phenyl-7-thiazolo[4,5-b]pyridinecarboxamide (Compound Ib-41)

2-tert-butoxycarbonylamino-N-[5-(2-furyl)-1,3,4-oxadiazol-2-yl]-5-phenyl-7-thiazolo[4,5-b]pyridinecarboxamide (Compound Ib-42)

N-[5-(2-furyl)-1,3,4-oxadiazol-2-yl]-2-(N-methylanilino)-5-phenyl-7-thiazolo[4,5-b]pyridinecarboxamide (Compound Ib-43)

N-[5-(2-furyl)-1,3,4-oxadiazol-2-yl]-2-(4-hydroxypiperidino)-5-phenyl-7-thiazolo[4,5-b]pyridinecarboxamide (Compound Ib-44)

N-[5-(2-furyl)-1,3,4-oxadiazol-2-yl]-5-phenyl-2-(4-phenylpiperidino)-7-thiazolo[4,5-b]pyridinecarboxamide (Compound Ib-45)

N-[5-(2-furyl)-1,3,4-oxadiazol-2-yl]-5-phenyl-2-(4-piperidinopiperidino)-7-thiazolo[4,5-b]pyridinecarboxamide (Compound Ib-46)

2-(2,2-dimethylmorpholino)-N-[5-(2-furyl)-1,3,4-oxadiazol-2-yl]-5-phenyl-7-thiazolo[4,5-b]pyridinecarboxamide (Compound Ib-47)

(dl)-2-[2-(2-azabicyclo[2.2.1], heptyl]-N-[5-(2-furyl)-1,3,4-oxadiazol-2-yl]-5-phenyl-7-thiazolo[4,5-b]pyridinecarboxamide (Compound Ib-48)

2-[N-methyl-N-(3,3,3-trifluoro-1-propyl)amino]-N-[5-(2-furyl)-1,3,4-oxadiazol-2-yl]-5-phenyl-7-thiazolo[4,5-b]pyridinecarboxamide (Compound Ib-49)

2-(N,N-dimethylamino)-N-[5-(2-furyl)-1,3,4-oxadiazol-2-yl]-5-phenyl-7-thiazolo[4,5-b]pyridinecarboxamide (Compound Ib-50)

2-amino-N-[5-(2-furyl)-1,3,4-oxadiazol-2-yl]-5-phenyl-7-thiazolo[4,5-b]pyridinecarboxamide (Compound Ib-51)

N-[5-(2-furyl)-1,3,4-oxadiazol-2-yl]-5-phenyl-2-furancarboxamide (Compound Ic-1)

5-(2-fluorophenyl)-N-[5-(2-furyl)-1,3,4-oxadiazol-2-yl]-2-furancarboxamide (Compound Ic-2)

N-[5-(2-furyl)-1,3,4-oxadiazol-2-yl]-5-(2-nitrophenyl)-2-furancarboxamide (Compound Ic-3)

5-(3-chlorophenyl)-N-[5-(2-furyl)-1,3,4-oxadiazol-2-yl]-2-furancarboxamide (Compound Ic-4)

N-[5-(2-furyl)-1,3,4-oxadiazol-2-yl]-5-(3-nitrophenyl)-2-furancarboxamide (Compound Ic-5)

5-(4-fluorophenyl)-N-[5-(2-furyl)-1,3,4-oxadiazol-2-yl]-2-furancarboxamide (Compound Ic-6)

5-(4-chlorophenyl)-N-[5-(2-furyl)-1,3,4-oxadiazol-2-yl]-2-furancarboxamide (Compound Ic-7)

N-[5-(2-furyl)-1,3,4-oxadiazol-2-yl]-5-(4-methoxyphenyl)-2-furancarboxamide (Compound Ic-8)

5-(4-aminophenyl)-N-[5-(2-furyl)-1,3,4-oxadiazol-2-yl]-2-furancarboxamide (Compound Ic-9)

5-(4-acetylaminophenyl)-N-[5-(2-furyl)-1,3,4-oxadiazol-2-yl]-2-furancarboxamide (Compound Ic-10)

N-[5-(2-furyl)-1,3,4-oxadiazol-2-yl]-5-(4-nitrophenyl)-2-furancarboxamide (Compound Ic-11)

5-(4-ethoxycarbonylphenyl)-N-[5-(2-furyl)-1,3,4-oxadiazol-2-yl]-2-furancarboxamide (Compound Ic-12)

5-(2,4-dichlorophenyl)-N-[5-(2-furyl)-1,3,4-oxadiazol-2-yl]-2-furancarboxamide (Compound Ic-13)

5-(2-chloro-4-nitrophenyl)-N-[5-(2-furyl)-1,3,4-oxadiazol-2-yl]-2-furancarboxamide (Compound Ic-14)

5-(4-amino-2-methylphenyl)-N-[5-(2-furyl)-1,3,4-oxadiazol-2-yl]-2-furancarboxamide (Compound Ic-15)

5-(4-acetylamino-2-methylphenyl)-N-[5-(2-furyl)-1,3,4-oxadiazol-2-yl]-2-furancarboxamide (Compound Ic-16)

N-[5-(2-furyl)-1,3,4-oxadiazol-2-yl]-5-(2-methyl-4-nitrophenyl)-2-furancarboxamide (Compound Ic-17)

N-[5-(2-furyl)-1,3,4-oxadiazol-2-yl]-5-(2-methoxy-4-nitrophenyl)-2-furancarboxamide (Compound Ic-18)

5-(2-chloro-5-nitrophenyl)-N-[5-(2-furyl)-1,3,4-oxadiazol-2-yl]-2-furancarboxamide (Compound Ic-19)

5-(4-chloro-3-nitrophenyl)-N-[5-(2-furyl)-1,3,4-oxadiazol-2-yl]-2-furancarboxamide (Compound Ic-20)

5-(3,5-dichlorophenyl)-N-[5-(2-furyl)-1,3,4-oxadiazol-2-yl]-2-furancarboxamide (Compound Ic-21)

N-[5-(2-furyl)-1,3,4-oxadiazol-2-yl]-2-methyl-5-phenyl-3-furancarboxamide (Compound Ic-22)

N-[5-(2-furyl)-1,3,4-oxadiazol-2-yl]-5-phenyl-2-thiophenecarboxamide (Compound Ic-23)

5-(4-cyanophenyl)-N-[5-(2-furyl)-1,3,4-oxadiazol-2-yl]-2-thiophenecarboxamide (Compound Ic-24)

N-[5-(2-furyl)-1,3,4-oxadiazol-2-yl]-3-phenyl-1-(6,7,8,9-tetrahydro-5H-imidazo[1,5-a]azepinecarboxamide (Compound Ic-25)

3-(4-fluorophenyl)-N-[5-(2-furyl)-1,3,4-oxadiazol-2-yl]-1-(6,7,8,9-tetrahydro-5H-imidazo[1,5-a]azepinecarboxamide (Compound Ic-26)

4-(4-biphenylyl)-N-[5-(2-furyl)-1,3,4-oxadiazol-2-yl]-2-thiophenecarboxamide (Compound Ic-27)

4-(4'-ethyl-4-biphenylyl)-N-[5-(2-furyl)-1,3,4-oxadiazol-2-yl]-2-thiophenecarboxamide (Compound Ic-28)

5-(4-carboxyphenyl)-N-[5-(2-furyl)-1,3,4-oxadiazol-2-yl]-2-furancarboxamide (Compound Ic-29).

Furthermore, the present invention relates to:

(11) a medicine containing a 1,3,4-oxadiazole-2-carboxamide compound according to any of (1) to (10) or a pharmaceutically acceptable salt thereof;

(12) an anticancer agent containing, as an active ingredient, a 1,3,4-oxadiazole-2-carboxamide compound according to any of (1) to (10) or a pharmaceutically acceptable salt thereof;

(13) a STAT3 inhibitor containing, as an active ingredient, a 1,3,4-oxadiazole-2-carboxamide compound according to any of (1) to (10) or a pharmaceutically acceptable salt thereof;

(14) a 1,3,4-oxadiazole-2-carboxamide compound according to any of (1) to (10) or a pharmaceutically acceptable salt thereof for use in the treatment of cancer;

(15) use of a 1,3,4-oxadiazole-2-carboxamide compound according to any of (1) to (10) or a pharmaceutically acceptable salt thereof for the manufacture of an anticancer agent; and

(16) a method of treating cancer including administering a 1,3,4-oxadiazole-2-carboxamide compound according to any of (1) to 10 or a pharmaceutically acceptable salt thereof.

Effects of the Invention

A novel 1,3,4-oxadiazole-2-carboxamide compound of the present invention has excellent STAT3 inhibitory activity, which has been unknown so far, and is useful as an anticancer agent for various cancers.

MODE FOR CARRYING OUT THE INVENTION

Hereinafter, the definition of each group in a compound (I) will be exemplified specifically. However, they are shown as preferable examples of the present invention and do not limit the present invention, as a matter of course.

Examples of an alkyl group include linear or branched alkyl having 1 to 12 carbon atoms, specifically, methyl, ethyl, propyl, isopropyl, butyl, isobutyl, sec-butyl, tert-butyl, pentyl, isopentyl, neopentyl, hexyl, heptyl, octyl, nonyl, decyl, undecyl, and dodecyl.

A cycloalkyl group is a 3- to 12-membered cycloalkyl group which may contain a saturated or partially unsaturated bond, and may be a monocyclic cycloalkyl group or a polycyclic condensed cycloalkyl group containing a plurality of the monocyclic cycloalkyl groups condensed or the monocyclic cycloalkyl group condensed with an aryl or aromatic heterocyclic group. Examples of the monocyclic cycloalkyl group include monocyclic cycloalkyl having 3 to 8 carbon atoms, specifically, cyclopropyl, cyclobutyl, cyclopentyl, cyclohexyl, cycloheptyl, cyclooctyl, cyclododecyl, and 1-cyclohexenyl. Examples of the polycyclic cycloalkyl group include polycyclic cycloalkyl having 5 to 12 carbon atoms, specifically, pinanyl, adamantyl, bicyclo[3.3.1], octyl, and bicyclo[3.1.1], heptyl.

Examples of an alkenyl group include linear or branched alkenyl having 2 to 12 carbon atoms, specifically, vinyl, allyl, 1-propenyl, isopropenyl, 2-methyl-allyl, butenyl, 1,3-butadienyl, crotyl, pentenyl, hexenyl, heptenyl, decenyl, and dodecenyl.

Examples of an alkynyl group include linear or branched alkynyl having 2 to 12 carbon atoms, specifically, ethynyl, propargyl, 1-propynyl, isopropynyl, 2-butynyl, pentynyl, 2-penten-4-ynyl, hexynyl, heptynyl, decynyl, and dodecynyl.

An alicyclic heterocyclic group is a 3- to 8-membered alicyclic heterocyclic group which contains at least one or more identical or different heteroatoms, for example, nitrogen, oxygen, and sulfur and may contain a saturated or partially unsaturated bond, and may be a monocyclic alicyclic heterocyclic group or a polycyclic condensed alicyclic heterocyclic group containing a plurality of the monocyclic heterocyclic groups condensed or the monocyclic heterocyclic group condensed with an aryl or aromatic heterocyclic group. Examples of the monocyclic alicyclic heterocyclic group can specifically include aziridinyl, azetidinyl, pyrrolidinyl, imidazolidinyl, imidazolinyl, pyrazolidinyl, pyrazolinyl, dihydrothiazolyl, tetrahydrofuranyl, 1,3-dioxolanyl, thiolanyl, oxazolidyl, thiazolidinyl, piperidino, piperidyl, piperazinyl, homopiperidinyl, morpholino, morpholinyl, thiomorpholinyl, pyranyl, oxathianyl, oxadiazinyl, thiadiazinyl, dithiazinyl, azepinyl, dihydroazocinyl, and azabicyclo[2.2.1], heptyl. Examples of the polycyclic condensed alicyclic heterocyclic group can specifically include indolinyl, isoindolinyl, chromanyl, isochromanyl, and quinuclidinyl.

In the alicyclic heterocyclic alkyl group, the alicyclic heterocyclic moiety is as defined above in the alicyclic heterocyclic group, and the alkyl moiety is as defined above in the alkyl group. For example, the alicyclic heterocyclic alkyl group is an alicyclic heterocyclic $C_{1-12}$ alkyl containing at least one or more heteroatoms, and specific examples thereof include pyrrolidinylethyl, piperridinoethyl, and morpholinoethyl.

Examples of an aryl group include aryl having 6 to 14 carbon atoms, specifically, phenyl, naphthyl, anthryl, phenanthryl, biphenyl, phenyl-naphtyl, and aceoctenyl.

The aryl moiety of an aralkyl group is as defined above in the aryl group, and the alkyl moiety thereof is as defined above in the alkyl group. Examples thereof include aralkyl having 7 to 26 carbon atoms, i.e., $C_{6-14}$ aryl-$C_{1-12}$ alkyl, specifically, benzyl, phenethyl, phenylpropyl, phenylbutyl, benzhydryl, trityl, naphthylmethyl, naphthylethyl, and phenylcyclopropyl.

An aromatic heterocyclic group is a 5- or 6-membered aromatic heterocyclic group which contains at least one or more identical or different heteroatoms, for example, nitrogen, oxygen, and sulfur. The heterocyclic group may be a monocyclic heterocyclic group or a polycyclic condensed aromatic heterocyclic group (e.g., a bicyclic or tricyclic heterocyclic group) containing a plurality of the monocyclic heterocyclic groups condensed or the monocyclic heterocyclic group condensed with an aryl group. Specific examples of the monocyclic aromatic heterocyclic group include furyl, thienyl, pyrrolyl, imidazolyl, pyrazolyl, triazolyl, tetrazolyl, oxazolyl, isoxazolyl, oxadiazolyl, thiazolyl, thiadiazolyl, isothiazolyl, pyridyl, pyrimidinyl, pyrazinyl, pyridazinyl, and triazinyl. Examples of the polycyclic condensed aromatic heterocyclic group include benzofuryl, benzothienyl, indolyl, isoindolyl, indazolyl, benzimidazolyl, benzotriazolyl, benzoxazolyl, benzothiazolyl, carbazolyl, purinyl, quinolyl, isoquinolyl, quinazolinyl, phthalazinyl, quinoxalinyl, cinnolinyl, naphtylidinyl, pyridopyrimidinyl, pyrimidopyrimidinyl, pteridinyl, acridinyl, thianthrenyl, phenoxathinyl, phenoxazinyl, phenothiazinyl, phenazinyl, and benzofurazanyl.

The aromatic heterocyclic moiety of an aromatic heterocyclic alkyl group is as defined above in the aromatic heterocyclic group, and the alkyl moiety thereof is as defined above in the alkyl group. Examples thereof include aromatic heterocyclic $C_{1-12}$ alkyl containing at least one or more heteroatoms, specifically, pyridylmethyl, pyridylethyl, furanylmethyl, and thienylmethyl.

A nitrogen-containing heterocyclic group is, of the alicyclic or aromatic heterocyclic groups, a heterocyclic group containing at least one nitrogen atom as a heteroatom. Specific examples thereof include aziridinyl, azetidinyl, pyrrolidinyl, piperidino, homopiperidinyl, piperazinyl, homopiperazinyl, azabicyclo[2.2.1], heptyl, morpholino, thiomorpholinyl, pyrrolyl, imidazolyl, pyrazolyl, triazolyl, tetrazolyl, indolyl, indazolyl, benzimidazolyl, benzotriazolyl, and tetrahydroquinolyl.

A halogen atom means each of fluorine, chlorine, bromine, and iodine atoms.

Examples of the dioxaborolanyl group include a 4,4,5,5-tetramethyl-1,3,2-dioxaborolan-2-yl group.

Examples of the halogen atom of the pentahalogenothio group include those mentioned above. Specifically, the pentahalogenothio group is preferably a pentafluorothio group.

Moreover, these groups respectively represent all of their possible positional isomers, if any.

Substituents for the alkyl group, the alkenyl group, the alkynyl group, the cycloalkyl group, the alicyclic heterocyclic group, the alicyclic heterocyclic alkyl group, the aryl group, the aralkyl group, the aromatic heterocyclic group, the aromatic heterocyclic alkyl group, and the nitrogen-containing heterocyclic group are appropriately selected from, for example, an alkyl group, an alkenyl group, an alkynyl group, a cycloalkyl group, an alicyclic heterocyclic group, an alicyclic heterocyclic alkyl group, an aryl group, an aralkyl group, an aromatic heterocyclic group, an aromatic heterocyclic alkyl group, $OR^a$, $NR^bR^c$, $S(O)tR^d$, (wherein t represents 0, 1, or 2), $COR^e$, $COOR^f$, $OCOR^g$, $CONR^hR^i$, $NR^jCOR^k$, $NR^l\text{-}COOR^m$, $NR''SO_2R^o$, $C(=NR^p)NR^qR^r$, $NR^sSO_2NR^tR^u$, $SO_2NR^vR^w$, a nitro group, a cyano group, a halogen atom, an oxo group, and a thioxo group. In this context, $R^a$ to $R^w$ are the same or different and each represent a hydrogen atom, an alkyl group, an alkenyl group, an alkynyl group, a cycloalkyl group, an alicyclic heterocyclic group, an alicyclic heterocyclic alkyl group, an aryl group, an aralkyl group, an aromatic heterocyclic group, an aromatic heterocyclic alkyl group, or the like, and $R^b$ and $R^c$, $R^h$ and $R^i$, $R^q$ and $R^r$, $R^t$ and $R^u$, and $R^v$ and $R^w$ may be linked together to form a nitrogen-containing heterocyclic group.

The alkyl, alkenyl, alkynyl, cycloalkyl, alicyclic heterocyclic, alicyclic heterocyclic alkyl, aryl, aralkyl, aromatic heterocyclic, aromatic heterocyclic alkyl, and nitrogen-containing heterocyclic groups are as defined above.

Moreover, the alkyl, alkenyl, alkynyl, cycloalkyl, alicyclic heterocyclic, alicyclic heterocyclic alkyl, aryl, aralkyl, aromatic heterocyclic, aromatic heterocyclic alkyl, and nitrogen-containing heterocyclic groups as substituents may further have a substituent. Examples of this substituent include the same as the substituents exemplified above.

The number of substitutions by these substituents may be the number of hydrogen atoms present in each group (these hydrogen atoms may be substituted by identical or different substituents), at the maximum, and is preferably 1 to 10, more preferably 1 to 5.

In formula (I), Ar is more preferably group (1) or group (3), even more preferably group (3). Preferred examples of Ar include furyl groups, thienyl groups, pyrazolyl groups, oxazolyl groups, isooxazolyl groups, thiazolyl groups, isothiazolyl groups, phenyl groups, benzyl groups, and pyridyl groups. Thienyl groups and furyl groups are more preferred, and furyl groups (in group (3), $Z^2$=O) are particularly preferred. These groups may be substituted by the m number of $R^2$ mentioned above.

$R^1$ is preferably a hydrogen atom or a $C_{1-2}$ alkyl group, and particularly preferably a hydrogen atom.

X is preferably phenyl, pyridyl, thiazolopyridyl, isoxazolopyridyl, imidazoazepinyl, thienyl, or furyl, more preferably phenyl, pyridyl, thiazolopyridyl, or furyl, and particularly preferably phenyl or thiazolopyridyl. These groups may be substituted by the m number of $R^3$ mentioned above.

The aryl group represented by Y is preferably phenyl, naphthyl, biphenyl, phenyl-naphthyl, or acenaphthyl, particularly preferably phenyl or naphthyl. Examples of the aromatic heterocyclic group represented by Y include furyl, thienyl, pyrrolyl, imidazolyl, pyrazolyl, triazolyl, tetrazolyl, oxazolyl, isoxazolyl, oxadiazolyl, thiazolyl, thiadiazolyl, isothiazolyl, pyridyl, pyrimidinyl, pyrazinyl, pyridazinyl, triazinyl, benzofuryl, benzothienyl, indolyl, isoindolyl, indazolyl, benzoimidazolyl, benzotriazolyl, benzooxazolyl, benzothiazolyl, carbazolyl, purinyl, quinolyl, isoquinolyl, quinazolinyl, phthalazinyl, quinoxalinyl, cinnolinyl, naphthyridinyl, pyridopyrimidinyl, pyrimidopyrimidinyl, pteridinyl, acridinyl, thianthrenyl, phenoxathinyl, phenoxazinyl, phenothiazinyl, and phenazinyl. These groups may be substituted by substituents mentioned above.

Examples of a pharmacologically acceptable salt of the compound represented by formula (I) include pharmacologically acceptable acid-addition salts, metal salts, ammonium salts, organic amine-addition salts, and amino acid-addition salts. Examples of the pharmacologically acceptable acid-addition salts include salts of inorganic acids such as hydrochloric acid, hydrobromic acid, sulfuric acid, nitric acid, phosphoric acid, and boric acid, or organic acids such as carboxylic acids (e.g., formic acid, acetic acid, propionic acid, fumaric acid, malonic acid, succinic acid, maleic acid, tartaric acid, citric acid, and benzoic acid), sulfonic acids (e.g., methanesulfonic acid and p-toluenesulfonic acid), and amino acids (e.g., glutamic acid and aspartic acid). Examples of the pharmacologically acceptable metal salts include: salts of alkali metals such as lithium, sodium, and potassium; salts of alkaline earth metals such as magnesium and calcium; and salts of metals such as aluminum and zinc. Examples of the pharmacologically acceptable ammonium salts include salts of ammonium or tetramethylammonium. Examples of the pharmacologically acceptable organic amine salts include salts of triethylamine, piperidine, morpholine, or toluidine. Examples of the pharmacologically acceptable amino acid-addition salts include lysine-, glycine-, and phenylalanine-addition salts.

The compound represented by formula (I) of the present invention (hereinafter, referred to as compound (I); the same holds true for compounds represented by other formula numbers) has a STAT3 inhibitory activity and is useful as an anticancer agent. Any compound (I) can be used as an anticancer agent without particular limitation.

Next, a production method of the compound (I) will be described. The compound can be produced using a routine method or the acid amide synthesis method described in a document (e.g., The Chemical Society of Japan, ed., "Experimental Chemistry Guidebook 16, 5th ed., Synthesis of Organic compounds IV, Carboxylic Acid/Amino acid/Peptide", Maruzen Co., Ltd., March 2005, p. 118-146 and p. 258-270).

Production Method 1

The compound (I) can be produced according to the following reaction steps:

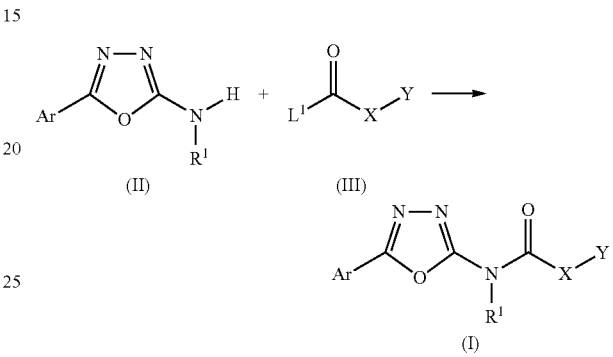

wherein $L^1$ represents a leaving group, and Ar, X, Y and $R^1$ are as defined above.

Examples of the leaving group defined as $L^1$ include a halogen atom, a hydroxyl group, a substituted or unsubstituted alkoxy group, a substituted or unsubstituted aryloxy group, and a substituted or unsubstituted alkylcarbonyloxy group. The halogen atom is as defined above. The alkyl moieties of the alkoxy and alkylcarbonyloxy groups are as defined above in the alkyl group. Examples thereof include alkoxy and alkylcarbonyloxy groups having 1 to 12 carbon atoms. Moreover, the aryl moieties of the aryloxy and arylcarbonyloxy groups are as defined above in the aryl group. Examples thereof include aryloxy and arylcarbonyloxy groups having 6 to 12 carbon atoms. Examples of substituents include a halogen atom and a nitro group. The halogen atom is as defined above. Specific examples of the leaving group include: alkoxy groups such as methoxy; aryloxy groups such as pentafluorophenoxy and 4-nitrophenoxy; and alkylcarbonyloxy groups such as pivaloyloxy.

The compound (I) can be obtained by reacting a compound (II) with a compound (III) at a temperature of −78° C. to the boiling point of a solvent used for 5 minutes to 48 hours in an appropriate inert solvent, for example, halogenated hydrocarbon (e.g., chloroform and dichloromethane), aromatic hydrocarbon (e.g., benzene and toluene), an ether solvent (e.g., diethyl ether, tetrahydrofuran (THF), and 1,4-dioxane), an aprotic polar solvent (e.g., N,N-dimethylformamide (DMF), N-methylpyrrolidone (NMP), and dimethyl sulfoxide (DMSO)), a basic solvent (e.g., pyridine and quinoline), or a mixed solvent thereof, optionally in the presence of a base.

Examples of the base include: organic bases such as triethylamine and pyridine; inorganic bases such as potassium carbonate, potassium bicarbonate, tripotassium phosphate, sodium hydroxide, and sodium hydride; and metal alkoxides such as sodium methoxide and potassium tert-butoxide.

In the present reaction, a condensing agent may be allowed to coexist, particularly when $L^1$ is a hydroxyl group. The condensing agent may be any of those described in the above-mentioned article, for example, a carbodiimide condensing agent such as N,N-dicyclohexyl carbodiimide (DCC) or 1-ethyl-3-(3-dimethylaminopropyl)-carbodiimide (WSCI); a phosphonium condensing agent such as benzotriazol-1-yloxy-trisdimethylaminophosphonium salt (BOP); O-(7-azabenzotriazol-1-yl)-N,N,N',N'-tetramethyluronium hexafluorophosphate (HATU); O-(benzotriazol-1-yl)-N,N,N',N'-tetramethyluronium hexafluorophosphate (HBTU); 4-(4,6-dimethoxy-1,3,5-triazin-2-yl)-4-methylmorpholinium chloride (DMT-MM); carbonyldiimidazole (CDI); diphenylphosphinic acid chloride (DPP-Cl), etc. In such a case, a condensation aid such as 1-hydroxy-7-azabenzotriazole (HOAt) or 1-hydroxybenzotriazole (HOBt) may coexist.

The compounds (II) and (III) are commercially available or can be obtained according to a method described in documents (for the compound (II), Tetrahedron Lett., 2006, 47, 4889-4891, and 2004, 45, 7157-7161; and for the compound (III), Jie Jack Li et al., Palladium in Heterocyclic chemistry, Pergamon Press), a method described in Production or Reference Examples, etc., or an equivalent thereto.

Production Method 2

Compound (I) can also be produced according to the following reaction steps:

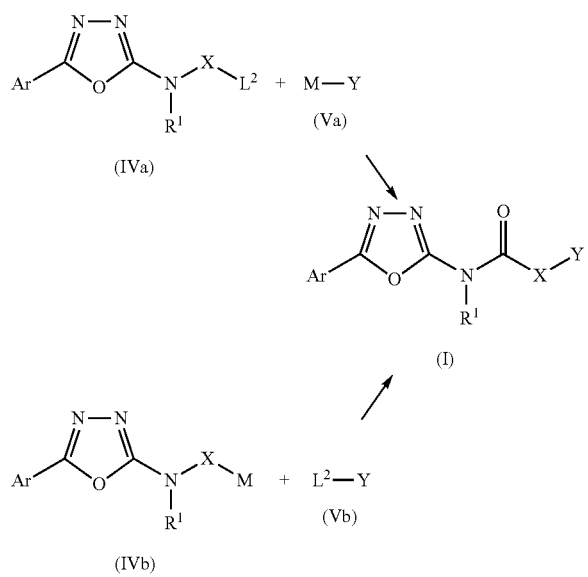

wherein $L^2$ represents a leaving group; M represents a metal-containing leaving group; and Ar, X, Y, and $R^1$ are as defined above.

Examples of the leaving group in definition of $L^2$ include halogen atoms, substituted or unsubstituted alkylsulfonyloxy groups, and substituted or unsubstituted arylsulfonyloxy groups. The halogen atoms are as defined above. The alkyl moieties of the alkylsulfonyloxy groups are as defined above in the alkyl group. Examples thereof include alkylsulfonyloxy groups having 1 to 12 carbon atoms. The aryl moieties of the arylsulfonyloxy groups are as defined above in the aryl group. Examples thereof include arylsulfonyloxy groups having 6 to 12 carbon atoms. Examples of substituents include halogen atoms, alkyl groups, and nitro groups. The halogen atoms and the alkyl groups are as defined above. Specific examples of the leaving group include alkylsulfonyloxy groups such as methanesulfonyloxy and trifluoromethanesulfonyloxy and arylsulfonyloxy groups such as benzenesulfonyloxy and toluenesulfonyloxy.

Examples of the metal of metal-containing leaving group in definition of M include lithium, boron, magnesium, aluminum, silicon, zinc, and tin. Specific examples of the metal-containing leaving group include —B(OH)$_2$, —B(—OC(CH$_3$)$_2$C(CH$_3$)$_2$O—)$_2$, —MgCl, —MgBr, —ZnBr, —ZnI, —Sn(nBu)$_3$, and —SiCl$_2$(C$_2$H$_5$).

Compound (I) can be obtained by a cross-coupling reaction between a compound (IVa) and a compound (Va) or between a compound (IVb) and a compound (Vb) in the presence of a transition-metal catalyst and a base in an appropriate inert solvent.

Examples of the transition metal of the transition-metal catalyst include palladium, nickel, copper, and iron. Specific examples of the transition-metal catalyst include tetrakis(triphenylphosphine)palladium(0) and tetrakis(triphenylphosphine)nickel(0). These transition-metal catalysts may be prepared in situ from corresponding transition metal salts and other components in the presence of ligands. Examples of the ligands include triphenylphosphine, tributylphosphine, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, and 2,2'-bis(diphenylphosphino)-1,1'-binaphthyl. Examples of the transition-metal salt and other components include palladium chloride, palladium acetate, palladium-carbon, nickel chloride, copper(I) chloride, copper(I) oxide, iron(II) chloride, and iron(III) chloride.

Bases to be used, reaction solvents, reaction temperatures and times, and so on can be approximately the same conditions as in Production Method 1.

The compounds (IVa) and (IVb) and the compounds (Va) and (Vb) are commercially available or can be obtained by methods described in the above-mentioned documents or Reference Examples or methods in accordance therewith.

Production Method 3

Compound (I-1) which is a compound (I) wherein $R^1$ is a hydrogen atom can also be produced by the following reaction steps:

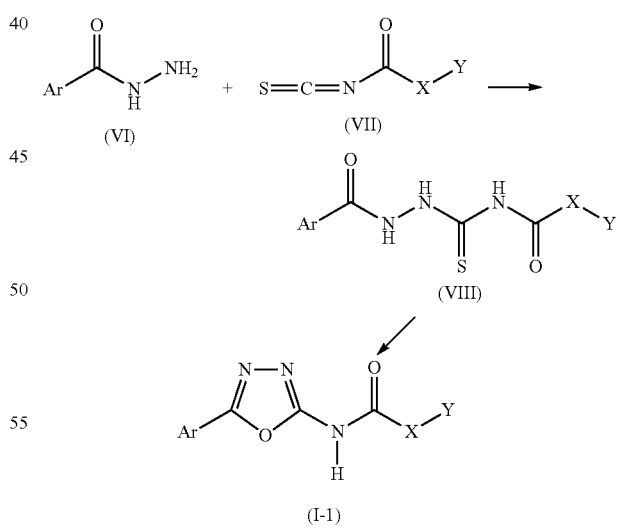

wherein Ar, X, and Y are as defined above.

Compound (I-1) can be obtained by condensing a compound (VI) and a compound (VII) optionally in the presence of a base into a compound (VIII) and then subjecting the compound (VIII) to annelation in the presence of an alkylsulfonyl chloride, alkylsulfonic anhydride, arylsulfonyl chloride, or oxidizing agent.

The alkyl moieties of the alkylsulfonyl chloride and the alkylsulfonic anhydride are as defined above in the alkyl group, and examples thereof include alkyl groups having 1 to 12 carbon atoms. The aryl moiety of the arylsulfonyl chloride is as defined above in the aryl group, and examples thereof include aryl groups having 6 to 12 carbon atoms. Examples of the substituent include alkyl groups, trifluoromethyl groups, halogen atoms, and nitro groups. The alkyl groups and the halogen atoms are as defined above. Specific examples thereof include methanesulfonyl chloride, trifluoromethanesulfonic anhydride, and toluenesulfonyl chloride.

Examples of the oxidizing agent include iodine, N-bromosuccinimide (NBS), and 1,3-dibromo-5,5-dimethylhydantoin.

Bases to be used, reaction solvents, reaction temperatures and times, and so on can be approximately the same conditions as in Production Method 1.

The compounds (VI) and (VII) are commercially available or can be produced according to a routine method, a method described in documents (e.g., for the compound (VII), the acyl isothiocyanate synthesis method described in The Chemical Society of Japan, ed., "Experimental Chemistry Guidebook 20, 4th ed., Organic Synthesis II", Maruzen Co. Ltd., July 1992, p. 488), or an equivalent thereto.

In each of these production methods, when the defined groups are altered under the conditions of the performed method or are inappropriate for performing the method, the compound of interest can be obtained using protective group introduction and elimination methods (see e.g., Protective Groups in Organic Synthesis, T. W. Greene, John Wiley & Sons Inc., 1981), etc., routinely used in organic synthetic chemistry. Moreover, the conversion of a functional group contained in each substituent can also be performed by a method known in the art (e.g., Comprehensive Organic Transformations, R. C. Larock, 1989), in addition to the production methods. Some compounds (I) can further be converted as synthesis intermediates to another derivative (I).

The intermediates and the compound of interest in each of the production methods can be isolated and purified by a purification method routinely used in organic synthetic chemistry, for example, neutralization, filtration, extraction, washing, drying, concentration, recrystallization, and various chromatography techniques. Moreover, the intermediates may be subjected to next reaction without being particularly purified.

Some compounds (I) can have isomers. In the present invention, all of possible isomers and their mixtures can be used as anticancer agents.

To obtain a salt of the compound (I), the compound (I) obtained in the form of a salt can be purified directly. Alternatively, the compound (I) obtained in a free form can be dissolved or suspended in an appropriate organic solvent to form a salt by a usual method by the addition of an acid or a base.

Moreover, the compound (I) and the pharmacologically acceptable salt thereof may be present in the form of adducts with water or various solvents. These adducts can also be used as the STAT3 inhibitor of the present invention.

Specific examples of the compound (I) obtained by the production methods are shown in Tables 1 to 24.

TABLE 1

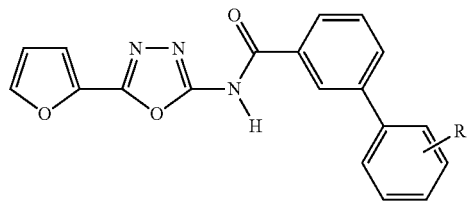

Ia-1: R = H
Ia-2: R = 2-OH
Ia-3: R = 2-CHO
Ia-4: R = 3-OH
Ia-5: R = 3-NO$_2$
Ia-6: R = 3-CHO
Ia-7: R = 3-COOMe
Ia-8: R = 3-COOH
Ia-9: R = 3-CN
Ia-10: R = 4-F
Ia-11: R = 4-Cl
Ia-12: R = 4-Me
Ia-13: R = 4-CH=CH$_2$
Ia-14: R = 4-tBu
Ia-15: R = 4-OH
Ia-16: R = 4-OMe
Ia-17: R = 4-CHO
Ia-18: R = 4-COCH$_3$
Ia-19: R = 4-COPh
Ia-20: R = 4-CONH$_2$
Ia-21: R = 4-CN
Ia-22: R = 4-CH$_2$CN
Ia-23: R = 4-COOn-Bu
Ia-24: R = 4-NO$_2$
Ia-25: R = 4-SO$_2$NH$_2$
Ia-26: R = 4-SO$_2$NHMe
Ia-27: R = 4-SO$_2$NMe$_2$
Ia-28: R = 4-SO$_2$Me
Ia-29: R = 2-Me,4-CN
Ia-30: R = 3-F,4-COCH$_3$

TABLE 2

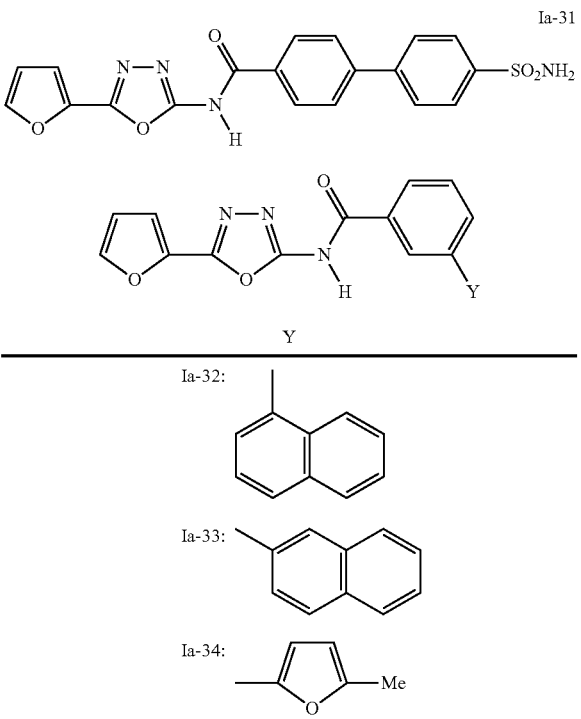

TABLE 2-continued
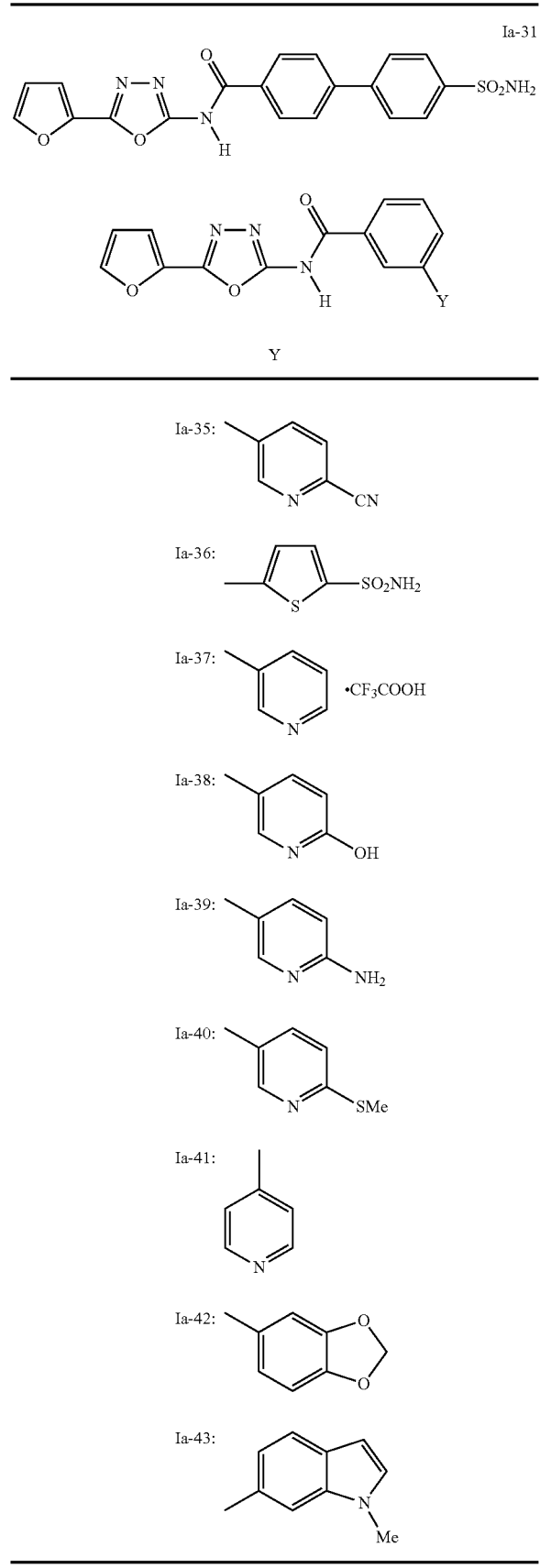
TABLE 3
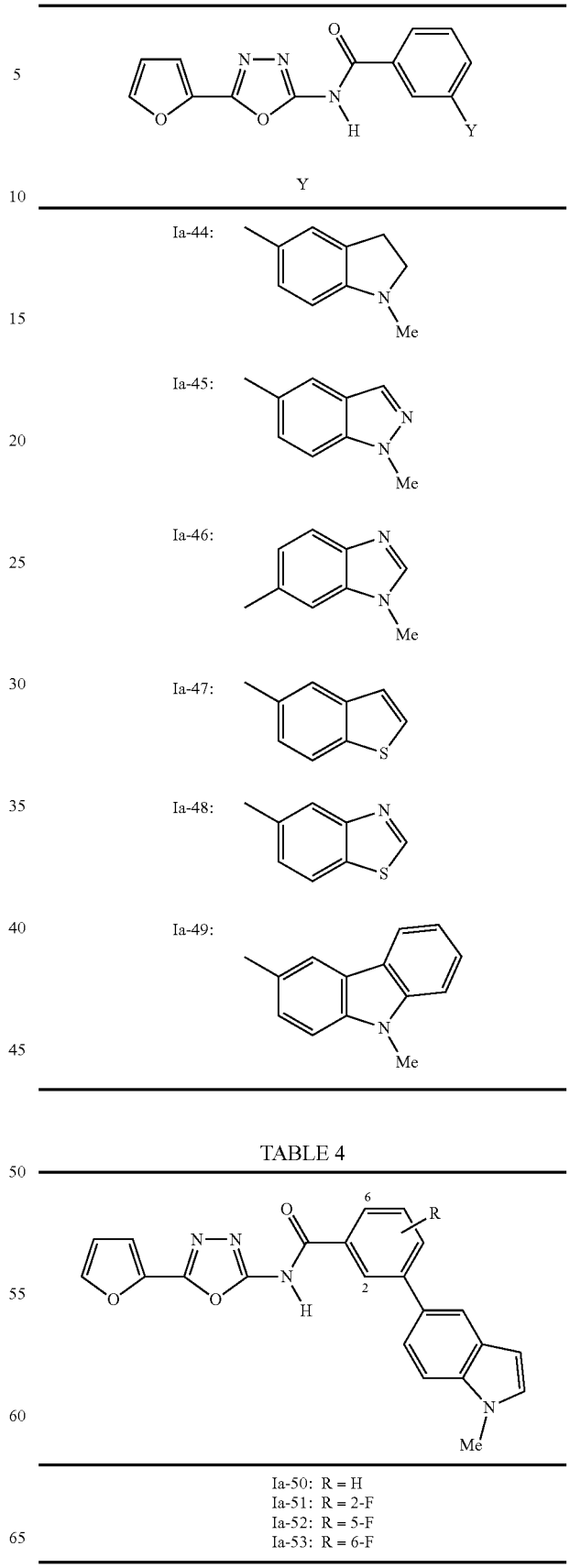

TABLE 5

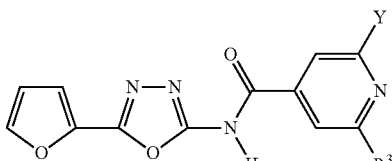

| | R³ | Y |
|---|---|---|
| Ia-54: | H | phenyl |
| Ia-55: | 4-methylphenyl | phenyl |
| Ia-56: | 4-Cl-phenyl | 4-Br-phenyl |

TABLE 6

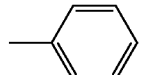

| | Y |
|---|---|
| Ia-57: | 2-phenyl |
| Ia-58: | 3-(5-methyl-1-methyl-indol-3-yl) |

TABLE 7

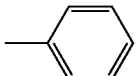

Ia-59: 3-F-4-CN
Ia-60: 4-(CMe$_2$—CN)
Ia-61: 3-NO$_2$-4-tBu
Ia-62: 4-SiMe$_3$
Ia-63: 4-CF$_3$
Ia-64: 4-OCF$_3$
Ia-65: 4-CH$_2$Ph
Ia-66: 4-OPh
Ia-67: 4-NPh$_2$
Ia-68: 4-NHCONH$_2$
Ia-69: 4-COOMe
Ia-70: 4-COEt

TABLE 7-continued

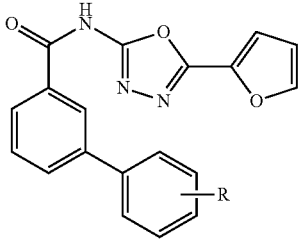

Ia-71: 4-SO$_2$-piperidino
Ia-72: 4-SO$_3$H
Ia-73: 2-Ph
Ia-74: 3-Ph
Ia-75: 4-Ph
Ia-76: 3-F-4-Ph
Ia-77: 4-(4-Cl—Ph)
Ia-78: 4-(4-Et—Ph)
Ia-79: 4-(4-EtO—Ph)
Ia-80: 4-(4-nPrO—Ph)
Ia-81: 4-(4-iPrO—Ph)
Ia-82: 4-(1-naphthyl)
Ia-83: 4-(2-naphthyl)
Ia-84: 4-cHex
Ia-85: 4-(trans-4-propylcyclohexyl)
Ia-86: 3-morphorino
Ia-87: 4-morphorino
Ia-88: 4-[1-(4-Boc-piperazinyl)]
Ia-89: 4-(1-piperazinyl)
Ia-90: 4-(2-morpholinoethyl)

TABLE 8

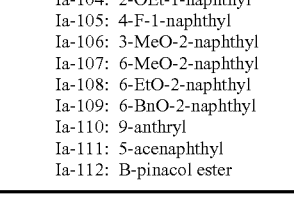

| | R |
|---|---|
| Ia-91: | 2-pyridyl |
| Ia-92: | 2-CN-5-pyridyl |
| Ia-93: | 2-CF$_3$-5-pyridyl |
| Ia-94: | 2-morpholino-3-pyridyl |
| Ia-95: | 2-morpholino-4-pyridyl |
| Ia-96: | 2-(1-piperazinyl)-5-pyridyl |
| Ia-97: | 5-Ph-2-thienyl |
| Ia-98: | 2-morpholino-5-pyrimidinyl |
| Ia-99: | 3-quinolyl |
| Ia-100: | 6-quinoxalinyl |
| Ia-101: | 5-benzofurazanyl |
| Ia-102: | 3,4-ethylenedioxy-Ph |
| Ia-103: | 4-Me-1-naphthyl |
| Ia-104: | 2-OEt-1-naphthyl |
| Ia-105: | 4-F-1-naphthyl |
| Ia-106: | 3-MeO-2-naphthyl |
| Ia-107: | 6-MeO-2-naphthyl |
| Ia-108: | 6-EtO-2-naphthyl |
| Ia-109: | 6-BnO-2-naphthyl |
| Ia-110: | 9-anthryl |
| Ia-111: | 5-acenaphthyl |
| Ia-112: | B-pinacol ester |

TABLE 9

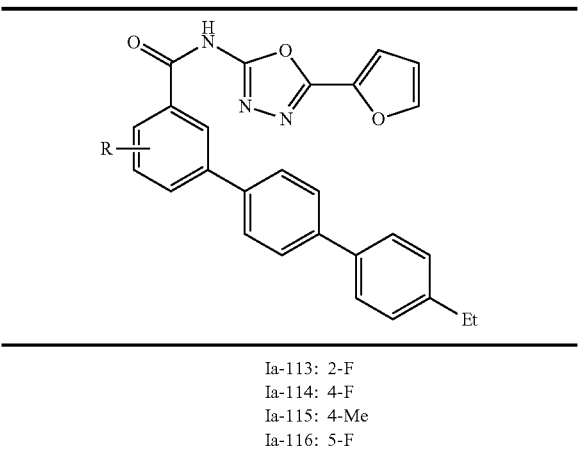

| | |
|---|---|
| Ia-113: | 2-F |
| Ia-114: | 4-F |
| Ia-115: | 4-Me |
| Ia-116: | 5-F |

TABLE 10

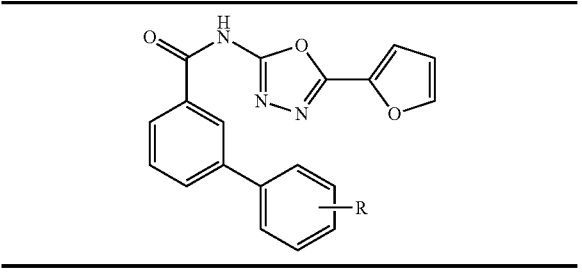

| | |
|---|---|
| Ia-121: | 4-Br |
| Ia-122: | 4-(2-F—Ph) |
| Ia-123: | 4-(2-Cl—Ph) |
| Ia-124: | 4-(2-Me—Ph) |
| Ia-125: | 4-(2-MeO—Ph) |
| Ia-126: | 4-(2-CF$_3$—Ph) |
| Ia-127: | 4-(2-CF$_3$O—Ph) |
| Ia-128: | 4-(2-CN—Ph) |
| Ia-129: | 4-(2-Ph—Ph) |
| Ia-130: | 4-(3-F—Ph) |
| Ia-131: | 4-(3-Cl—Ph) |
| Ia-132: | 4-(3-Me—Ph) |
| Ia-133: | 4-(3-MeO—Ph) |
| Ia-134: | 4-(3-CF$_3$—Ph) |
| Ia-135: | 4-(3-CF$_3$O—Ph) |
| Ia-136: | 4-(3-CN—Ph) |
| Ia-137: | 4-(3-Ph—Ph) |
| Ia-138: | 4-(4-F—Ph) |
| Ia-139: | 4-(4-Me—Ph) |
| Ia-140: | 4-(4-MeO—Ph) |
| Ia-141: | 4-(4-CF$_3$—Ph) |
| Ia-142: | 4-(4-CF$_3$O—Ph) |
| Ia-143: | 4-(4-CN—Ph) |
| Ia-144: | 4-(4-Ph—Ph) |
| Ia-145: | 4-(4-SiMe$_3$—Ph) |
| Ia-146: | 4-(1-cyclohexenyl) |
| Ia-147: | 4-(4,4-Me$_2$-1-cyclohexenyl) |
| Ia-148: | 4-(4-tBu-1-cyclohexenyl) |
| Ia-149: | 4-[4-(2,2,6,6,-Me$_4$-3,6-dihydropyranyl)] |
| Ia-150: | 4-[4-(1-Me-1,2,3,6-tetrahydropyridyl)] |
| Ia-151: | 4-(2-furyl) |
| Ia-152: | 4-(2-thienyl) |
| Ia-153: | 4-(3-thienyl) |
| Ia-154: | 4-(1-Me-4-pyrazolyl) |
| Ia-155: | 4-(4-pyridyl) |
| Ia-156: | 4-(1-Me-5-indolyl) |
| Ia-157: | 4-(3-OH—Ph) |
| Ia-158: | 4-(4-nPr—Ph) |
| Ia-159: | 4-(4-iPr—Ph) |
| Ia-160: | 4-(4-nBu—Ph) |
| Ia-161: | 4-(4-tBu—Ph) |
| Ia-162: | 4-(4-OH—Ph) |

TABLE 10-continued

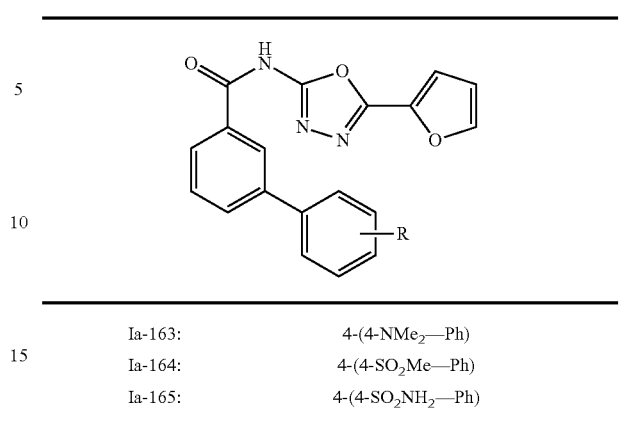

| | |
|---|---|
| Ia-163: | 4-(4-NMe$_2$—Ph) |
| Ia-164: | 4-(4-SO$_2$Me—Ph) |
| Ia-165: | 4-(4-SO$_2$NH$_2$—Ph) |

TABLE 11

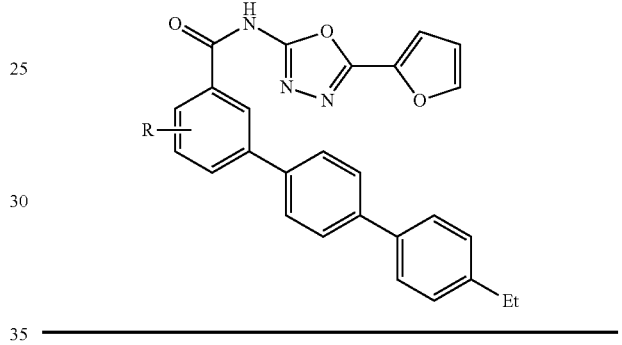

| | |
|---|---|
| Ia-166: | 5-Cl |
| Ia-167: | 5-NO$_2$ |
| Ia-168: | 5-NHAc |
| Ia-169: | 5-CF$_3$ |
| Ia-170: | 5-OCF$_3$ |
| Ia-171: | 5-CN |
| Ia-172: | 5-SF$_5$ |

TABLE 12

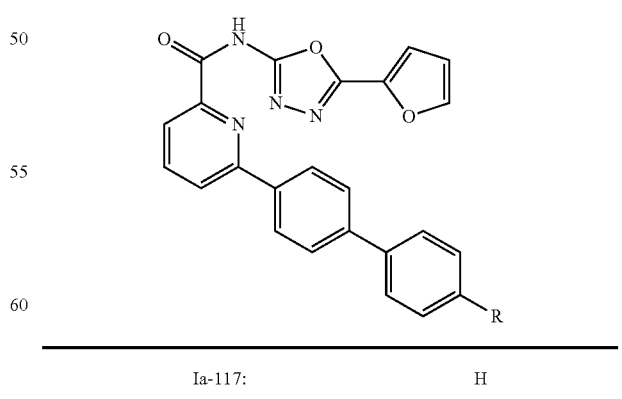

| | |
|---|---|
| Ia-117: | H |
| Ia-118: | Et |

TABLE 13
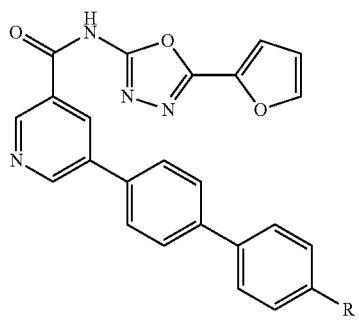
| | |
|---|---|
| Ia-119: | H |
| Ia-120: | Et |
TABLE 14
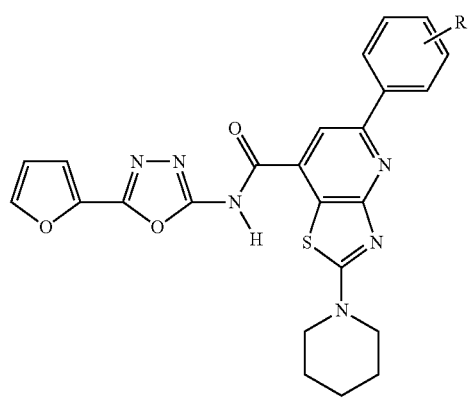
| | |
|---|---|
| Ib-1: | R = H |
| Ib-2: | R = 3-Cl |
| Ib-3: | R = 4-Me |
| Ib-4: | R = 3,4-(OMe)$_2$ |
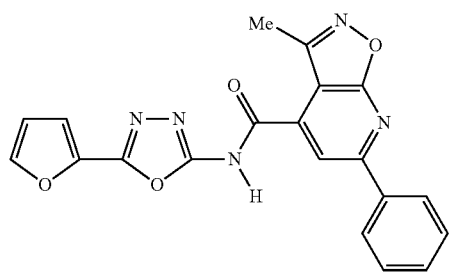 [SMILES: Cc1noc2nc(-c3ccccc3)cc(C(=O)Nc3nnc(-c4ccco4)o3)c12] Ib-5
TABLE 15
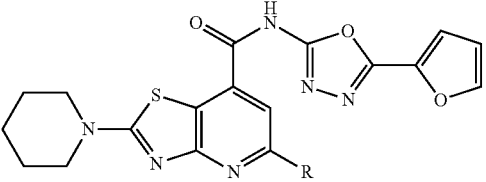
| | |
|---|---|
| Ib-6: | 2-naphthyl |
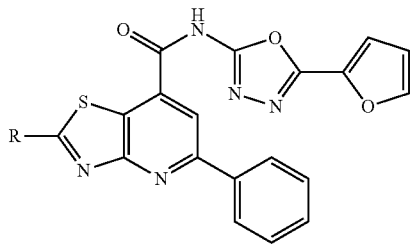
| | |
|---|---|
| Ib-7: | 4-Me-piperidino |
TABLE 16
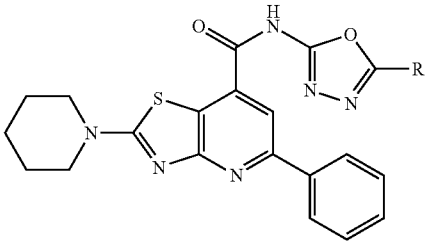
| Ib-8: | Ph | Ib-17: | 3-Me-2-thienyl |
|---|---|---|---|
| Ib-9: | 2-Cl—Ph | Ib-18: | 5-Me-2-thienyl |
| Ib-10: | 4-Cl—Ph | Ib-19: | 3-thienyl |
| Ib-11: | 4-OMe—Ph | Ib-20: | 5-isoxazolyl |
| Ib-12: | 4-NO$_2$—Ph | Ib-21: | 1-Me-3-pyrazolyl |
| Ib-13: | CH$_2$Ph | Ib-22: | 2,4-Me$_2$-5-thiazolyl |
| Ib-14: | 2-Me-3-furyl | Ib-23: | 3-pyridyl |
| Ib-15: | 2,5-Me$_2$-3-furyl | Ib-24: | 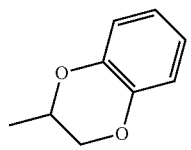 |
| Ib-16: | 2-thienyl | Ib-25: | 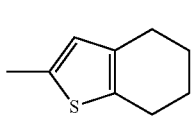 |

TABLE 17

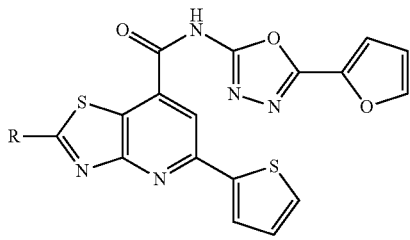

| | |
|---|---|
| Ib-26: | pyrrolidino |
| Ib-27: | piperidino |
| Ib-28: | morpholino |

TABLE 18

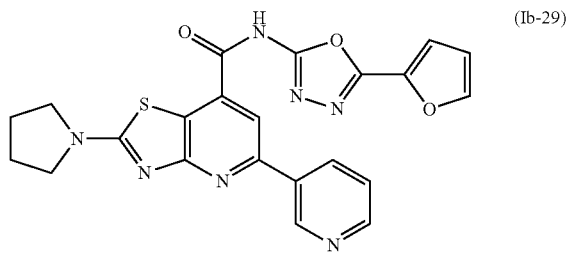
(Ib-29)

TABLE 19

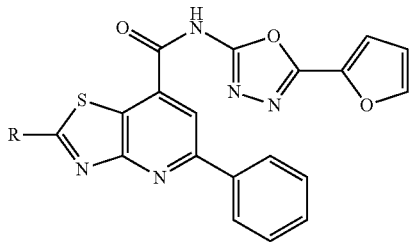

| | |
|---|---|
| Ib-30: | 4-thiomorpholinyl |
| Ib-31: | 1-(4-Me-piperazinyl) |
| Ib-32: | 4,4-F2-piperidino |

TABLE 20

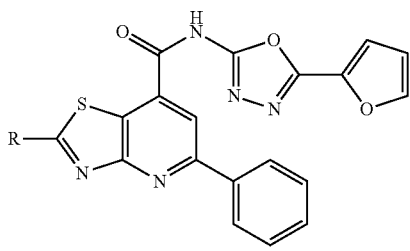

| | |
|---|---|
| Ib-33: | (dI)-2-Me-piperidino |
| Ib-34: | (dI)-3-CF$_3$-piperidino |
| Ib-35: | 4-CF$_3$-piperidino |
| Ib-36: | 4-CN-piperidino |
| Ib-37: | morpholino |
| Ib-38: | 1-azetidinyl |
| Ib-39: | 1-pyrrolidinyl |
| Ib-40: | 1-(1,2,3,4-tetrahydroquinolyl) |
| Ib-41: | NHAc |
| Ib-42: | NHBoc |

TABLE 20-continued

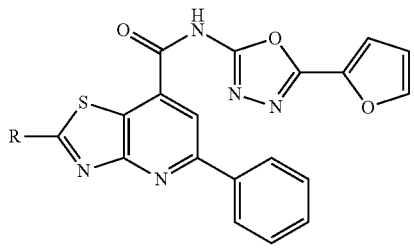

| | |
|---|---|
| Ib-43: | N(Me)Ph |
| Ib-44: | 4-OH-piperidino |
| Ib-45: | 4-Ph-piperidino |
| Ib-46: | 4-piperidino-piperidino |
| Ib-47: | 2,2-Me$_2$-morpholino |
| Ib-48: | (dI)-2-(2-azabicyclo[2.2.1]heptyl) |
| Ib-49: | N(Me)CH$_2$CH$_2$CF$_3$ |
| Ib-50: | NMe$_2$ |
| Ib-51: | NH$_2$ |

TABLE 21

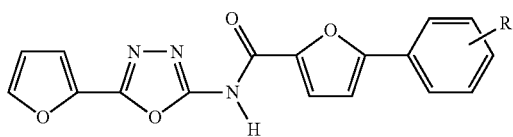

| | | | |
|---|---|---|---|
| Ic-1: | R = H | Ic-2: | R = 2-F |
| Ic-3: | R = 2-NO$_2$ | Ic-4: | R = 3-Cl |
| Ic-5: | R = 3-NO$_2$ | Ic-6: | R = 4-F |
| Ic-7: | R = 4-Cl | Ic-8: | R = 4-OMe |
| Ic-9: | R = 4-NH$_2$ | Ic-10: | R = 4-NHCOCH$_3$ |
| Ic-11: | R = 4-NO$_2$ | Ic-12: | R = 4-COOEt |
| Ic-13: | R = 2-Cl, 4-Cl | Ic-14: | R = 2-Cl, 4-NO$_2$ |
| Ic-15: | R = 2-Me, 4-NH$_2$ | Ic-16: | R = 2-Me, 4-NHCOCH$_3$ |
| Ic-17: | R = 2-Me, 4-NO$_2$ | Ic-18: | R = 2-OMe, 4-NO$_2$ |
| Ic-19: | R = 2-Cl, 5-NO$_2$ | Ic-20: | R = 3-NO$_2$, 4-Cl |
| Ic-21: | R = 3-Cl, 5-Cl | | |

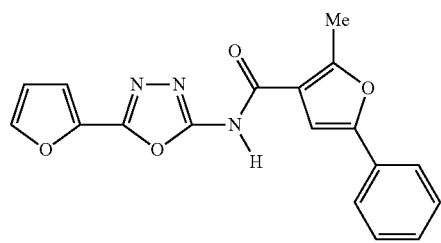 [SMILES: Cc1oc(-c2ccccc2)cc1C(=O)Nc1nnc(-c2ccco2)o1]
Ic-22

TABLE 22

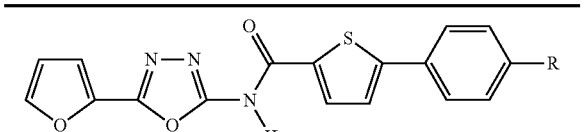

| | |
|---|---|
| Ic-23: | R = H |
| Ic-24: | R = CN |

TABLE 22-continued

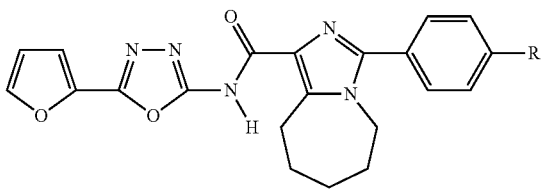

| Ic-25: | R = H |
| Ic-26: | R = F |

TABLE 23

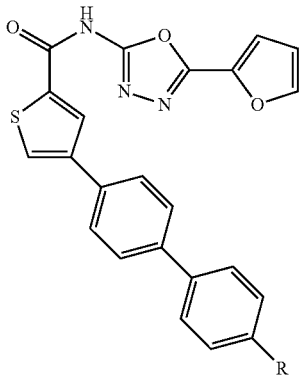

| Ic-27: | H |
| Ic-28: | Et |

TABLE 24

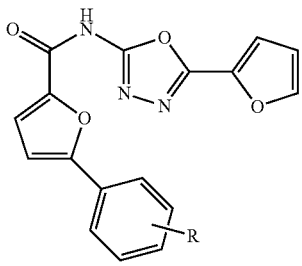

| Ic-29: | 4-COOH |

The compound (I) or the pharmacologically acceptable salt thereof may directly be administered alone and is usually preferably made into various pharmaceutical preparations. The pharmaceutical preparations can be produced by a routine method of pharmaceutics by mixing the active ingredient with one or two or more pharmacologically acceptable carriers.

Examples of an administration route include oral or inhalation administration and parenteral administration such as intravenous administration.

Examples of a dosage form include tablets, inhalants and injections. The tablets can be produced according to a routine method by mixing various additives, for example, lactose, starch, magnesium stearate, hydroxypropylcellulose, polyvinyl alcohol, a surfactant, and glycerin. The inhalants can be produced according to a routine method by adding, for example, lactose. The injections can be produced according to a routine method by adding water, saline, plant oil, a solubilizing agent, a preservative, and the like.

The effective amount of the compound (I) or the pharmacologically acceptable salt thereof and the number of doses thereof differ depending on a dosage form, the age, body weight, and condition of a patient, etc. Usually, 0.001 mg to 5 g, preferably 0.1 mg to 1 g, more preferably 1 to 500 mg is administered once a day or in several divided portions per day to one adult.

Hereinafter, the present invention will be described more specifically with reference to Test Examples, Examples, and the like. However, the technical scope of the present invention is not limited to these examples.

TEST EXAMPLE 1

(STAT3 Transcription Inhibition Test)
The inhibition of STAT3 transcription was evaluated by using STAT3 reporter HeLa stable cell line (Panomics Inc., catalog No. RC0003), a cell line for the reporter gene method, and performing the following method according to the appendix included therein.

STAT3, reporter HeLa stable cell line subcultured and maintained in a Dulbecco's modified Eagle's medium (DMEM) containing 10% fetal bovine serum, 100 units/mL penicillin, and 100 µg/mL streptomycin was inoculated at a concentration of 40000 cells/well to a 96-well plate (white) and attached to the plate by overnight incubation at 37° C. under 5% $CO_2$. After addition of each evaluation compound adjusted to various concentrations (adjusted with a DMSO solution), the cells were precultured for 1 hour. Then, oncostatin M for activating STAT3 was added at a final concentration 10 ng/mL, and the cells were further cultured at 37° C. under 5% $CO_2$ for 4 hours. Luciferase activity derived from the cells was determined using Steady-Glo Luciferase Assay System (Promega Corp.), and STAT3 transcriptional activity scores were calculated according to the following formula:

$$\text{STAT3 transcriptional activity score (\%)} = 100 \times (L_{chem} - L_0)/(L_{DMSO} - L_0)$$

$L_0$: luminescence intensity obtained without stimulation with oncostatin M
$L_{chem}$: luminescence intensity obtained by the addition of a test sample
$L_{DMSO}$: luminescence intensity obtained by the addition of only a solvent for dissolving a test sample The test results were indicated in the rate of inhibition of STAT3 transcription by each compound at a concentration of 100 µM. The results are shown in Table 25.

TABLE 25

| Compoud No. | STAT3 transcription inhibitory activity (%) | Compoud No. | STAT3 transcription inhibitory activity (%) |
| --- | --- | --- | --- |
| Ia-1 | 60 | Ia-77 | 80 |
| Ia-5 | 98 | Ia-78 | 70 |
| Ia-10 | 97 | Ia-81 | 63 |
| Ia-11 | 67 | Ia-82 | 54 |
| Ia-12 | 83 | Ia-83 | 75 |
| Ia-13 | 67 | Ia-84 | 74 |
| Ia-14 | 57 | Ia-87 | 92 |
| Ia-16 | 57 | Ia-90 | 97 |
| Ia-17 | >100 | Ia-99 | 78 |
| Ia-18 | 71 | Ib-1 | >100 |
| Ia-19 | 55 | Ib-2 | 68 |
| Ia-21 | 62 | Ib-3 | >100 |
| Ia-24 | 94 | Ib-4 | >100 |
| Ia-25 | 70 | Ib-19 | 90 |
| Ia-29 | 81 | Ib-26 | 60 |

TABLE 25-continued

| Compoud No. | STAT3 transcription inhibitory activity (%) | Compoud No. | STAT3 transcription inhibitory activity (%) |
|---|---|---|---|
| Ia-33 | 90 | Ib-27 | 67 |
| Ia-34 | 78 | Ib-30 | >100 |
| Ia-42 | 88 | Ib-32 | 80 |
| Ia-43 | 74 | Ic-4 | 81 |
| Ia-44 | 58 | Ic-12 | 73 |
| Ia-47 | 58 | Ic-14 | 51 |
| Ia-50 | >100 | Ic-19 | 56 |
| Ia-52 | 71 | Ic-21 | 64 |
| Ia-56 | 87 | Ic-22 | 65 |
| Ia-62 | 76 | Ic-26 | 58 |
| Ia-66 | 58 | | |
| Ia-69 | 53 | | |
| Ia-76 | 69 | | |

TEST EXAMPLE 2

(MDA-MB-468 Cell Growth Inhibitory Activity)

MDA-MB-468 diluted with phenol red-free DMEM/F-12 (GIBCO; 10% FBS, 20 units/ml penicillin/streptomycin) was inoculated at a concentration of 2000 cells/well to a 96-well plate (Greiner Bio-One) and cultured overnight at 37° C. in the presence of 5% $CO_2$. Then, a test sample solution (containing 2 (v/v)% DMSO) adjusted to 10 µM was added thereto at a concentration of 10 µL/well and contacted with the cells at 37° C. for 72 hours in the presence of 5% $CO_2$. Each well was washed three times with a medium. Then, after addition of 100 µL/well of a medium and 20 µL/well of CellTiter 96 $AQ_{ueous}$, One Solution Reagent (Promega Corp.), the cells were incubated at 37° C. for 2 hours in the presence of 5% $CO_2$. Absorbance at 495 nm was measured using Multiplate reader (Molecular Devices, Inc.), and the rate of inhibition of cell growth was calculated according to the following formula:

Rate of inhibition of cell growth (%)=100−100×(Abs$_{chem}$−bkgd)/(Abs$_{DMSO}$−bkgd)

Abs$_{chem}$: absorbance obtained by the addition of a test sample

Abs$_{DMSO}$: absorbance obtained by the addition of only a solvent for test sample dissolution bkgd: absorbance obtained by the addition of CellTiter 96 $AQ_{ueous}$ One Solution Reagent to a medium for cell culture The test results were indicated in the rate of inhibition of cell growth by each compound at a concentration of 20 µM. The results are shown in Table 26.

TABLE 26

| Compound No. | Cell growth inhibitory activity (%) | Compound No. | Cell growth inhibitory activity (%) |
|---|---|---|---|
| Ia-5 | 88 | Ia-78 | 64 |
| Ia-12 | 61 | Ia-81 | 78 |
| Ia-17 | 54 | Ia-82 | 75 |
| Ia-19 | 94 | Ia-83 | 71 |
| Ia-21 | 91 | Ia-84 | 68 |
| Ia-24 | 97 | Ia-99 | 55 |
| Ia-29 | 87 | Ib-1 | 96 |
| Ia-33 | 98 | Ib-2 | >100 |
| Ia-47 | 53 | Ib-3 | >100 |
| Ia-50 | 51 | Ib-4 | 78 |
| Ia-52 | 91 | Ib-19 | 83 |
| Ia-56 | 61 | Ib-26 | 76 |
| Ia-62 | 71 | Ib-27 | 82 |
| Ia-66 | 59 | Ib-30 | 84 |

TABLE 26-continued

| Compound No. | Cell growth inhibitory activity (%) | Compound No. | Cell growth inhibitory activity (%) |
|---|---|---|---|
| Ia-69 | 69 | Ib-32 | 86 |
| Ia-76 | 72 | Ic-18 | 76 |
| Ia-77 | 76 | | |

TEST EXAMPLE 3

(SCC-3 Cell Growth Inhibition Test)

Human lymphoma SCC-3 cells purchased from Japan Health Sciences Foundation were cultured for 4 days at a density of 5000 cells/well in a 96-well plate with RPMI1640 (Sigma-Aldrich Corp.) containing 10% fetal bovine serum (FBS; GIBCO) as a culture medium.

Simultaneously with cell inoculation, each test compound diluted to various concentrations with an RPMI medium was added to each well. After 72-hour culture, cell growth inhibitory activity was determined by the MTT method (J. Immunol. Methods, 1993, 65, 581-593) using a microplate reader (NJ-2300, BioTek Instruments, Inc.).

The test results were indicated in a concentration ($IC_{50}$) at which 50% cell growth was inhibited.

The results are shown in Table 27.

TABLE 27

| Compound No. | $IC_{50}$ (µM) |
|---|---|
| Ia-11 | 1.8 |
| Ia-13 | 1.0 |
| Ia-17 | 4.0 |
| Ia-18 | 1.9 |
| Ia-21 | 1.7 |
| Ia-25 | 53 |
| Ia-43 | 1.8 |
| Ia-44 | 1.8 |
| Ia-50 | 1.1 |
| Ia-76 | 0.2 |
| Ia-78 | <0.1 |
| Ia-83 | <0.1 |
| Ia-84 | <0.1 |
| Ia-87 | 0.6 |
| Ib-1 | 0.52 |
| Ib-4 | 0.7 |
| Ic-18 | 16 |

TEST EXAMPLE 4

Evaluation using Human Lymphoma-Transplanted Nude Mice $1\times10^6$ human lymphoma SCC-3 cells (containing Matrigel) were subcutaneously transplanted to the flank part of each 6-week-old male nude mouse (BALB/cA-nu/nu, CLEA Japan, Inc.). After the transplantation, the tumor volumes [major axis (mm) and minor axis (mm)] of the SCC-3 cancer-bearing mice were measured using an electronic vernier caliper (CD-10, Mitutoyo Corp.), and tumor volumes [$mm^3$: (major axis)×(minor axis)$^2$/2] were calculated. SCC-3 cancer-bearing mice whose tumor volume reached 50 to 300 $mm^3$ were selected and divided based on the tumor volumes into groups each containing 5 individuals. A test compound was suspended in a 0.5% methylcellulose solution and orally administered at a dose of 0.01 mL/g body weight once a day for 5 days (Day 0 (administration initiation day) to Day 4). To a control group, none was administered. The tumor volumes of the SCC-3 cancer-bearing mice were measured every day from the initiation of test compound administration to evaluate antitumor effect. The antitumor effect was assessed by calculating T/C (%) values according to the following formula:

V: tumor volume on every assay day
V0: tumor volume on the administration initiation day (V/V0 of the test compound group)/(V/V0 of the control group)×100

Validity determination criteria for this system adopted the method of Inaba, et al. (Cancer, 1989, 64, 1577-1582).
The results are shown in Table 28.

TABLE 28

| Compound No. | Dose/time (mg/kg) | Day after administration (day) | T/C (%) | Significant difference |
|---|---|---|---|---|
| Control group | | | 100 | |
| Ia-14 | 80 | 11 | 57 | $p < 0.05$ |
| Ia-23 | 80 | 6 | 55 | $p < 0.05$ |
| Ib-1 | 80 | 18 | 52 | $p < 0.05$ |

EXAMPLE 1

N-[5-(2-Furyl)-1,3,4-oxadiazol-2-yl]-3-biphenylcarboxamide (compound Ia-1)

The title compound was synthesized in accordance with the synthesis method of compound Ic-2 described below, using an acid chloride which can be prepared from commercially available 3-biphenylcarboxylic acid by a routine method instead of 5-(2-fluorophenyl)-2-furancarbonyl chloride.

$^1$H-NMR (500M Hz, DMSO-$d_6$) δ: 12.34 (1H, brs), 8.35 (1H, s), 8.07 (1H, d, J=1.7 Hz), 7.99 (1H, m), 7.81 (2H, d, J=7.3 Hz), 7.67 (2H, t, J=7.6 Hz), 7.53 (1H, m), 7.45-7.42 (2H, m), 7.31 (1H, d, J=3.7 Hz), 6.81 (1H, dd, J=3.7 Hz, 1.7 Hz).
ES-MS (m/z): 332 (M+H)$^+$.

The following compounds Ia-2 to Ia-7 were synthesized in accordance with the synthesis method of compound Ia-50 described below, using commercially available corresponding boronic acid or boronic acid pinacol ester instead of 1-methyl-5-indoleboronic acid pinacol ester.

EXAMPLE 2

N-[5-(2-Furyl)-1,3,4-oxadiazol-2-yl]-2'-hydroxy-3-biphenylcarboxamide (Compound Ia-2)

$^1$H-NMR (500M Hz, DMSO-$d_6$) δ: 12.22 (1H, br), 9.65 (1H, s), 8.20 (1H, s), 8.03 (1H, s), 7.95 (1H, d, J=7.8 Hz), 7.82 (1H, d, J=7.8 Hz), 7.55 (1H, t, J=7.8 Hz), 7.36 (1H, d, J=7.3 Hz), 7.26 (1H, d, J=3.4 Hz), 7.20 (1H, m), 6.98-6.89 (2H, m), 6.78 (1H, dd, J=3.4 Hz, 1.5 Hz).
ES-MS (m/z): 348 (M+H)$^+$.

EXAMPLE 3

2'-Formyl-N-[5-(2-furyl)-1,3,4-oxadiazol-2-yl]-3-biphenylcarboxamide (Compound Ia-3)

ES-MS (m/z): 360 (M+H)$^+$.

EXAMPLE 4

N-[5-(2-Furyl)-1,3,4-oxadiazol-2-yl]-3'-hydroxy-3-biphenylcarboxamide (Compound Ia-4)

$^1$H-NMR (500M Hz, DMSO-$d_6$) δ: 12.34 (1H, br), 9.60 (1H, s), 8.30 (1H, s), 8.05 (1H, d, J=1.0 Hz), 8.00 (1H, d, J=7.8 Hz), 7.88 (1H, d, J=7.8 Hz), 7.62 (1H, t, J=7.8 Hz), 7.33-7.27 (2H, m), 7.23-7.16 (2H, m), 6.84-6.79 (2H, m).
ES-MS (m/z): 348 (M+H)$^+$.

EXAMPLE 5

N-[5-(2-Furyl)-1,3,4-oxadiazol-2-yl]-3'-nitro-3-biphenylcarboxamide (Compound Ia-5)

$^1$H-NMR (500M Hz, DMSO-$d_6$) δ: 12.41 (1H, br), 8.65 (1H, s), 8.45 (1H, s), 8.31-8.29 (2H, m), 8.12 (1H, d, J=7.4 Hz), 8.08 (1H, s), 8.07 (1H, d, J=7.4 Hz), 7.84 (1H, t, J=7.9 Hz), 7.74 (1H, t, J=7.4 Hz), 7.31 (1H, d, J=3.4 Hz), 6.82 (1H, dd, J=3.4 Hz, 1.7 Hz).
ES-MS (m/z): 377 (M+H)$^+$.

EXAMPLE 6

3'-Formyl-N-[5-(2-furyl)-1,3,4-oxadiazol-2-yl]-3-biphenylcarboxamide (Compound Ia-6)

$^1$H-NMR (500M Hz, DMSO-$d_6$, @80° C.) δ: 10.13 (1H, s), 8.40 (1H, s), 8.29 (1H, s), 8.10 (1H, d, J=7.8 Hz), 8.06-7.94 (4H, m), 7.76-7.66 (2H, m), 7.24 (1H, d, J=3.4 Hz), 6.76 (1H, dd, J=3.4 Hz, 2.0 Hz).
ES-MS (m/z): 360 (M+H)$^+$.

EXAMPLE 7

N-[5-(2-Furyl)-1,3,4-oxadiazol-2-yl]-3'-methoxycarbonyl-3-biphenylcarboxamide (Compound Ia-7)

$^1$H-NMR (500M Hz, DMSO-$d_6$) δ: 12.40 (1H, br), 8.38 (1H, s), 8.36 (1H, s), 8.10 (1H, d, J=7.4 Hz), 8.08-8.02 (4H, m), 7.73-7.69 (2H, m), 7.31 (1H, d, J=3.4 Hz), 6.82 (1H, d, J=1.7 Hz), 3.92 (3H, s).
ES-MS (m/z): 390 (M+H)$^+$.

EXAMPLE 8

3'-Carboxy-N-[5-(2-furyl)-1,3,4-oxadiazol-2-yl]-3-biphenylcarboxamide (Compound Ia-8)

The title compound was prepared by hydrolyzing compound Ia-7 using an aqueous sodium hydroxide solution in accordance with a routine method.

$^1$H-NMR (500M Hz, DMSO-$d_6$, @60° C.) δ: 8.41 (1H, s), 8.30 (1H, s), 8.08 (1H, d, J=7.8 Hz), 8.03-7.93 (4H, m), 7.66-7.62 (2H, m), 7.21 (1H, d, J=3.4 Hz), 6.76 (1H, dd, J=3.4 Hz, 2.0 Hz).
ES-MS (m/z): 376 (M+H)$^+$.

The following compounds Ia-9 to Ia-30 were synthesized in accordance with the synthesis method of compound Ia-50 described below, using commercially available corresponding boronic acid or boronic acid pinacol ester instead of 1-methyl-5-indoleboronic acid pinacol ester.

EXAMPLE 9

3'-Cyano-N-[5-(2-furyl)-1,3,4-oxadiazol-2-yl]-3-biphenylcarboxamide (Compound Ia-9)

$^1$H-NMR (500M Hz, DMSO-$d_6$, @80° C.) δ: 8.38 (1H, s), 8.22 (1H, s), 8.12-7.92 (4H, m), 7.84 (1H, d, J=7.8 Hz), 7.73-7.65 (2H, m), 7.23 (1H, d, J=2.9 Hz), 6.75 (1H, d, J=2.0 Hz).
ES-MS (m/z): 357 (M+H)$^+$.

EXAMPLE 10

4'-Fluoro-N-[5-(2-furyl)-1,3,4-oxadiazol-2-yl]-3-biphenylcarboxamide (Compound Ia-10)

$^1$H NMR (500M Hz, DMSO-$d_6$, @100° C.) δ: 8.32 (1H, s), 8.03 (1H, d, J=7.3 Hz), 7.93 (1H, s), 7.84-7.75 (3H, m), 7.58 (1H, brm), 7.30-7.18 (3H, m), 6.74 (1H, dd, J=3.4 Hz, 2.0 Hz).
ES-MS (m/z): 350 (M+H)$^+$.

EXAMPLE 11

4'-Chloro-N-[5-(2-furyl)-1,3,4-oxadiazol-2-yl]-3-biphenylcarboxamide (Compound Ia-11)

$^1$H NMR (500M Hz, DMSO-$d_6$) δ: 8.35 (1H, s), 8.07 (1H, s), 8.03-7.98 (2H, m), 7.85 (2H, d, J=8.5 Hz), 7.67 (1H, t, J=7.9 Hz), 7.60 (2H, d, J=8.5 Hz), 7.30 (1H, d, J=3.4 Hz), 6.81 (1H, dd, J=3.4 Hz, 1.7 Hz).
ES-MS (m/z): 368 ($^{37}$Cl M+H)$^+$, 366 ($^{35}$Cl M+H)$^+$.

EXAMPLE 12

N-[5-(2-Furyl)-1,3,4-oxadiazol-2-yl]-4'-methyl-3-biphenylcarboxamide (Compound Ia-12)

$^1$H-NMR (500M Hz, DMSO-$d_6$, @100° C.) δ: 8.38 (1H, br), 8.09 (1H, br), 7.86 (1H, br), 7.70 (1H, br), 7.54-7.47 (2H, br), 7.25 (3H, br), 7.07 (1H, br), 6.69 (1H, br), 2.49 (3H, brs).
ES-MS (m/z): 346 (M+H)$^+$.

EXAMPLE 13

N-[5-(2-Furyl)-1,3,4-oxadiazol-2-yl]-4'-vinyl-3-biphenylcarboxamide (Compound Ia-13)

$^1$H NMR (500M Hz, DMSO-$d_6$) δ: 12.37 (1H, br), 8.37 (1H, s), 8.07 (1H, d, J=1.7 Hz), 8.01-7.98 (2H, m), 7.81 (2H, d, J=7.9 Hz), 7.67-7.63 (3H, m), 7.30 (1H, d, J=3.4 Hz), 6.85-6.79 (3H, m), 5.94 (1H, d, J=17 Hz), 5.34 (1H, d, J=11 Hz).
ES-MS (m/z): 358 (M+H)$^+$.

EXAMPLE 14

4'-tert-Butyl-N-[5-(2-furyl)-1,3,4-oxadiazol-2-yl]-3-biphenylcarboxamide (Compound Ia-14)

$^1$H-NMR (500M Hz, DMSO-$d_6$, @100° C.) δ: 8.36 (1H, s), 8.05 (1H, d, J=6.8 Hz), 7.91 (1H, s), 7.79 (1H, brs), 7.62 (2H, brs), 7.52-7.49 (3H, brm), 7.14 (1H, d, J=3.4 Hz), 6.72 (1H, brs), 1.35 (9H, s).
ES-MS (m/z): 388 (M+H)$^+$.

EXAMPLE 15

N-[5-(2-Furyl)-1,3,4-oxadiazol-2-yl]-4'-hydroxy-3-biphenylcarboxamide (Compound Ia-15)

$^1$H-NMR (500M Hz, DMSO-$d_6$) δ: 9.63 (1H, s), 8.28 (1H, s), 8.03 (1H, brs), 7.94 (1H, t, J=7.8 Hz), 7.82 (1H, m), 7.60 (2H, d, J=8.3 Hz), 7.45 (1H, brm), 7.25 (1H, brd, J=2.9 Hz), 6.89 (2H, d, J=8.3 Hz), 6.79 (1H, br).
ES-MS (m/z): 348 (M+H)$^+$.

EXAMPLE 16

N-[5-(2-Furyl)-1,3,4-oxadiazol-2-yl]-4'-methoxy-3-biphenylcarboxamide (Compound Ia-16)

$^1$H-NMR (500M Hz, DMSO-$d_6$) δ: 12.31 (1H, brs), 8.30 (1H, s), 8.07 (1H, d, J=1.7 Hz), 7.94-7.93 (2H, m), 7.76 (2H, d, J=8.5 Hz), 7.63 (1H, t, J=7.9 Hz), 7.31 (1H, d, J=3.4 Hz), 7.09 (2H, d, J=8.5 Hz), 6.82 (1H, dd, J=3.4 Hz, 1.7 Hz), 3.83 (3H, s).
ES-MS (m/z): 362 (M+H)$^+$.

EXAMPLE 17

4'-Formyl-N-[5-(2-furyl)-1,3,4-oxadiazol-2-yl]-3-biphenylcarboxamide (Compound Ia-17)

$^1$H-NMR (500M Hz, DMSO-$d_6$) δ: 12.39 (1H, br), 10.10 (1H, s), 8.45 (1H, s), 8.10-8.07 (7H, m), 7.73 (1H, t, J=7.9 Hz), 7.31 (1H, d, J=3.4 Hz), 6.82 (1H, dd, J=3.4 Hz, 1.7 Hz).
ES-MS (m/z): 360 (M+H)$^+$.

EXAMPLE 18

4'-Acetyl-N-[5-(2-furyl)-1,3,4-oxadiazol-2-yl]-3-biphenylcarboxamide (Compound Ia-18)

$^1$H-NMR (500M Hz, DMSO-$d_6$) δ: 12.37 (1H, br), 8.42 (1H, s), 8.11-8.05 (5H, m), 7.97 (2H, d, J=8.3 Hz), 7.71 (1H, t, J=7.3 Hz), 7.30 (1H, d, J=3.4 Hz), 6.81 (1H, dd, J=3.4 Hz, 1.5 Hz), 2.64 (3H, s).
ES-MS (m/z): 374 (M+H)$^+$.

EXAMPLE 19

4'-Benzoyl-N-[5-(2-furyl)-1,3,4-oxadiazol-2-yl]-3-biphenylcarboxamide (Compound Ia-19)

$^1$H-NMR (500M Hz, DMSO-$d_6$) δ: 12.43 (1H, br), 8.47 (1H, s), 8.10-7.99 (5H, m), 7.89 (2H, d, J=8.5 Hz), 7.81-7.69 (4H, m), 7.62-7.59 (2H, m), 7.27 (1H, d, J=3.4 Hz), 6.80 (1H, dd, J=3.4 Hz, 1.7 Hz).
ES-MS (m/z): 436 (M+H)$^+$.

EXAMPLE 20

4'-Carbamoyl-N-[5-(2-furyl)-1,3,4-oxadiazol-2-yl]-3-biphenylcarboxamide (Compound Ia-20)

$^1$H-NMR (500M Hz, DMSO-$d_6$) δ: 12.35 (1H, br), 8.42 (1H, brs), 8.07-8.02 (6H, m), 7.91 (2H, d, J=7.3 Hz), 7.69 (1H, t, J=7.3 Hz), 7.44 (1H, brs), 7.31 (1H, brs), 6.81 (1H, dd, J=3.4 Hz, 2.0 Hz).
ES-MS (m/z): 375 (M+H)$^+$.

EXAMPLE 21

4'-Cyano-N-[5-(2-furyl)-1,3,4-oxadiazol-2-yl]-3-biphenylcarboxamide (Compound Ia-21)

$^1$H-NMR (500M Hz, DMSO-d$_6$) δ: 12.38 (1H, br), 8.43 (1H, s), 8.07 (1H, d, J=1.7 Hz), 8.05-7.99 (6H, m), 7.72 (1H, t, J=7.9 Hz), 7.31 (1H, d, J=3.4 Hz), 6.82 (1H, dd, J=3.4 Hz, 1.7 Hz).
ES-MS (m/z): 357 (M+H)$^+$.

EXAMPLE 22

4'-Cyanomethyl-N-[5-(2-furyl)-1,3,4-oxadiazol-2-yl]-3-biphenylcarboxamide (Compound Ia-22)

$^1$H-NMR (500M Hz, DMSO-d$_6$) δ: 8.39 (1H, s), 8.10-7.95 (2H, m), 7.85 (1H, s), 7.80-7.75 (2H, m), 7.65-7.45 (2H, m), 7.31-7.19 (2H, m), 6.77 (1H, s), 4.10 (2H, s). ES-MS (m/z): 371 (M+H)$^+$.

EXAMPLE 23

4'-n-Butoxycarbonyl-N-[5-(2-furyl)-1,3,4-oxadiazol-2-yl]-3-biphenylcarboxamide (Compound Ia-23)

$^1$H-NMR (500M Hz, DMSO-d$_6$, @80° C.) δ: 8.45 (1H, brs), 8.18 (1H, d, J=6.8 Hz), 8.00 (2H, d, J=6.8 Hz), 7.89 (1H, s), 7.82-7.75 (3H, m), 7.53 (1H, t, J=7.4 Hz), 7.11 (1H, brs), 6.71 (1H, brs), 4.32 (2H, t, J=6.8 Hz), 1.74 (2H, m), 1.47 (2H, m), 0.98 (3H, t, J=7.4 Hz).
ES-MS (m/z): 432 (M+H)$^+$.

EXAMPLE 24

N-[5-(2-Furyl)-1,3,4-oxadiazol-2-yl]-4'-nitro-3-biphenylcarboxamide (Compound Ia-24)

$^1$H-NMR (500M Hz, DMSO-d$_6$) δ: 8.48 (1H, s), 8.32 (2H, d, J=8.5 Hz), 8.17 (1H, d, J=7.4 Hz), 8.02-7.95 (4H, m), 7.63 (1H, t, J=7.4 Hz), 7.18 (1H, d, J=3.4 Hz), 6.76 (1H, s).
ES-MS (m/z): 377 (M+H)$^+$.

EXAMPLE 25

N-[5-(2-Furyl)-1,3,4-oxadiazol-2-yl]-4'-sulfamoyl-3-biphenylcarboxamide (Compound Ia-25)

$^1$H-NMR (500M Hz, DMSO-d$_6$) δ: 8.41 (1H, brs), 8.12 (1H, d, J=7.8 Hz), 7.94-7.88 (5H, m), 7.73 (1H, d, J=7.8 Hz), 7.48 (1H, t, J=7.8 Hz), 7.41 (2H, brs), 6.96 (1H, d, J=3.4 Hz), 6.69 (1H, dd, J=3.4 Hz, 1.5 Hz).
ES-MS (m/z): 411 (M+H)$^+$.

EXAMPLE 26

N-[5-(2-Furyl)-1,3,4-oxadiazol-2-yl]-4'-(N-methylsulfamoyl)-3-biphenylcarboxamide (Compound Ia-26)

$^1$H-NMR (500M Hz, DMSO-d$_6$) δ: 8.44 (1H, brs), 8.11 (1H, d, J=7.3 Hz), 8.02-7.97 (3H, m), 7.91-7.84 (3H, m), 7.65 (1H, t, J=7.8 Hz), 7.53 (1H, m), 7.22 (1H, brs), 6.78 (1H, brd, J=2.0 Hz), 2.46 (3H, d, J=4.9 Hz).
ES-MS (m/z): 425 (M+H)$^+$.

EXAMPLE 27

N-[5-(2-Furyl)-1,3,4-oxadiazol-2-yl]-4'-(N,N-dimethylsulfamoyl)-3-biphenylcarboxamide (Compound Ia-27)

$^1$H-NMR (500M Hz, DMSO-d$_6$) δ: 12.39 (1H, br), 8.44 (1H, d, J=1.5 Hz), 8.09-8.07 (5H, m), 7.89 (2H, d, J=8.3 Hz), 7.73 (1H, m), 7.30 (1H, d, J=3.9 Hz), 6.81 (1H, dd, J=3.9 Hz, 1.5 Hz), 2.67 (6H, s).
ES-MS (m/z): 439 (M+H)$^+$.

EXAMPLE 28

N-[5-(2-Furyl)-1,3,4-oxadiazol-2-yl]-4'-methanesulfonyl-3-biphenylcarboxamide (Compound Ia-28)

$^1$H-NMR (500M Hz, DMSO-d$_6$) δ: 12.38 (1H, br), 8.43 (1H, s), 8.08-8.07 (7H, m), 7.73 (1H, t, J=7.8 Hz), 7.30 (1H, d, J=2.9 Hz), 6.82 (1H, dd, J=4.9 Hz, 2.9 Hz), 3.29 (3H, s).
ES-MS (m/z): 410 (M+H)$^+$.

EXAMPLE 29

4'-Cyano-N-[5-(2-furyl)-1,3,4-oxadiazol-2-yl]-2'-methyl-3-biphenylcarboxamide (Compound Ia-29)

$^1$H-NMR (500M Hz, DMSO-d$_6$) δ: 12.31 (1H, br), 8.07 (1H, d, J=6.8 Hz), 8.03 (1H, s), 8.03 (1H, s), 7.84 (1H, s), 7.77 (1H, d, J=7.9 Hz), 7.66-7.64 (2H, m), 7.49 (1H, t, J=7.9 Hz), 7.25 (1H, d, J=3.4 Hz), 6.78 (1H, dd, J=3.4 Hz, 1.7 Hz), 2.29 (3H, s).
ES-MS (m/z): 371 (M+H)$^+$.

EXAMPLE 30

4'-Acetyl-3'-fluoro-N-[5-(2-furyl)-1,3,4-oxadiazol-2-yl]-3-biphenylcarboxamide (Compound Ia-30)

$^1$H-NMR (500M Hz, DMSO-d$_6$, @100° C.) δ: 8.43 (1H, brs), 8.14 (1H, brd, J=6.3 Hz), 7.90 (3H, br), 7.64-7.59 (3H, brm), 7.14 (1H, brs), 6.72 (1H, brs), 2.61 (3H, s).
ES-MS (m/z): 392 (M+H)$^+$.

EXAMPLE 31

N-[5-(2-Furyl)-1,3,4-oxadiazol-2-yl]-4'-sulfamoyl-4-biphenylcarboxamide (Compound Ia-31)

The title compound was synthesized in accordance with the synthesis method of compound Ia-50 described below, using N-[5-(2-furyl)-1,3,4-oxadiazol-2-yl]-4-iodobenzenecarboxamide prepared in Reference Example 1 instead of N-[5-(2-furyl)-1,3,4-oxadiazol-2-yl]-3-iodobenzenecarboxamide and using commercially available 4-sulfamoylphenylboronic acid pinacol ester instead of 1-methyl-5-indoleboronic acid pinacol ester.
ES-MS (m/z): 411 (M+H)$^+$.

The following compounds Ia-32 to Ia-35 were synthesized in accordance with the synthesis method of compound Ia-50 described below, using commercially available corresponding boronic acid or boronic acid pinacol ester instead of 1-methyl-5-indoleboronic acid pinacol ester.

EXAMPLE 32

N-[5-(2-Furyl)-1,3,4-oxadiazol-2-yl]-3-(1-naphthyl)benzenecarboxamide (Compound Ia-32)

$^1$H-NMR (500M Hz, DMSO-$d_6$) δ: 12.30 (1H, brs), 8.17 (1H, s), 8.13 (1H, d, J=7.4 Hz), 8.06-8.02 (3H, m), 7.83-7.80 (2H, m), 7.75 (1H, t, J=7.4 Hz), 7.66-7.50 (4H, m), 7.30 (1H, d, J=3.4 Hz), 6.81 (1H, dd, J=3.4 Hz, 1.7 Hz).
ES-MS (m/z): 382 (M+H)$^+$.

EXAMPLE 33

N-[5-(2-Furyl)-1,3,4-oxadiazol-2-yl]-3-(2-naphthyl)benzenecarboxamide (Compound Ia-33)

$^1$H-NMR (500M Hz, DMSO-$d_6$) δ: 8.51 (1H, s), 8.37 (1H, s), 8.14 (1H, d, J=7.9 Hz), 8.09-8.04 (4H, m), 8.00-7.99 (2H, m), 7.73 (1H, t, J=7.9 Hz), 7.61-7.55 (2H, m), 7.32 (1H, d, J=3.4 Hz), 6.82 (1H, dd, J=3.4 Hz, 1.7 Hz).
ES-MS (m/z): 382 (M+H)$^+$.

EXAMPLE 34

N-[5-(2-Furyl)-1,3,4-oxadiazol-2-yl]-3-(5-methyl-2-furyl)benzenecarboxamide (Compound Ia-34)

$^1$H-NMR (500M Hz, DMSO-$d_6$) δ: 12.28 (1H, br), 8.29 (1H, s), 8.08 (1H, s), 7.92 (1H, d, J=7.9 Hz), 7.88 (1H, d, J=7.9 Hz), 7.59 (1H, t, J=7.9 Hz), 7.31 (1H, d, J=3.4 Hz), 6.97 (1H, d, J=3.4 Hz), 6.82 (1H, dd, J=3.4 Hz, 1.7 Hz), 6.27 (1H, d, J=3.4 Hz), 2.39 (3H, s).
ES-MS (m/z): 336 (M+H)$^+$.

EXAMPLE 35

3-(2-Cyano-5-pyridyl)-N-[5-(2-furyl)-1,3,4-oxadiazol-2-yl]benzenecarboxamide (Compound Ia-35)

ES-MS (m/z): 358 (M+H)$^+$.

EXAMPLE 36

N-[5-(2-Furyl)-1,3,4-oxadiazol-2-yl]-3-(5-sulfamoyl-2-thienyl)benzenecarboxamide (Compound Ia-36)

The title compound was synthesized in accordance with the synthesis method of compound Ic-2 described below, using an acid chloride which can be prepared from 3-(5-sulfamoyl-2-thienyl)benzoic acid described in Reference Example 2 by a routine method instead of 5-(2-fluorophenyl)-2-furancarbonyl chloride.

$^1$H-NMR (500M Hz, DMSO-$d_6$, @100° C.) δ: 8.33 (1H, brs), 8.03 (1H, d, J=7.8 Hz), 7.96-7.91 (2H, m), 7.63-7.50 (3H, m), 7.20 (1H, brs), 6.75 (1H, brs).
ES-MS (m/z): 417 (M+H)$^+$.

The following compounds Ia-37 to Ia-42 were synthesized in accordance with the synthesis method of compound Ia-50 described below, using commercially available corresponding boronic acid or boronic acid pinacol ester instead of 1-methyl-5-indoleboronic acid pinacol ester.

EXAMPLE 37

N-[5-(2-Furyl)-1,3,4-oxadiazol-2-yl]-3-(3-pyridyl)benzenecarboxamide trifluoroacetate (Compound Ia-37)

$^1$H-NMR (500M Hz, DMSO-$d_6$) δ: 12.37 (1H, br), 9.14 (1H, d, J=1.7 Hz), 8.74 (1H, dd, J=5.1 Hz, 1.1 Hz), 8.45 (2H, brs), 8.11-8.08 (3H, m), 7.76-7.73 (2H, m), 7.31 (1H, d, J=3.4 Hz), 6.83 (1H, d, J=1.7 Hz).
ES-MS (m/z): 333 (M+H)$^+$.

EXAMPLE 38

N-[5-(2-Furyl)-1,3,4-oxadiazol-2-yl]-3-(2-hydroxy-5-pyridyl)benzenecarboxamide (Compound Ia-38)

ES-MS (m/z): 349 (M+H)$^+$.

EXAMPLE 39

3-(2-Amino-5-pyridyl)-N-[5-(2-furyl)-1,3,4-oxadiazol-2-yl]benzenecarboxamide (Compound Ia-39)

$^1$H-NMR (500M Hz, DMSO-$d_6$) δ: 12.31 (1H, br), 8.40 (1H, d, J=2.0 Hz), 8.34 (1H, d, J=8.8 Hz), 8.30 (1H, s), 8.07 (1H, s), 8.02-7.96 (4H, m), 7.68 (1H, t, J=7.8 Hz), 7.30 (1H, d, J=3.4 Hz), 7.06 (1H, d, J=8.8 Hz), 6.81 (1H, dd, J=3.4 Hz, 1.5 Hz).
ES-MS (m/z): 348 (M+H)$^+$.

EXAMPLE 40

N-[5-(2-Furyl)-1,3,4-oxadiazol-2-yl]-3-(2-methylthio-5-pyridyl)benzenecarboxamide (Compound Ia-40)

$^1$H-NMR (500M Hz, DMSO-$d_6$) δ: 8.83 (1H, s), 8.39 (1H, s), 8.08 (1H, d, J=7.9 Hz), 8.03-8.01 (2H, m), 7.92 (1H, d, J=7.4 Hz), 7.61 (1H, t, J=7.9 Hz), 7.41 (1H, d, J=8.5 Hz), 7.22 (1H, d, J=3.4 Hz), 6.77 (1H, dd, J=3.4 Hz, 1.7 Hz), 2.57 (3H, s).
ES-MS (m/z): 379 (M+H)$^+$.

EXAMPLE 41

N-[5-(2-Furyl)-1,3,4-oxadiazol-2-yl]-3-(4-pyridyl)benzenecarboxamide (Compound Ia-41)

$^1$H-NMR (500M Hz, DMSO-$d_6$) δ: 12.40 (1H, br), 8.80 (2H, brs), 8.51 (1H, s), 8.18-8.13 (2H, m), 8.07 (1H, d, J=1.5 Hz), 8.01 (2H, d, J=5.9 Hz), 7.76 (1H, t, J=7.8 Hz), 7.31 (1H, d, J=3.4 Hz), 6.82 (1H, dd, J=3.4 Hz, 1.5 Hz).
ES-MS (m/z): 333 (M+H)$^+$.

EXAMPLE 42

N-[5-(2-Furyl)-1,3,4-oxadiazol-2-yl]-3-(3,4-methylenedioxyphenyl)benzenecarboxamide (Compound Ia-42)

$^1$H-NMR (500M Hz, DMSO-$d_6$, @100° C.) δ: 8.27 (1H, br), 7.99 (1H, br), 7.91 (1H, br), 7.79 (1H, br), 7.53 (1H, br), 7.26-7.18 (3H, br), 6.98 (1H, br), 6.72 (1H, br), 6.04 (2H, brs).
ES-MS (m/z): 376 (M+H)$^+$.

The following compounds Ia-43 to Ia-49 were synthesized in accordance with the synthesis method of compound Ia-50 described below, using commercially available corresponding boronic acid or boronic acid pinacol ester instead of 1-methyl-5-indoleboronic acid pinacol ester.

EXAMPLE 43

N-[5-(2-Furyl)-1,3,4-oxadiazol-2-yl]-3-(1-methyl-6-indolyl)benzenecarboxamide (Compound Ia-43)

ES-MS (m/z): 385 (M+H)$^+$.

EXAMPLE 44

N-[5-(2-Furyl)-1,3,4-oxadiazol-2-yl]-3-(1-methyl-5-indolinyl)benzenecarboxamide (Compound Ia-44)

$^1$H NMR (500M Hz, DMSO-d$_6$) δ: 8.24 (1H, s), 8.06 (1H, s), 7.88-7.84 (2H, m), 7.58-7.47 (3H, m), 7.29 (1H, d, J=3.4 Hz), 6.81 (1H, dd, J=3.4 Hz, 1.7 Hz), 6.62 (1H, d, J=8.5 Hz), 3.336 (2H, t, J=8.5 Hz), 2.98 (2H, t, J=8.5 Hz), 2.77 (3H, s).
ES-MS (m/z): 387 (M+H)$^+$.

EXAMPLE 45

N-[5-(2-Furyl)-1,3,4-oxadiazol-2-yl]-3-(1-methyl-5-indazolyl)benzenecarboxamide (Compound Ia-45)

$^1$H-NMR (500M Hz, DMSO-d$_6$) δ: 8.43 (1H, s), 8.07-8.02 (3H, m), 7.88 (1H, s), 7.82 (1H, d, J=7.3 Hz), 7.71 (1H, d, J=8.3 Hz), 7.64 (1H, d, J=8.3 Hz), 7.52 (1H, t, J=7.8 Hz), 7.12 (1H, d, J=3.4 Hz), 6.70 (1H, dd, J=3.4 Hz, 2.0 Hz), 4.05 (3H, s).
ES-MS (m/z): 386 (M+H)$^+$.

EXAMPLE 46

N-[5-(2-Furyl)-1,3,4-oxadiazol-2-yl]-3-(1-methyl-6-benzimidazolyl)benzenecarboxamide (Compound Ia-46)

$^1$H-NMR (500M Hz, DMSO-d$_6$) δ: 8.44 (1H, s), 8.23 (1H, s), 8.06 (1H, d, J=7.4 Hz), 8.00 (1H, s), 7.94 (1H, d, J=7.4 Hz), 7.91 (1H, s), 7.73 (1H, d, J=7.9 Hz), 7.60-7.58 (2H, m), 7.21 (1H, brs), 6.76 (1H, brs), 3.91 (3H, s).
ES-MS (m/z): 386 (M+H)$^+$.

EXAMPLE 47

3-(5-Benzothienyl)-N-[5-(2-furyl)-1,3,4-oxadiazol-2-yl]benzenecarboxamide (Compound Ia-47)

$^1$H-NMR (500M Hz, DMSO-d$_6$) δ: 8.47 (1H, brs), 8.23 (1H, brs), 8.11 (2H, brs), 7.97-7.73 (4H, m), 7.55 (2H, m), 7.16 (1H, brs), 6.75 (1H, brs).
ES-MS (m/z): 388 (M+H)$^+$.

EXAMPLE 48

3-(5-Benzothiazolyl)-N-[5-(2-furyl)-1,3,4-oxadiazol-2-yl]benzenecarboxamide (Compound Ia-48)

$^1$H-NMR (500M Hz, DMSO-d$_6$) δ: 12.36 (1H, br), 9.47 (1H, s), 8.56 (1H, s), 8.49 (1H, s), 8.31 (1H, d, J=7.9 Hz), 8.10 (1H, d, J=7.3 Hz), 8.05-8.02 (2H, m), 7.94 (1H, d, J=7.9 Hz), 7.69 (1H, t, J=7.9 Hz), 7.29 (1H, d, J=3.4 Hz), 6.80 (1H, dd, J=3.4 Hz, 1.7 Hz).
ES-MS (m/z): 389 (M+H)$^+$.

EXAMPLE 49

N-[5-(2-Furyl)-1,3,4-oxadiazol-2-yl]-3-[9-methyl-3-(9H-carbazolyl)]benzenecarboxamide (Compound Ia-49)

$^1$H-NMR (500M Hz, DMSO-d$_6$, @100° C.) δ: 8.51 (1H, s), 8.43 (1H, s), 8.21 (1H, d, J=7.8 Hz), 8.08 (1H, d, J=7.3 Hz), 7.86 (2H, brs), 7.79 (1H, d, J=8.3 Hz), 7.62 (1H, d, J=8.3 Hz), 7.58-7.46 (3H, m), 7.22 (1H, t, J=7.3 Hz), 7.08 (1H, d, J=3.4 Hz), 6.68 (1H, brs), 3.89 (3H, s).
ES-MS (m/z): 435 (M+H)$^+$.

EXAMPLE 50

N-[5-(2-Furyl)-1,3,4-oxadiazol-2-yl]-3-(1-methyl-5-indolyl)benzenecarboxamide (Compound Ia-50)

Palladium acetate (177 mg, 0.79 mmol), 2-dicyclohexylphosphino-2',4',6'-triisopropylbiphenyl (751 mg, 1.58 mmol), tripotassium phosphate (3.34 g, 15.7 mmol), and 1-methylindole-5-boronic acid pinacol ester (3.04 g, 11.8 mmol) were added to a solution of N-[5-(2-furyl)-1,3,4-oxadiazol-2-yl]-3-iodobenzenecarboxamide (3.00 g, 7.87 mmol) prepared in Reference Example 3 in 1-butanol (75 mL), followed by stirring at 100° C. overnight in an argon atmosphere. The reaction solution was concentrated. A saturated aqueous solution of sodium chloride was added to the residue, followed by extraction with methylene chloride and drying over anhydrous sodium sulfate. The solvent was distilled off, and methanol was added to the residue. The precipitated solid was filtered off. The residue obtained by distilling the solvent off was subjected to purification by silica gel column chromatography and recrystallization from methanol to obtain the title compound (1.10 g, 2.86 mmol) (yield: 36%).
$^1$H-NMR (500M Hz, DMSO-d$_6$) δ: 12.28 (1H, br), 8.37 (1H, s), 8.06 (1H, s), 8.00-7.98 (2H, m), 7.93 (1H, d, J=7.3 Hz), 7.65-7.56 (3H, m), 7.39 (1H, d, J=2.9 Hz), 7.30 (1H, d, J=3.4 Hz), 6.81 (1H, dd, J=3.4 Hz, 1.5 Hz), 6.52 (1H, d, J=2.9 Hz), 3.84 (3H, s).
ES-MS (m/z): 385 (M+H)$^+$.

EXAMPLE 51

2-Fluoro-N-[5-(2-furyl)-1,3,4-oxadiazol-2-yl]-3-(1-methyl-5-indolyl)benzenecarboxamide (Compound Ia-51)

The title compound was synthesized in accordance with the synthesis method of compound Ia-50, using 3-bromo-2-fluoro-N-[5-(2-furyl)-1,3,4-oxadiazol-2-yl]benzenecarboxamide prepared in Reference Example 5 instead of N-[5-(2-furyl)-1,3,4-oxadiazol-2-yl]-3-iodobenzenecarboxamide.
ES-MS (m/z): 403 (M+H)$^+$.

EXAMPLE 52

5-Fluoro-N-[5-(2-furyl)-1,3,4-oxadiazol-2-yl]-3-(1-methyl-5-indolyl)benzenecarboxamide (Compound Ia-52)

The title compound was synthesized in accordance with the synthesis method of compound Ia-50, using 3-bromo-5- fluoro-N-[5-(2-furyl)-1,3,4-oxadiazol-2-yl]benzenecarboxamide prepared in Reference Example 6 instead of N-[5-(2-furyl)-1,3,4-oxadiazol-2-yl]-3-iodobenzenecarboxamide.
ES-MS (m/z): 403 (M+H)$^+$.

EXAMPLE 53

2-Fluoro-N-[5-(2-furyl)-1,3,4-oxadiazol-2-yl]-5-(1-methyl-5-indolyl)benzenecarboxamide (Compound Ia-53)

The title compound was synthesized in accordance with the synthesis method of compound Ia-50, using 5-bromo-2-fluoro-N-[5-(2-furyl)-1,3,4-oxadiazol-2-yl]benzenecarboxamide prepared in Reference Example 7 instead of N-[5-(2-furyl)-1,3,4-oxadiazol-2-yl]-3-iodobenzenecarboxamide.
$^1$H-NMR (500M Hz, DMSO-d$_6$) δ: 8.06 (1H, d, J=1.7 Hz), 8.04 (1H, d, J=7.9 Hz), 7.93-7.91 (2H, m), 7.57-7.52 (2H, m), 7.43 (1H, t, J=9.1 Hz), 7.39 (1H, d, J=2.8 Hz), 7.29 (1H, d, J=3.4 Hz), 6.81 (1H, dd, J=3.4 Hz, 1.7 Hz), 6.51 (1H, d, J=2.8 Hz), 3.84 (3H, s).
ES-MS (m/z): 403 (M+H)$^+$.

EXAMPLE 54

N-[5-(2-Furyl)-1,3,4-oxadiazol-2-yl]-2-phenyl-4-pyridinecarboxamide (Compound Ia-54)

The title compound was synthesized in accordance with the synthesis method of compound Ib-1, using commercially available 2-phenyl-4-pyridinecarboxylic acid instead of 5-phenyl-2-piperidino-7-thiazolo[4,5-b]pyridinecarboxylic acid.
$^1$H-NMR (500M Hz, DMSO-d$_6$) δ: 8.89 (1H, d, J=5.1 Hz), 8.50 (1H, s), 8.18 (2H, d, J=7.4 Hz), 8.06 (1H, d, J=1.7 Hz), 7.84 (1H, d, J=3.4 Hz), 7.56-7.48 (3H, m), 7.30 (1H, d, J=3.4 Hz), 6.81 (1H, dd, J=3.4 Hz, 1.7 Hz).
ES-MS (m/z): 333 (M+H)$^+$.

The following compounds Ia-55 and Ia-56 were synthesized in accordance with the synthesis method of compound Ic-2 described below, using an acid chloride which can be prepared from commercially available corresponding carboxylic acid by a routine method instead of 5-(2-fluorophenyl)-2-furancarbonyl chloride.

EXAMPLE 55

N-[5-(2-Furyl)-1,3,4-oxadiazol-2-yl]-2,6-diphenyl-4-pyridinecarboxamide (Compound Ia-55)

$^1$H-NMR (500M Hz, DMSO-d$_6$) δ: 8.43 (2H, s), 8.29 (4H, d, J=7.4 Hz), 8.07 (1H, s), 7.58 (4H, t, J=7.4 Hz), 7.52 (2H, t, J=7.4 Hz), 7.31 (1H, d, J=3.4 Hz), 6.81 (1H, dd, J=3.4 Hz, 1.7 Hz).
ES-MS (m/z): 409 (M+H)$^+$.

EXAMPLE 56

2-(4-Bromophenyl)-6-(4-chlorophenyl)-N-[5-(2-furyl)-1,3,4-oxadiazol-2-yl]-4-pyridinecarboxamide (Compound Ia-56)

$^1$H-NMR (500M Hz, DMSO-d$_6$) δ: 8.47 (2H, s), 8.33 (2H, d, J=8.6 Hz), 8.26 (2H, d, J=8.6 Hz), 8.09 (1H, d, J=1.7 Hz), 7.80 (2H, d, J=8.6 Hz), 7.66 (2H, d, J=8.6 Hz), 7.32 (1H, d, J=3.4 Hz), 6.83 (1H, dd, J=3.4 Hz, 1.7 Hz).
ES-MS (m/z): 525 (M+5)$^+$, 523 (M+3)$^+$, 521 (M+1)$^+$.

EXAMPLE 57

N-[5-(2-Furyl)-1,3,4-oxadiazol-2-yl]-2-phenyl-5-pyridinecarboxamide (Compound Ia-57)

The title compound was synthesized in accordance with the synthesis method of compound Ic-2 described below, using commercially available 2-phenyl-5-pyridinecarbonyl chloride instead of 5-(2-fluorophenyl)-2-furancarbonyl chloride.
$^1$H-NMR (500M Hz, DMSO-d$_6$) δ: 12.48 (1H, br), 9.25 (1H, d, J=2.4 Hz), 8.46 (1H, dd, J=8.8 Hz, 2.4 Hz), 8.22-8.18 (3H, m), 8.07 (1H, d, J=1.5 Hz), 7.58-7.52 (3H, m), 7.32 (1H, d, J=3.4 Hz), 6.81 (1H, dd, J=3.4 Hz, 1.5 Hz).
ES-MS (m/z): 333 (M+H)$^+$.

EXAMPLE 58

N-[5-(2-Furyl)-1,3,4-oxadiazol-2-yl]-5-(1-methyl-5-indolyl)-3-pyridinecarboxamide (Compound Ia-58)

The title compound was synthesized in accordance with the synthesis method of compound Ia-50, using 5-bromo-N-[5-(2-furyl)-1,3,4-oxadiazol-2-yl]-3-pyridinecarboxamide prepared in Reference Example 8 instead of N-[5-(2-furyl)-1,3,4-oxadiazol-2-yl]-3-iodobenzenecarboxamide.
$^1$H-NMR (500M Hz, DMSO-d$_6$) δ: 9.14 (1H, br), 9.00 (1H, br), 8.60 (1H, br), 7.97 (1H, br), 7.89 (1H, br), 7.48 (2H, br), 7.38 (1H, br), 7.22 (1H, br), 6.75 (1H, br), 6.48 (1H, br), 3.80 (3H, brs).
ES-MS (m/z): 386 (M+H)$^+$.

The following compounds Ia-59 to Ia-68 were synthesized in accordance with the synthesis method of compound Ia-50, using commercially available corresponding boronic acid or boronic acid pinacol ester instead of 1-methyl-5-indoleboronic acid pinacol ester.

EXAMPLE 59

4'-Cyano-3'-fluoro-N-[5-(2-furyl)-1,3,4-oxadiazol-2-yl]-3-biphenylcarboxamide (Compound Ia-59)

ES-MS (m/z): 375 (M+H)$^+$.

EXAMPLE 60

4'-(2-Cyano-2-propyl)-N-[5-(2-furyl)-1,3,4-oxadiazol-2-yl]-3-biphenylcarboxamide (Compound Ia-60)

$^1$H-NMR (500M Hz, DMSO-d$_6$) δ: 12.33 (1H, br), 8.34 (1H, s), 8.06 (1H, d, J=1.7 Hz), 8.01-7.97 (2H, m), 7.85 (2H, d, J=8.5 Hz), 7.68-7.65 (3H, m), 7.29 (1H, d, J=3.4 Hz), 6.80 (1H, dd, J=3.4 Hz, 1.7 Hz), 1.74 (6H, s).
ES-MS (m/z): 399 (M+H)$^+$.

EXAMPLE 61

4'-tert-Butyl-N-[5-(2-furyl)-1,3,4-oxadiazol-2-yl]-3'-nitro-3-biphenylcarboxamide (Compound Ia-61)

ES-MS (m/z): 433 (M+H)$^+$.

EXAMPLE 62

N-[5-(2-Furyl)-1,3,4-oxadiazol-2-yl]-4'-trimethylsilyl-3-biphenylcarboxamide (Compound Ia-62)

ES-MS (m/z): 404 (M+H)$^+$.

EXAMPLE 63

N-[5-(2-Furyl)-1,3,4-oxadiazol-2-yl]-4'-trifluoromethyl-3-biphenylcarboxamide (Compound Ia-63)

ES-MS (m/z): 400 (M+H)$^+$.

EXAMPLE 64

N-[5-(2-Furyl)-1,3,4-oxadiazol-2-yl]-4'-trifluoromethoxy-3-biphenylcarboxamide (Compound Ia-64)

ES-MS (m/z): 416 (M+H)$^+$.

EXAMPLE 65

4'-Benzyl-N-[5-(2-furyl)-1,3,4-oxadiazol-2-yl]-3-biphenylcarboxamide (Compound Ia-65)

ES-MS (m/z): 422 (M+H)$^+$.

EXAMPLE 66

N-[5-(2-Furyl)-1,3,4-oxadiazol-2-yl]-4'-phenoxy-3-biphenylcarboxamide (Compound Ia-66)

$^1$H-NMR (500M Hz, DMSO-$d_6$, @100° C.) δ: 8.37 (1H, s), 8.08 (1H, d, J=7.8 Hz), 7.86 (1H, s), 7.73 (1H, d, J=7.8 Hz), 7.66 (2H, d, J=7.8 Hz), 7.48 (1H, t, J=7.8 Hz), 7.43-7.39 (2H, m), 7.16 (1H, t, J=7.8 Hz), 7.08-7.05 (5H, m), 6.69 (1H, dd, J=3.4 Hz, 1.5 Hz).
ES-MS (m/z): 424 (M+H)$^+$.

EXAMPLE 67

4'-Diphenylamino-N-[5-(2-furyl)-1,3,4-oxadiazol-2-yl]-3-biphenylcarboxamide (Compound Ia-67)

ES-MS (m/z): 499 (M+H)$^+$.

EXAMPLE 68

N-[5-(2-Furyl)-1,3,4-oxadiazol-2-yl]-4'-ureido-3-biphenylcarboxamide (Compound Ia-68)

ES-MS (m/z): 390 (M+H)$^+$.

EXAMPLE 69

N-[5-(2-Furyl)-1,3,4-oxadiazol-2-yl]-4'-methoxycarbonyl-3-biphenylcarboxamide (Compound Ia-69)

The title compound was obtained as a byproduct in the synthesis of compound Ia-23.
$^1$H-NMR (500M Hz, DMSO-$d_6$) δ: 12.39 (1H, brs), 8.43 (1H, s), 8.11-7.97 (7H, m), 7.70 (1H, t, J=7.8 Hz), 7.29 (1H, d, J=3.2 Hz), 6.81 (1H, q, J=1.6 Hz), 3.90 (3H, s).
ES-MS (m/z): 390 (M+H)$^+$.

The following compounds Ia-70 to Ia-76 were synthesized in accordance with the synthesis method of compound Ia-50, using commercially available corresponding boronic acid or boronic acid pinacol ester instead of 1-methyl-5-indoleboronic acid pinacol ester.

EXAMPLE 70

N-[5-(2-Furyl)-1,3,4-oxadiazol-2-yl]-4'-propionyl-3-biphenylcarboxamide (Compound Ia-70)

ES-MS (m/z): 388 (M+H)$^+$.

EXAMPLE 71

N-[5-(2-Furyl)-1,3,4-oxadiazol-2-yl]-4'-piperidinosulfonyl-3-biphenylcarboxamide (Compound Ia-71)

$^1$H-NMR (500M Hz, DMSO-$d_6$, @100° C.) δ: 8.46 (1H, s), 8.18 (1H, d, J=7.8 Hz), 7.90-7.79 (6H, m), 7.54 (1H, t, J=7.8 Hz), 7.07 (1H, d, J=3.4 Hz), 6.69 (1H, dd, J=3.4 Hz, 1.0 Hz), 3.02 (4H, m), 1.55 (4H, m), 1.43 (2H, m).
ES-MS (m/z): 479 (M+H)$^+$.

EXAMPLE 72

N-[5-(2-Furyl)-1,3,4-oxadiazol-2-yl]-4'-sulfo-3-biphenylcarboxamide (Compound Ia-72)

ES-MS (m/z): 410 (M+H)$^+$.

EXAMPLE 73

N-[5-(2-Furyl)-1,3,4-oxadiazol-2-yl]-3-(o-terphenyl)carboxamide (Compound Ia-73)

ES-MS (m/z): 408 (M+H)$^+$.

EXAMPLE 74

N-[5-(2-Furyl)-1,3,4-oxadiazol-2-yl]-3-(m-terphenyl)carboxamide (Compound Ia-74)

ES-MS (m/z): 408 (M+H)$^+$.

EXAMPLE 75

N-[5-(2-Furyl)-1,3,4-oxadiazol-2-yl]-3-(p-terphenyl)carboxamide (Compound Ia-75)

$^1$H-NMR (500M Hz, DMSO-$d_6$, @100° C.) δ: 8.46 (1H, s), 8.12 (1H, d, J=7.8 Hz), 7.88 (1H, d, J=1.0 Hz), 7.83 (1H, d, J=7.8 Hz), 7.77-7.68 (6H, m), 7.55-7.46 (3H, m), 7.37 (1H, t, J=7.3 Hz), 7.11 (1H, d, J=3.4 Hz), 6.70 (1H, dd, J=3.4 Hz, 2.0 Hz).
ES-MS (m/z): 408 (M+H)$^+$.

EXAMPLE 76

3'-Fluoro-N-[5-(2-furyl)-1,3,4-oxadiazol-2-yl]-3-(p-terphenyl)carboxamide (Compound Ia-76)

$^1$H-NMR (500M Hz, DMSO-$d_6$, @100° C.) δ: 8.46 (1H, s), 8.16 (1H, d, J=7.8 Hz), 7.85 (1H, s), 7.81 (1H, d, J=8.3 Hz), 7.59-7.47 (8H, m), 7.42 (1H, d, J=7.8 Hz), 7.08 (1H, d, J=3.4 Hz), 6.68 (1H, dd, J=3.4 Hz, 2.0 Hz).
ES-MS (m/z): 426 (M+H)$^+$.

EXAMPLE 77

4"-Chloro-N-[5-(2-furyl)-1,3,4-oxadiazol-2-yl]-3-(p-terphenyl)carboxamide (Compound Ia-77)

The title compound was synthesized in accordance with the synthesis method of compound Ia-50, using compound Ia-121 instead of compound Ia-50 and using 4-chlorophenylboronic acid instead of 1-methyl-5-indoleboronic acid pinacol ester.

$^1$H-NMR (500M Hz, DMSO-d$_6$, @100° C.) δ: 8.42 (1H, brs), 8.06 (1H, brs), 7.92-7.59 (9H, m), 7.51 (2H, d, J=8.3 Hz), 7.18 (1H, brs), 6.73 (1H, brs).
ES-MS (m/z): 444 ($^{37}$Cl M+H)$^+$, 442 ($^{35}$Cl M+H)$^+$ The following compounds Ia-78 to Ia-90 were synthesized in accordance with the synthesis method of compound Ia-50, using commercially available corresponding boronic acid or boronic acid pinacol ester instead of 1-methyl-5-indoleboronic acid pinacol ester.

EXAMPLE 78

4"-Ethyl-N-[5-(2-Furyl)-1,3,4-oxadiazol-2-yl]-3-(p-terphenyl)carboxamide (Compound Ia-78)

$^1$H-NMR (500M Hz, DMSO-d$_6$, @100° C.) δ: 8.42 (1H, s), 8.07 (1H, d, J=7.8 Hz), 7.91-7.87 (2H, m), 7.77-7.72 (4H, m), 7.63-7.57 (3H, m), 7.31 (2H, d, J=7.8 Hz), 7.16 (1H, d, J=3.4 Hz), 6.72 (1H, dd, J=3.4 Hz, 1.5 Hz), 2.68 (2H, q, J=7.3 Hz), 1.25 (3H, t, J=7.3 Hz).
ES-MS (m/z): 436 (M+H)$^+$.

EXAMPLE 79

4"-Ethoxy-N-[5-(2-furyl)-1,3,4-oxadiazol-2-yl]-3-(p-terphenyl)carboxamide (Compound Ia-79)

ES-MS (m/z): 452 (M+H)$^+$.

EXAMPLE 80

N-[5-(2-Furyl)-1,3,4-oxadiazol-2-yl]-4"-propoxy-3-(p-terphenyl)carboxamide (Compound Ia-80)

$^1$H-NMR (500M Hz, DMSO-d$_6$, @100° C.) δ: 8.40 (1H, brs), 8.06 (1H, brs), 7.92-7.90 (2H, m), 7.77-7.58 (7H, m), 7.17 (1H, brd, J=2.9 Hz), 7.03 (2H, brd, J=8.8 Hz), 6.73 (1H, brd, J=2.0 Hz), 4.01 (2H, t, J=6.3 Hz), 1.77 (2H, m), 1.02 (3H, t, J=7.3 Hz).
ES-MS (m/z): 466 (M+H)$^+$.

EXAMPLE 81

N-[5-(2-Furyl)-1,3,4-oxadiazol-2-yl]-4"-isopropoxy-3-(p-terphenyl)carboxamide (Compound Ia-81)

$^1$H-NMR (500M Hz, DMSO-d$_6$, @100° C.) δ: 8.41 (1H, brs), 8.06 (1H, brd, J=6.8 Hz), 7.92-7.90 (2H, m), 7.76-7.58 (7H, m), 7.17 (1H, brd, J=2.9 Hz), 7.01 (2H, brd, J=8.8 Hz), 6.73 (1H, brs), 4.64 (1H, m), 1.32 (6H, d, J=5.9 Hz).
ES-MS (m/z): 466 (M+H)$^+$.

EXAMPLE 82

N-[5-(2-Furyl)-1,3,4-oxadiazol-2-yl]-4'-(1-naphthyl)-3-biphenylcarboxamide (Compound Ia-82)

$^1$H-NMR (500M Hz, DMSO-d$_6$, @100° C.) δ: 8.49 (1H, s), 8.11 (1H, d, J=7.3 Hz), 8.00-7.87 (7H, m), 7.61-7.48 (7H, m), 7.14 (1H, d, J=3.4 Hz), 6.71 (1H, s).
ES-MS (m/z): 458 (M+H)$^+$.

EXAMPLE 83

N-[5-(2-Furyl)-1,3,4-oxadiazol-2-yl]-4'-(2-naphthyl)-3-biphenylcarboxamide (Compound Ia-83)

$^1$H-NMR (500M Hz, DMSO-d$_6$, @100° C.) δ: 8.49 (1H, s), 8.20 (1H, s), 8.14 (1H, d, J=7.8 Hz), 8.00-7.78 (10H, m), 7.55-7.51 (3H, m), 7.11 (1H, d , J=3.4 Hz), 6.70 (1H, dd, J=3.4 Hz, 1.5 Hz).
ES-MS (m/z): 458 (M+H)$^+$.

EXAMPLE 84

4'-Cyclohexyl-N-[5-(2-furyl)-1,3,4-oxadiazol-2-yl]-3-biphenylcarboxamide (Compound Ia-84)

$^1$H-NMR (500M Hz, DMSO-d$_6$, @80° C.) δ: 8.37 (1H, brs), 8.07 (1H, brs), 7.88 (1H, brs), 7.71 (1H, brs), 7.55-7.44 (4H, brm), 7.26 (1H, brs), 7.10 (1H, brs), 6.70 (1H, brs), 2.59 (1H, br), 1.83-1.80 (4H, brm), 1.44-1.38 (4H, brm), 1.27-1.24 (2H, brm).
ES-MS (m/z): 414 (M+H)$^+$.

EXAMPLE 85

N-[5-(2-Furyl)-1,3,4-oxadiazol-2-yl]-4'-(trans-4-n-propylcyclohexyl)-3-biphenylcarboxamide (Compound Ia-85)

$^1$H-NMR (500M Hz, DMSO-d$_6$, @80° C.) δ: 8.29 (1H, s), 7.98-7.96 (2H, m), 7.90 (1H, d, J=7.8 Hz), 7.68-7.59 (3H, m), 7.35 (2H, d, J=8.3 Hz), 7.24 (1H, d, J=3.4 Hz), 6.76 (1H, dd, J=3.4 Hz, 2.0 Hz), 2.54 (1H, m), 1.91-1.85 (2H, m), 1.51-1.08 (11H, m), 0.90 (3H, t, J=7.3 Hz).
ES-MS (m/z): 456 (M+H)$^+$.

EXAMPLE 86

N-[5-(2-Furyl)-1,3,4-oxadiazol-2-yl]-3'-morpholino-3-biphenylcarboxamide (Compound Ia-86)

ES-MS (m/z): 417 (M+H)$^+$.

EXAMPLE 87

N-[5-(2-Furyl)-1,3,4-oxadiazol-2-yl]-4'-morpholino-3-biphenylcarboxamide formate (compound Ia-87)

$^1$H-NMR (500M Hz, DMSO-d$_6$) δ: 8.30 (1H, s), 8.07 (1H, s), 7.91 (2H, m), 7.70 (2H, d, J=9.1 Hz), 7.60 (1H, t, J=7.9 Hz), 7.30 (1H, d, J=3.4 Hz), 7.08 (2H, d, J=9.1 Hz), 6.81 (1H, dd, J=3.4 Hz, 1.7 Hz), 3.78-3.77 (4H, t, J=4.5 Hz), 3.21-3.19 (4H, t, J=4.5 Hz).
ES-MS (m/z): 417 (M+H)$^+$.

EXAMPLE 88

4'-(4-tert-Butoxycarbonyl-1-piperazinyl)-N-[5-(2-furyl)-1,3,4-oxadiazol-2-yl]-3-biphenylcarboxamide (Compound Ia-88)

$^1$H-NMR (500M Hz, CDCl$_3$) δ: 8.30 (1H, brs), 8.05 (1H, brs), 7.79 (1H, brs), 7.65 (1H, brs), 7.60-7.55 (3H, brm), 7.17 (1H, brs), 6.98 (2H, brd, J=7.9 Hz), 6.60 (1H, brs), 3.60 (4H, brs), 3.19 (4H, brs), 1.51 (9H, brs).
ES-MS (m/z): 516 (M+H)$^+$.

EXAMPLE 89

N-[5-(2-Furyl)-1,3,4-oxadiazol-2-yl]-4'-(1-piperazinyl)-3-biphenylcarboxamide 2trifluoroacetate (Compound Ia-89)

$^1$H-NMR (500M Hz, DMSO-$d_6$) δ: 8.74 (1H, br), 8.28 (1H, s), 8.06 (1H, d, J=1.7 Hz), 7.92 (2H, m), 7.72 (2H, d, J=8.5 Hz), 7.61 (1H, t, J=7.9 Hz), 7.29 (1H, d, J=3.4 Hz), 7.13 (2H, d, J=8.5 Hz), 6.80 (1H, dd, J=3.4 Hz, 1.7 Hz), 3.44-3.42 (4H, m), 3.29-3.27 (4H, m).

ES-MS (m/z): 416 (M+H)$^+$.

EXAMPLE 90

N-[5-(2-Furyl)-1,3,4-oxadiazol-2-yl]-4'-(2-morpholinoethyl)-3-biphenylcarboxamide (Compound Ia-90)

$^1$H-NMR (500M Hz, DMSO-$d_6$, @100° C.) δ: 8.35 (1H, s), 8.04 (1H, d, J=7.3 Hz), 7.90 (1H, s), 7.78 (1H, m), 7.61-7.52 (3H, m), 7.32 (2H, d, J=7.8 Hz), 7.14 (1H, d, J=3.4 Hz), 6.72 (1H, dd, J=3.4 Hz, 1.5 Hz), 3.60 (4H, t, J=4.9 Hz), 2.80 (2H, t, J=7.3 Hz), 2.60 (2H, t, J=7.3 Hz), 2.46 (4H, t, J=4.9 Hz).

ES-MS (m/z): 445 (M+H)$^+$.

EXAMPLE 91

N-[5-(2-Furyl)-1,3,4-oxadiazol-2-yl]-3-(2-pyridyl)benzenecarboxamide (Compound Ia-91)

The title compound was synthesized in accordance with the synthesis method of compound Ia-50, using commercially available 2-bromopyridine instead of compound Ia-50 and using compound Ia-112 described below of 1-methyl-5-indoleboronic acid pinacol ester.

ES-MS (m/z): 333 (M+H)$^+$.

The following compounds Ia-92 to Ia-111 were synthesized in accordance with the synthesis method of compound Ia-50, using commercially available corresponding boronic acid or boronic acid pinacol ester instead of 1-methyl-5-indoleboronic acid pinacol ester.

EXAMPLE 92

3-(2-Cyano-5-pyridyl)-N-[5-(2-furyl)-1,3,4-oxadiazol-2-yl]benzenecarboxamide (Compound Ia-92)

$^1$H-NMR (500M Hz, DMSO-$d_6$, @100° C.) δ: 9.01 (1H, d, J=2.0 Hz), 8.45 (1H, s), 8.26-8.22 (2H, m), 8.01 (1H, d, J=7.8 Hz), 7.86 (2H, brs), 7.56 (1H, t, J=7.8 Hz), 7.07 (1H, d, J=3.4 Hz), 6.69 (1H, dd, J=3.4 Hz, 2.0 Hz).

ES-MS (m/z): 358 (M+H)$^+$.

EXAMPLE 93

N-[5-(2-Furyl)-1,3,4-oxadiazol-2-yl]-3-(2-trifluoromethyl-5-pyridyl)benzenecarboxamide (Compound Ia-93)

ES-MS (m/z): 401 (M+H)$^+$.

EXAMPLE 94

N-[5-(2-Furyl)-1,3,4-oxadiazol-2-yl]-3-(2-morpholino-3-pyridyl)benzenecarboxamide (Compound Ia-94)

ES-MS (m/z): 418 (M+H)$^+$.

EXAMPLE 95

N-[5-(2-Furyl)-1,3,4-oxadiazol-2-yl]-3-(2-morpholino-4-pyridyl)benzenecarboxamide (Compound Ia-95)

ES-MS (m/z): 418 (M+H)$^+$.

EXAMPLE 96

N-[5-(2-Furyl)-1,3,4-oxadiazol-2-yl]-3-[2-(1-piperazinyl)-5-pyridyl]benzenecarboxamide (Compound Ia-96)

ES-MS (m/z): 417 (M+H)$^+$.

EXAMPLE 97

N-[5-(2-Furyl)-1,3,4-oxadiazol-2-yl]-3-(5-phenyl-2-thienyl)benzenecarhoxamide (Compound Ia-97)

ES-MS (m/z): 414 (M+H)$^+$.

EXAMPLE 98

N-[5-(2-Furyl)-1,3,4-oxadiazol-2-yl]-3-(2-morpholino-5-pyrimidinyl)benzenecarboxamide (Compound Ia-98)

ES-MS (m/z): 419 (M+H)$^+$.

EXAMPLE 99

N-[5-(2-Furyl)-1,3,4-oxadiazol-2-yl]-3-(3-quinolyl)benzenecarboxamide (Compound Ia-99)

ES-MS (m/z): 383 (M+H)$^+$.

EXAMPLE 100

N-[5-(2-Furyl)-1,3,4-oxadiazol-2-yl]-3-(6-quinoxalinyl)benzenecarboxamide (Compound Ia-100)

$^1$H-NMR (500M Hz, DMSO-$d_6$, @100° C.) δ: 8.95 (1H, s), 8.92 (1H, s), 8.59 (1H, s), 8.36 (1H, s), 8.19-8.17 (3H, m), 8.00 (1H, d, J=7.3 Hz), 7.88 (1H, s), 7.61 (1H, t, J=7.3 Hz), 7.12 (1H, d, J=3.4 Hz), 6.69 (1H, brd, J=1.5 Hz).

ES-MS (m/z): 384 (M+H)$^+$.

EXAMPLE 101

3-(5-Benzofurazanyl)-N-[5-(2-furyl)-1,3,4-oxadiazol-2-yl]benzenecarboxamide (Compound Ia-101)

ES-MS (m/z): 372 (M−H)$^-$.

EXAMPLE 102

3-(3,4-Ethylenedioxyphenyl)-N-[5-(2-furyl)-1,3,4-oxadiazol-2-yl]benzenecarboxamide (Compound Ia-102)

ES-MS (m/z): 390 (M+H)$^+$.

EXAMPLE 103

N-[5-(2-Furyl)-1,3,4-oxadiazol-2-yl]-3-(4-methyl-1-naphthyl)benzenecarboxamide (Compound Ia-103)

ES-MS (m/z): 396 (M+H)$^+$.

EXAMPLE 104

3-(2-Ethoxy-1-naphthyl)-N-[5-(2-furyl)-1,3,4-oxadiazol-2-yl]benzenecarboxamide (Compound Ia-104)

ES-MS (m/z): 426 (M+H)$^+$.

EXAMPLE 105

3-(4-Fluoro-1-naphthyl)-N-[5-(2-furyl)-1,3,4-oxadiazol-2-yl]benzenecarboxamide (Compound Ia-105)

ES-MS (m/z): 400 (M+H)$^+$.

EXAMPLE 106

N-[5-(2-Furyl)-1,3,4-oxadiazol-2-yl]-3-(3-methoxy-2-naphthyl)benzenecarboxamide (Compound Ia-106)

ES-MS (m/z): 412 (M+H)$^+$.

EXAMPLE 107

N-[5-(2-Furyl)-1,3,4-oxadiazol-2-yl]-3-(6-methoxy-2-naphthyl)benzenecarboxamide (Compound Ia-107)

ES-MS (m/z): 412 (M+H)$^+$.

EXAMPLE 108

3-(6-Ethoxy-2-naphthyl)-N-[5-(2-furyl)-1,3,4-oxadiazol-2-yl]benzenecarboxamide (Compound Ia-108)

ES-MS (m/z): 426 (M+H)$^+$.

EXAMPLE 109

3-(6-Benzyloxy-2-naphthyl)-N-[5-(2-furyl)-1,3,4-oxadiazol-2-yl]benzenecarboxamide (Compound Ia-109)

ES-MS (m/z): 488 (M+H)$^+$.

EXAMPLE 110

3-(9-Anthryl)-N-[5-(2-furyl)-1,3,4-oxadiazol-2-yl]benzenecarboxamide (Compound Ia-110)

ES-MS (m/z): 432 (M+H)$^+$.

EXAMPLE 111

3-(5-Acenaphthenyl)-N-[5-(2-furyl)-1,3,4-oxadiazol-2-yl]benzenecarboxamide (Compound Ia-111)

ES-MS (m/z): 408 (M+H)$^+$.

EXAMPLE 112

N-[5-(2-Furyl)-1,3,4-oxadiazol-2-yl]-3-(4,4,5,5-tetramethyl-1,3,2-dioxaborolane-2-yl)benzenecarboxamide (Compound Ia-112)

The title compound was synthesized in accordance with the synthesis method of compound Ib-1, using commercially available 3-carboxyphenylboronic acid pinacol ester instead of 5-phenyl-2-piperidino-7-thiazolo[4,5-b]pyridinecarboxylic acid.

ES-MS (m/z): 382 (M+H)$^+$.

EXAMPLE 113

4"-Ethyl-2-fluoro-N-[5-(2-furyl)-1,3,4-oxadiazol-2-yl]-3-(p-terphenyl)carboxamide (Compound Ia-113)

The title compound was synthesized in accordance with the synthesis method of compound Ia-50, using 3-bromo-2-fluoro-N-[5-(2-furyl)-1,3,4-oxadiazol-2-yl]benzenecarboxamide prepared in Reference Example 5 instead of compound Ia-50 and using commercially available 4'-ethyl-4-biphenylboronic acid instead of 1-methyl-5-indoleboronic acid pinacol ester.

$^1$H-NMR (500M Hz, DMSO-d$_6$, @100° C.) δ: 7.91 (1H, s), 7.76-7.74 (3H, m), 7.68-7.62 (5H, m), 7.38-7.31 (3H, m), 7.14 (1H, d, J=3.4 Hz), 6.72 (1H, dd, J=3.4 Hz, 1.5 Hz), 2.68 (2H, q, J=7.3 Hz), 1.25 (3H, t, J=7.3 Hz).

ES-MS (m/z): 454 (M+H)$^+$.

EXAMPLE 114

4"-Ethyl-4-fluoro-N-[5-(2-furyl)-1,3,4-oxadiazol-2-yl]-3-(p-terphenyl)carboxamide (Compound Ia-114)

The title compound was synthesized in accordance with the synthesis method of compound Ia-50, using 3-bromo-4-fluoro-N-[5-(2-furyl)-1,3,4-oxadiazol-2-yl]benzenecarboxamide prepared in Reference Example 9 instead of compound Ia-50 and using commercially available 4'-ethyl-4-biphenylboronic acid instead of 1-methyl-5-indoleboronic acid pinacol ester.

$^1$H-NMR (500M Hz, DMSO-d$_6$, @100° C.) δ: 8.33 (1H, m), 8.14 (1H, m), 7.85 (1H, m), 7.72 (2H, d, J=7.3 Hz), 7.63-7.61 (4H, m), 7.33-7.27 (3H, m), 7.06 (1H, d, J=3.4 Hz), 6.68 (1H, dd, J=3.4 Hz, 1.5 Hz), 2.69 (2H, q, J=7.3 Hz), 1.25 (3H, t, J=7.3 Hz).

ES-MS (m/z): 454 (M+H)$^+$.

EXAMPLE 115

4"-Ethyl-N-[5-(2-furyl)-1,3,4-oxadiazol-2-yl]-4-methyl-3-(p-terphenyl)carboxamide (Compound Ia-115)

The title compound was synthesized in accordance with the synthesis method of compound Ia-50, using N-[5-(2-furyl)-1,3,4-oxadiazol-2-yl]-3-iodo-4-methylbenzenecarboxamide prepared in Reference Example 10 instead of compound Ia-50 and using commercially available 4'-ethyl-4-biphenylboronic acid instead of 1-methyl-5-indoleboronic acid pinacol ester.

$^1$H-NMR (500M Hz, DMSO-$d_6$, @100° C.) δ: 8.00-7.98 (2H, brs), 7.87 (1H, brs), 7.70-7.61 (4H, brm), 7.43-7.31 (5H, brm), 7.09 (1H, brs), 6.69 (1H, brs), 2.68 (2H, q, J=7.3 Hz), 2.34 (3H, s), 1.25 (3H, t, J=7.3 Hz).

ES-MS (m/z): 450 (M+H)$^+$.

EXAMPLE 116

4''-Ethyl-5-fluoro-N-[5-(2-furyl)-1,3,4-oxadiazol-2-yl]-3-(p-terphenyl)carboxamide (Compound Ia-116)

The title compound was synthesized in accordance with the synthesis method of compound Ia-50, using 3-bromo-5-fluoro-N-[5-(2-furyl)-1,3,4-oxadiazol-2-yl]benzenecarboxamide prepared in Reference Example 6 instead of compound Ia-50 and using commercially available 4'-ethyl-4-biphenylboronic acid instead of 1-methyl-5-indoleboronic acid pinacol ester.

ES-MS (m/z): 454 (M+H)$^+$.

EXAMPLE 117

6-(4-Biphenylyl)-N-[5-(2-furyl)-1,3,4-oxadiazol-2-yl]-2-pyridinecarboxamide (Compound Ia-117)

The title compound was synthesized in accordance with the synthesis method of compound Ia-50, using 6-bromo-N-[5-(2-furyl)-1,3,4-oxadiazol-2-yl]-2-pyridinecarboxamide prepared in Reference Example 11 instead of compound Ia-50 and using commercially available 4-biphenylboronic acid instead of 1-methyl-5-indoleboronic acid pinacol ester.

ES-MS (m/z): 409 (M+H)$^+$.

EXAMPLE 118

6-(4'-Ethyl-4-biphenylyl)-N-[5-(2-furyl)-1,3,4-oxadiazol-2-yl]-2-pyridinecarboxamide (Compound Ia-118)

The title compound was synthesized in accordance with the synthesis method of compound Ia-50, using 6-bromo-N-[5-(2-furyl)-1,3,4-oxadiazol-2-yl]-2-pyridinecarboxamide prepared in Reference Example 11 instead of compound Ia-50 and using commercially available 4'-ethyl-4-biphenylboronic acid instead of 1-methyl-5-indoleboronic acid pinacol ester.

ES-MS (m/z): 437 (M+H)$^+$.

EXAMPLE 119

5-(4-Biphenylyl)-N-[5-(2-furyl)-1,3,4-oxadiazol-2-yl]-3-pyridinecarboxamide (Compound Ia-119)

The title compound was synthesized in accordance with the synthesis method of compound Ia-50, using 5-bromo-N-[5-(2-furyl)-1,3,4-oxadiazol-2-yl]-3-pyridinecarboxamide prepared in Reference Example 8 instead of compound Ia-50 and using commercially available 4-biphenylboronic acid instead of 1-methyl-5-indoleboronic acid pinacol ester.

ES-MS (m/z): 409 (M+H)$^+$.

EXAMPLE 120

5-(4'-Ethyl-4-biphenylyl)-N-[5-(2-furyl)-1,3,4-oxadiazol-2-yl]-3-pyridinecarboxamide (Compound Ia-120)

The title compound was synthesized in accordance with the synthesis method of compound Ia-50, using 5-bromo-N-[5-(2-furyl)-1,3,4-oxadiazol-2-yl]-3-pyridinecarboxamide prepared in Reference Example 8 instead of compound Ia-50 and using commercially available 4'-ethyl-4-biphenylboronic acid instead of 1-methyl-5-indoleboronic acid pinacol ester.

ES-MS (m/z): 437 (M+H)$^+$.

EXAMPLE 121

4'-Bromo-N-[5-(2-furyl)-1,3,4-oxadiazol-2-yl]-3-biphenylcarboxamide (Compound Ia-121)

The title compound was synthesized in accordance with the synthesis method of compound Ib-1, using commercially available 4'-bromo-3-biphenylcarboxylic acid instead of 5-phenyl-2-piperidino-7-thiazolo[4,5-b]pyridinecarboxylic acid.

$^1$H-NMR (500M Hz, DMSO-$d_6$) δ: 12.31 (1H, brs), 8.34 (1H, s), 8.05 (1H, d, J=1.7 Hz), 8.01-7.97 (2H, m), 7.78 (2H, d, J=8.5 Hz), 7.72 (2H, d, J=8.5 Hz), 7.67 (1H, t, J=7.9 Hz), 7.29 (1H, d, J=3.4 Hz), 6.80 (1H, dd, J=3.4 Hz, 1.7 Hz).

ES-MS (m/z): 412 ($^{81}$Br M+H)$^+$, 410 ($^{79}$Br M+H)$^+$.

The following compounds Ia-122 to Ia-165 were synthesized in accordance with the synthesis method of compound Ia-50, using compound Ia-121 instead of compound Ia-50 and using commercially available corresponding boronic acid or boronic acid pinacol ester instead of 1-methyl-5-indoleboronic acid pinacol ester.

EXAMPLE 122

2''-Fluoro-N-[5-(2-furyl)-1,3,4-oxadiazol-2-yl]-3-(p-terphenyl)carboxamide (Compound Ia-122)

ES-MS (m/z): 426 (M+H)$^+$.

EXAMPLE 123

2''-Chloro-N-[5-(2-furyl)-1,3,4-oxadiazol-2-yl]-3-(p-terphenyl)carboxamide (Compound Ia-123)

ES-MS (m/z): 444 ($^{37}$Cl M+H)$^+$, 442 ($^{35}$Cl M+H)$^+$.

EXAMPLE 124

N-[5-(2-Furyl)-1,3,4-oxadiazol-2-yl]-2''-methyl-3-(p-terphenyl)carboxamide (Compound Ia-124)

ES-MS (m/z): 422 (M+H)$^+$.

EXAMPLE 125

N-[5-(2-Furyl)-1,3,4-oxadiazol-2-yl]-2''-methoxy-3-(p-terphenyl)carboxamide (Compound Ia-125)

ES-MS (m/z): 438 (M+H)$^+$.

EXAMPLE 126

N-[5-(2-Furyl)-1,3,4-oxadiazol-2-yl]-2''-trifluoromethyl-3-(p-terphenyl)carboxamide (Compound Ia-126)

ES-MS (m/z): 476 (M+H)$^+$.

EXAMPLE 127

N-[5-(2-Furyl)-1,3,4-oxadiazol-2-yl]-2''-trifluoromethoxy-3-(p-terphenyl)carboxamide (Compound Ia-127)

ES-MS (m/z): 492 (M+H)$^+$.

EXAMPLE 128

2''-Cyano-N-[5-(2-furyl)-1,3,4-oxadiazol-2-yl]-3-(p-terphenyl)carboxamide (Compound Ia-128)

ES-MS (m/z): 433 (M+H)$^+$.

EXAMPLE 129

N-[5-(2-Furyl)-1,3,4-oxadiazol-2-yl]-3-(1,1':4',1'':2'', 1'''-quaterphenyl)carboxamide (Compound Ia-129)

ES-MS (m/z): 484 (M+H)$^+$.

EXAMPLE 130

3''-Fluoro-N-[5-(2-furyl)-1,3,4-oxadiazol-2-yl]-3-(p-terphenyl)carboxamide (Compound Ia-130)

ES-MS (m/z): 426 (M+H)$^+$.

EXAMPLE 131

3''-Chloro-N-[5-(2-furyl)-1,3,4-oxadiazol-2-yl]-3-(p-terphenyl)carboxamide (Compound Ia-131)

ES-MS (m/z): 444 ($^{37}$Cl M+H)$^+$, 442 ($^{35}$Cl M+H)$^+$.

EXAMPLE 132

N-[5-(2-Furyl)-1,3,4-oxadiazol-2-yl]-3''-methyl-3-(p-terphenyl)carboxamide (Compound Ia-132)

ES-MS (m/z): 422 (M+H)$^+$.

EXAMPLE 133

N-[5-(2-Furyl)-1,3,4-oxadiazol-2-yl]-3''-methoxy-3-(p-terphenyl)carboxamide (Compound Ia-133)

ES-MS (m/z): 438 (M+H)$^+$.

EXAMPLE 134

N-[5-(2-Furyl)-1,3,4-oxadiazol-2-yl]-3''-trifluoromethyl-3-(p-terphenyl)carboxamide (Compound Ia-134)

ES-MS (m/z): 476 (M+H)$^+$.

EXAMPLE 135

N-[5-(2-Furyl)-1,3,4-oxadiazol-2-yl]-3''-trifluoromethoxy-3-(p-terphenyl)carboxamide (Compound Ia-135)

ES-MS (m/z): 492 (M+H)$^+$.

EXAMPLE 136

3''-Cyano-N-[5-(2-furyl)-1,3,4-oxadiazol-2-yl]-3-(p-terphenyl)carboxamide (Compound Ia-136)

ES-MS (m/z): 433 (M+H)$^+$.

EXAMPLE 137

N-[5-(2-Furyl)-1,3,4-oxadiazol-2-yl]-3-(1,1':4',1'':3'', 1'''-quaterphenyl)carboxamide (Compound Ia-137)

ES-MS (m/z): 484 (M+H)$^+$.

EXAMPLE 138

4''-Fluoro-N-[5-(2-furyl)-1,3,4-oxadiazol-2-yl]-3-(p-terphenyl)carboxamide (Compound Ia-138)

ES-MS (m/z): 426 (M+H)$^+$.

EXAMPLE 139

N-[5-(2-Furyl)-1,3,4-oxadiazol-2-yl]-4''-methyl-3-(p-terphenyl)carboxamide (Compound Ia-139)

ES-MS (m/z): 422 (M+H)$^+$.

EXAMPLE 140

N-[5-(2-Furyl)-1,3,4-oxadiazol-2-yl]-4''-methoxy-3-(p-terphenyl)carboxamide (Compound Ia-140)

ES-MS (m/z): 438 (M+H)$^+$.

EXAMPLE 141

N-[5-(2-Furyl)-1,3,4-oxadiazol-2-yl]-4''-trifluoromethyl-3-(p-terphenyl)carboxamide (Compound Ia-141)

ES-MS (m/z): 476 (M+H)$^+$.

EXAMPLE 142

N-[5-(2-Furyl)-1,3,4-oxadiazol-2-yl]-4''-trifluoromethoxy-3-(p-terphenyl)carboxamide (Compound Ia-142)

ES-MS (m/z): 492 (M+H)$^+$.

EXAMPLE 143

4''-Cyano-N-[5-(2-furyl)-1,3,4-oxadiazol-2-yl]-3-(p-terphenyl)carboxamide (Compound Ia-143)

ES-MS (m/z): 433 (M+H)$^+$.

EXAMPLE 144

N-[5-(2-Furyl)-1,3,4-oxadiazol-2-yl]-3-(1,1':4',1":4",1'"-quaterphenyl)carboxamide (Compound Ia-144)

ES-MS (m/z): 484 (M+H)$^+$.

EXAMPLE 145

N-[5-(2-Furyl)-1,3,4-oxadiazol-2-yl]-4"-trimethylsilyl-3-(p-terphenyl)carboxamide (Compound Ia-145)

ES-MS (m/z): 480 (M+H)$^+$.

EXAMPLE 146

4'-(1-Cyclohexenyl)-N-[5-(2-furyl)-1,3,4-oxadiazol-2-yl]-3-biphenylcarboxamide (Compound Ia-146)

ES-MS (m/z): 412 (M+H)$^+$.

EXAMPLE 147

4'-(4,4-Dimethyl-1-cyclohexenyl)-N-[5-(2-furyl)-1,3,4-oxadiazol-2-yl]-3-biphenylcarboxamide (Compound Ia-147)

ES-MS (m/z): 440 (M+H)$^+$.

EXAMPLE 148

4'-(4-tert-Butyl-1-cyclohexenyl)-N-[5-(2-furyl)-1,3,4-oxadiazol-2-yl]-3-biphenylcarboxamide (Compound Ia-148)

ES-MS (m/z): 468 (M+H)$^+$.

EXAMPLE 149

N-[5-(2-Furyl)-1,3,4-oxadiazol-2-yl]-4'-(2,2,6,6-tetramethyl-3,6-dihydro-4-pyranyl)-3-biphenylcarboxamide (Compound Ia-149)

ES-MS (m/z): 470 (M+H)$^+$.

EXAMPLE 150

N-[5-(2-Furyl)-1,3,4-oxadiazol-2-yl]-4'-(1-methyl-1,2,3,6-tetrahydro-4-pyridyl)-3-biphenylcarboxamide (Compound Ia-150)

ES-MS (m/z): 427 (M+H)$^+$.

EXAMPLE 151

4'-(2-Furyl)-N-[5-(2-furyl)-1,3,4-oxadiazol-2-yl]-3-biphenylcarboxamide (Compound Ia-151)

ES-MS (m/z): 398 (M+H)$^+$.

EXAMPLE 152

N-[5-(2-Furyl)-1,3,4-oxadiazol-2-yl]-4'-(2-thienyl)-3-biphenylcarboxamide (Compound Ia-152)

ES-MS (m/z): 414 (M+H)$^+$.

EXAMPLE 153

N-[5-(2-Furyl)-1,3,4-oxadiazol-2-yl]-4'-(3-thienyl)-3-biphenylcarboxamide (Compound Ia-153)

ES-MS (m/z): 414 (M+H)$^+$.

EXAMPLE 154

N-[5-(2-Furyl)-1,3,4-oxadiazol-2-yl]-4'-(1-methyl-4-pyrazolyl)-3-biphenylcarboxamide (Compound Ia-154)

ES-MS (m/z): 412 (M+H)$^+$.

EXAMPLE 155

N-[5-(2-Furyl)-1,3,4-oxadiazol-2-yl]-4'-(4-pyridyl)-3-biphenylcarboxamide (Compound Ia-155)

ES-MS (m/z): 409 (M+H)$^+$.

EXAMPLE 156

N-[5-(2-Furyl)-1,3,4-oxadiazol-2-yl]-4'-(1-methyl-5-indolyl)-3-biphenylcarboxamide (Compound Ia-156)

ES-MS (m/z): 461 (M+H)$^+$.

EXAMPLE 157

N-[5-(2-Furyl)-1,3,4-oxadiazol-2-yl]-3"-hydroxy-3-(p-terphenyl)carboxamide (Compound Ia-157)

ES-MS (m/z): 424 (M+H)$^+$.

EXAMPLE 158

N-[5-(2-Furyl)-1,3,4-oxadiazol-2-yl]-4"-(1-propyl)-3-(p-terphenyl)carboxamide (Compound Ia-158)

ES-MS (m/z): 450 (M+H)$^+$.

EXAMPLE 159

N-[5-(2-Furyl)-1,3,4-oxadiazol-2-yl]-4"-isopropyl-3-(p-terphenyl)carboxamide (Compound Ia-159)

ES-MS (m/z): 450 (M+H)$^+$.

EXAMPLE 160

4"'-(1-Butyl)-N-[5-(2-furyl)-1,3,4-oxadiazol-2-yl]-3-(p-terphenyl)carboxamide (Compound Ia-160)

ES-MS (m/z): 464 (M+H)$^+$.

EXAMPLE 161

4"'-tert-Butyl-N-[5-(2-furyl)-1,3,4-oxadiazol-2-yl]-3-(p-terphenyl)carboxamide (Compound Ia-161)

ES-MS (m/z): 464 (M+H)$^+$.

EXAMPLE 162

N-[5-(2-Furyl)-1,3,4-oxadiazol-2-yl]-4"-hydroxy-3-(p-terphenyl)carboxamide (Compound Ia-162)

ES-MS (m/z): 424 (M+H)$^+$.

EXAMPLE 163

4"-(N,N-Dimethylamino)-N-[5-(2-furyl)-1,3,4-oxadiazol-2-yl]-3-(p-terphenyl)carboxamide (Compound Ia-163)

ES-MS (m/z): 451 (M+H)$^+$.

EXAMPLE 164

N-[5-(2-Furyl)-1,3,4-oxadiazol-2-yl]-4"-methanesulfonyl-3-(p-terphenyl)carboxamide (Compound Ia-164)

ES-MS (m/z): 486 (M+H)$^+$.

EXAMPLE 165

N-[5-(2-Furyl)-1,3,4-oxadiazol-2-yl]-4"-sulfamoyl-3-(p-terphenyl)carboxamide (Compound Ia-165)

ES-MS (m/z): 487 (M+H)$^+$.

EXAMPLE 166

5-Chloro-4"-ethyl-N-[5-(2-furyl)-1,3,4-oxadiazol-2-yl]-3-(p-terphenyl)carboxamide (Compound Ia-166)

The title compound was synthesized in accordance with the synthesis method of compound Ia-50, using 3-bromo-5-chloro-N-[5-(2-furyl)-1,3,4-oxadiazol-2-yl]benzenecarboxamide prepared in Reference Example 36 instead of compound Ia-50 and using commercially available 4'-ethyl-4-biphenylboronic acid instead of 1-methyl-5-indoleboronic acid pinacol ester.
ES-MS (m/z): 472 ($^{37}$Cl M+H)$^+$, 470 ($^{35}$Cl M+H)$^+$.

EXAMPLE 167

4"-Ethyl-N-[5-(2-furyl)-1,3,4-oxadiazol-2-yl]-5-nitro-3-(p-terphenyl)carboxamide (Compound Ia-167)

The title compound was synthesized in accordance with the synthesis method of compound Ia-50, using 3-bromo-N-[5-(2-furyl)-1,3,4-oxadiazol-2-yl]-5-nitrobenzenecarboxamide prepared in Reference Example 37 instead of compound Ia-50 and using commercially available 4'-ethyl-4-biphenylboronic acid instead of 1-methyl-5-indoleboronic acid pinacol ester.
ES-MS (m/z): 481 (M+H)$^+$.

EXAMPLE 168

5-Acetylamino-4"-ethyl-N-[5-(2-furyl)-1,3,4-oxadiazol-2-yl]-3-(p-terphenyl)carboxamide (Compound Ia-168)

The title compound was synthesized in accordance with the synthesis method of compound Ia-50, using 5-acetylamino-3-bromo-N-[5-(2-furyl)-1,3,4-oxadiazol-2-yl]benzenecarboxamide prepared in Reference Example 38 instead of compound Ia-50 and using commercially available 4'-ethyl-4-biphenylboronic acid instead of 1-methyl-5-indoleboronic acid pinacol ester.
ES-MS (m/z): 493 (M+H)$^+$.

EXAMPLE 169

4"-Ethyl-N-[5-(2-furyl)-1,3,4-oxadiazol-2-yl]-5-trifluoromethyl-3-(p-terphenyl)carboxamide (Compound Ia-169)

The title compound was synthesized in accordance with the synthesis method of compound Ia-50, using 3-bromo-N-[5-(2-furyl)-1,3,4-oxadiazol-2-yl]-5-trifluoromethylbenzenecarboxamide prepared in Reference Example 39 instead of compound Ia-50 and using commercially available 4'-ethyl-4-biphenylboronic acid instead of 1-methyl-5-indoleboronic acid pinacol ester.
ES-MS (m/z): 504 (M+H)$^+$.

EXAMPLE 170

4"-Ethyl-N-[5-(2-furyl)-1,3,4-oxadiazol-2-yl]-5-trifluoromethoxy-3-(p-terphenyl)carboxamide (Compound Ia-170)

The title compound was synthesized in accordance with the synthesis method of compound Ia-50, using 3-bromo-N-[5-(2-furyl)-1,3,4-oxadiazol-2-yl]-5-trifluoromethoxybenzenecarboxamide prepared in Reference Example 40 instead of compound Ia-50 and using commercially available 4'-ethyl-4-biphenylboronic acid instead of 1-methyl-5-indoleboronic acid pinacol ester.
ES-MS (m/z): 520 (M+H)$^+$.

EXAMPLE 171

5-Cyano-4"-ethyl-N-[5-(2-furyl)-1,3,4-oxadiazol-2-yl]-3-(p-terphenyl)carboxamide (Compound Ia-171)

The title compound was synthesized in accordance with the synthesis method of compound Ia-50, using 3-bromo-5-cyano-N-[5-(2-furyl)-1,3,4-oxadiazol-2-yl]benzenecarboxamide prepared in Reference Example 41 instead of compound Ia-50 and using commercially available 4'-ethyl-4-biphenylboronic acid instead of 1-methyl-5-indoleboronic acid pinacol ester.
ES-MS (m/z): 461 (M+H)$^+$.

EXAMPLE 172

4"-Ethyl-N-[5-(2-furyl)-1,3,4-oxadiazol-2-yl]-5-pentafluorothio-3-(p-terphenyl)carboxamide (Compound Ia-172)

The title compound was synthesized in accordance with the synthesis method of compound Ia-50, using 3-bromo-N-[5-(2-furyl)-1,3,4-oxadiazol-2-yl]-5-pentafluorothiobenzenecarboxamide prepared in Reference Example 42 instead of compound Ia-50 and using commercially available 4'-ethyl-4-biphenylboronic acid instead of 1-methyl-5-indoleboronic acid pinacol ester.
ES-MS (m/z): 562 (M+H)$^+$.

EXAMPLE 173

N-[5-(2-Furyl)-1,3,4-oxadiazol-2-yl]-5-phenyl-2-piperidino-7-thiazolo[4,5-b]pyridinecarboxamide (Compound Ib-1)

2-Amino-5-(2-furyl)-1,3,4-oxadiazole (76 mg, 0.50 mmol), HOAt (68 mg, 0.50 mmol), HATU (190 mg, 0.50 mmol), and N,N-diisopropylethylamine (97 µL, 0.56 mmol) were added to a solution of commercially available 5-phenyl-2-piperidino-7-thiazolo[4,5-b]pyridinecarboxylic acid (85 mg, 0.25 mmol) in DMF (1 mL), followed by stirring overnight at room temperature in an argon atmosphere. To the reaction solution were added 2-amino-5-(2-furyl)-1,3,4-oxadiazole (76 mg, 0.50 mmol), HOAt (68 mg, 0.50 mmol), HATU (190 mg, 0.50 mmol), and N,N-diisopropylethylamine (97 µL, 0.56 mmol), and the mixture was stirred at room temperature for further 4 days. Water was added to the reaction solution, and the precipitated crystals were collected by filtration, washed with water, and recrystallized from methanol to obtain the title compound (27 mg, 0.06 mmol) (yield: 240).

$^1$H-NMR (500M Hz, DMSO-$d_6$) δ: 12.80 (1H, brs), 8.39 (1H, s), 8.20 (2H, d, J=7.2 Hz), 8.06 (1H, s), 7.59-7.42 (3H, m), 7.30 (1H, d, J=1.8 Hz), 6.81 (1H, d, J=1.8 Hz), 3.70 (4H, m), 1.67 (6H, m).

ES-MS (m/z): 473 (M+H)$^+$.

The following compounds Ib-2 to Ib-5 were synthesized in accordance with the synthesis method of compound Ib-1 using commercially available corresponding carboxylic acids instead of 5-phenyl-2-piperidino-7-thiazolo[4,5-b]pyridinecarboxylic acid.

EXAMPLE 174

5-(3-Chlorophenyl)-N-[5-(2-furyl)-1,3,4-oxadiazol-2-yl]-2-piperidino-7-thiazolo[4,5-b]pyridinecarboxamide (Compound Ib-2)

$^1$H-NMR (500M Hz, DMSO-$d_6$) δ: 8.42 (1H, br), 8.22 (1H, s), 8.16 (1H, brs), 8.07 (1H, s), 7.59-7.51 (2H, m), 7.33 (1H, brs), 6.82 (1H, dd, J=3.4 Hz, 1.7 Hz), 3.71 (4H, br), 2.50 (6H, br).

ES-MS (m/z): 509 ($^{37}$Cl M+H)$^+$, 507 ($^{35}$Cl M+H)$^+$.

EXAMPLE 175

N-[5-(2-Furyl)-1,3,4-oxadiazol-2-yl]-5-(4-methylphenyl)-2-piperidino-7-thiazolo[4,5-b]pyridinecarboxamide (Compound Ib-3)

$^1$H-NMR (500M Hz, DMSO-$d_6$) δ: 8.40 (1H, br), 8.11 (2H, d, J=7.4 Hz), 8.07 (1H, d, J=1.7 Hz), 7.35-7.33 (3H, m), 6.81 (1H, dd, J=3.4 Hz, 1.7 Hz), 3.70 (4H, br), 2.38 (3H, s), 1.67 (6H, br).

ES-MS (m/z): 487 (M+H)$^+$.

EXAMPLE 176

N-[5-(2-Furyl)-1,3,4-oxadiazol-2-yl]-5-(3,4-dimethoxyphenyl)-2-piperidino-7-thiazolo[4,5-b]pyridinecarboxamide (Compound Ib-4)

$^1$H-NMR (500M Hz, DMSO-$d_6$, @100° C.) δ: 8.14 (1H, brs), 7.94 (1H, brs), 7.73 (1H, brs), 7.63 (1H, br), 7.21 (1H, brs), 7.06 (1H, brd, J=8.5 Hz), 6.75 (1H, brs), 3.89 (3H, s), 3.85 (3H, s), 3.64 (4H, br), 1.64 (6H, br).

ES-MS (m/z): 533 (M+H)$^+$.

EXAMPLE 177

N-[5-(2-Furyl)-1,3,4-oxadiazol-2-yl]-3-methyl-6-phenyl-4-benzo[d]isoxazolecarboxamide (Compound Ib-5)

$^1$H-NMR (500M Hz, DMSO-$d_6$) δ: 13.00 (1H, brs), 8.47 (1H, d, J=2.3 Hz), 8.30 (2H, m), 8.09 (1H, m), 7.62 (3H, m), 7.33 (1H, m), 6.82 (1H, m), 2.61 (3H, s).

ES-MS (m/z): 388 (M+H)$^+$.

EXAMPLE 178

N-[5-(2-Furyl)-1,3,4-oxadiazol-2-yl]-5-(2-naphthyl)-2-piperidino-7-thiazolo[4,5-b]pyridinecarboxamide (Compound Ib-6)

The title compound was synthesized in accordance with the synthesis method of compound Ib-1, using 5-(2-naphthyl)-2-piperidino-7-thiazolo[4,5-b]pyridinecarboxylic acid prepared in Reference Example 13 instead of 5-phenyl-2-piperidino-7-thiazolo[4,5-b]pyridinecarboxylic acid.

$^1$H-NMR (500M Hz, DMSO-$d_6$, @100° C.) δ: 8.74 (1H, s), 8.50 (1H, s), 8.35 (1H, d, J=9.3 Hz), 8.06-7.94 (4H, m), 7.59-7.52 (2H, m), 7.30 (1H, d, J=3.4 Hz), 6.78 (1H, dd, J=3.4 Hz, 1.5 Hz), 3.75 (4H, brs), 1.72 (6H, brs).

ES-MS (m/z): 523 (M+H)$^+$.

EXAMPLE 179

N-[5-(2-Furyl)-1,3,4-oxadiazol-2-yl]-2-(4-methylpiperidino)-5-phenyl-7-thiazolo[4,5-b]pyridinecarboxamide (Compound Ib-7)

The title compound was synthesized in accordance with the synthesis method of compound Ib-1, using 2-(4-methylpiperidino)-5-phenyl-7-thiazolo[4,5-b]pyridinecarboxylic acid prepared in Reference Example 35 instead of 5-phenyl-2-piperidino-7-thiazolo[4,5-b]pyridinecarboxylic acid.

ES-MS (m/z): 487 (M+H)$^+$.

The following compounds Ib-8 to Ib-25 were synthesized in accordance with the synthesis method of compound Ib-1 using commercially available amines instead of 2-amino-5-(2-furyl)-1,3,4-oxadiazole.

EXAMPLE 180

5-Phenyl-N-(5-phenyl-1,3,4-oxadiazol-2-yl)-2-piperidino-7-thiazolo[4,5-b]pyridinecarboxamide (Compound Ib-8)

$^1$H-NMR (500M Hz, DMSO-$d_6$) δ: 8.42 (1H, brs), 8.20 (2H, d, J=6.2 Hz), 8.00 (2H, d, J=7.4 Hz), 7.64-7.63 (3H, m), 7.55 (2H, m), 7.48 (1H, t, J=7.4 Hz), 3.73 (4H, brs), 1.69 (6H, brs).

ES-MS (m/z): 483 (M+H)$^+$.

EXAMPLE 181

N-[5-(2-Chlorophenyl)-1,3,4-oxadiazol-2-yl]-5-phenyl-2-piperidino-7-thiazolo[4,5-b]pyridinecarboxamide (Compound Ib-9)

$^1$H-NMR (500M Hz, DMSO-$d_6$) δ: 8.45 (1H, brs), 8.21 (2H, d, J=7.4 Hz), 8.00 (1H, dd, J=7.9 Hz, 1.7 Hz), 7.74 (1H, d, J=7.9 Hz), 7.67 (1H, m), 7.61 (1H, t, J=7.9 Hz), 7.54 (2H, m), 7.47 (1H, t, J=7.4 Hz), 3.72 (4H, brs), 1.68 (6H, brs).
ES-MS (m/z): 519 ($^{37}$Cl M+H)$^+$, 517 ($^{35}$Cl M+H)$^+$.

EXAMPLE 182

N-[5-(4-Chlorophenyl)-1,3,4-oxadiazol-2-yl]-5-phenyl-2-piperidino-7-thiazolo[4,5-b]pyridinecarboxamide (Compound Ib-10)

ES-MS (m/z): 519 ($^{37}$Cl M+H)$^+$, 517 ($^{35}$Cl M+H)$^+$.

EXAMPLE 183

N-[5-(4-Methoxyphenyl)-1,3,4-oxadiazol-2-yl]-5-phenyl-2-piperidino-7-thiazolo[4,5-b]pyridinecarboxamide (Compound Ib-11)

$^1$H-NMR (500MHz, DMSO-d$_6$) δ: 8.42 (1H, br), 8.20 (2H, brs), 7.93 (2H, d, J=8.5 Hz), 7.54 (2H, m), 7.47 (1H, t, J=7.4 Hz), 7.17 (2H, d, J=8.5 Hz), 3.86 (3H, s), 3.41 (4H, brs), 1.68 (6H, brs).
ES-MS (m/z): 513 (M+H)$^+$.

EXAMPLE 184

N-[5-(4-Nitrophenyl)-1,3,4-oxadiazol-2-yl]-5-phenyl-2-piperidino-7-thiazolo[4,5-b]pyridinecarboxamide (Compound Ib-12)

ES-MS (m/z): 528 (M+H)$^+$.

EXAMPLE 185

N-(5-Benzyl-1,3,4-oxadiazol-2-yl)-5-phenyl-2-piperidino-7-thiazolo[4,5-b]pyridinecarboxamide (Compound Ib-13)

$^1$H-NMR (500MHz, DMSO-d$_6$) δ: 8.34 (1H, br), 8.17 (2H, d, J=6.8 Hz), 7.52 (2H, t, J=7.4 Hz), 7.45 (2H, t, J=7.4 Hz), 7.40-7.31 (5H, m), 4.28 (2H, s), 3.33 (4H, brs), 1.67 (6H, brs).
ES-MS (m/z): 497 (M+H)$^+$.

EXAMPLE 186

N-[5-(2-Methyl-3-furyl)-1,3,4-oxadiazol-2-yl]-5-phenyl-2-piperidino-7-thiazolo[4,5-b]pyridinecarboxamide (Compound Ib-14)

ES-MS (m/z): 487 (M+H)$^+$.

EXAMPLE 187

N-[5-(2,5-Dimethyl-3-furyl)-1,3,4-oxadiazol-2-yl]-5-phenyl-2-piperidino-7-thiazolo[4,5-b]pyridinecarboxamide (Compound Ib-15)

$^1$H-NMR (500MHz, DMSO-d$_6$) δ: 8.31 (1H, br), 8.10 (2H, d, J=6.8 Hz), 7.44 (2H, m), 7.36 (1H, t, J=7.4 Hz), 6.36 (1H, s), 3.61 (4H, brs), 2.50 (3H, s), 2.20 (3H, s), 1.58 (6H, brs).
ES-MS (m/z): 501 (M+H)$^+$.

EXAMPLE 188

5-Phenyl-2-piperidino-N-[5-(2-thienyl)-1,3,4-oxadiazol-2-yl]-7-thiazolo[4,5-b]pyridinecarboxamide (Compound Ib-16)

ES-MS (m/z): 489 (M+H)$^+$.

EXAMPLE 189

N-[5-(3-Methyl-2-thienyl)-1,3,4-oxadiazol-2-yl]-5-phenyl-2-piperidino-7-thiazolo[4,5-b]pyridinecarboxamide (Compound Ib-17)

$^1$H-NMR (500MHz, DMSO-d$_6$) δ: 8.44 (1H, br), 8.21 (2H, d, J=6.8 Hz), 7.83 (1H, d, J=4.5 Hz), 7.54 (2H, dd, J=7.4 Hz, 6.8 Hz), 7.46 (1H, t, J=7.4 Hz), 7.16 (1H, d, J=4.5 Hz), 3.72 (4H, brs), 2.59 (3H, s), 1.68 (6H, brs).
ES-MS (m/z): 503 (M+H)$^+$.

EXAMPLE 190

N-[5-(5-Methyl-2-thienyl)-1,3,4-oxadiazol-2-yl]-5-phenyl-2-piperidino-7-thiazolo[4,5-b]pyridinecarboxamide (Compound Ib-18)

ES-MS (m/z): 503 (M+H)$^+$.

EXAMPLE 191

5-Phenyl-2-piperidino-N-[5-(3-thienyl)-1,3,4-oxadiazol-2-yl]-7-thiazolo[4,5-b]pyridinecarboxamide (Compound Ib-19)

$^1$H-NMR (500MHz, DMSO-d$_6$) δ: 8.41 (1H, br), 8.34 (1H, brs), 8.20 (2H, d, J=7.4 Hz), 7.84 (1H, dd, J=5.1 Hz, 2.8 Hz), 7.62 (1H, dd, J=5.1 Hz, 1.1 Hz), 7.54 (2H, t, J=7.4 Hz), 7.46 (1H, t, J=7.4 Hz), 3.71 (4H, brs), 1.68 (6H, brs).
ES-MS (m/z): 489 (M+H)$^+$.

EXAMPLE 192

N-[5-(5-Isoxazolyl-1,3,4-oxadiazol-2-yl]-5-phenyl-2-piperidino-7-thiazolo[4,5-b]pyridinecarboxamide (Compound Ib-20)

ES-MS (m/z): 474 (M+H)$^+$.

EXAMPLE 193

N-[5-(1-Methyl-3-pyrazolyl)-1,3,4-oxadiazol-2-yl]-5-phenyl-2-piperidino-7-thiazolo[4,5-b]pyridinecarboxamide (Compound Ib-21)

$^1$H-NMR (500MHz, DMSO-d$_6$) δ: 8.43 (1H, br), 8.21 (2H, d, J=7.4 Hz), 7.97 (1H, d, J=1.7 Hz), 7.54 (2H, t, J=7.4 Hz), 7.46 (1H, t, J=7.4 Hz), 6.88 (1H, d, J=1.7 Hz), 3.98 (3H, s), 3.72 (4H, brs), 1.68 (6H, brs).
ES-MS (m/z): 487 (M+H)$^+$.

EXAMPLE 194

N-[5-(2,4-Dimethyl-5-thiazolyl)-1,3,4-oxadiazol-2-yl]-5-phenyl-2-piperidino-7-thiazolo[4,5-b]pyridinecarboxamide (Compound Ib-22)

ES-MS (m/z): 518 (M+H)$^+$.

EXAMPLE 195

N-[5-(3-Pyridyl)-1,3,4-oxadiazol-2-yl]-5-phenyl-2-piperidino-7-thiazolo[4,5-b]pyridinecarboxamide (Compound Ib-23)

ES-MS (m/z): 484 (M+H)$^+$.

EXAMPLE 196

N-{5-[2-(2,3-Dihydrobenzo[1,4]dioxinyl)]-1,3,4-oxadiazol-2-yl}-5-phenyl-2-piperidino-7-thiazolo[4,5-b]pyridinecarboxamide (Compound Ib-24)

ES-MS (m/z): 541 (M+H)$^+$.

EXAMPLE 197

5-Phenyl-2-piperidino-N-{5-[2-(4,5,6,7-tetrahydrobenzothienyl)]-1,3,4-oxadiazol-2-yl}-7-thiazolo[4,5-b]pyridinecarboxamide (Compound Ib-25)

ES-MS (m/z): 543 (M+H)$^+$.

The following compounds Ib-26 to Ib-29 were synthesized in accordance with the synthesis method of compound Ib-1, using commercially available carboxylic acid instead of 5-phenyl-2-piperidino-7-thiazolo[4,5-b]pyridinecarboxylic acid.

EXAMPLE 198

N-[5-(2-Furyl)-1,3,4-oxadiazol-2-yl]-2-(1-pyrrolidinyl)-5-(2-thienyl)-7-thiazolo[4,5-b]pyridinecarboxamide (Compound Ib-26)

$^1$H-NMR (500MHz, DMSO-d$_6$) δ: 8.37 (1H, br), 8.08 (1H, d, J=1.1 Hz), 7.83 (1H, d, J=3.4 Hz), 7.66 (1H, d, J=4.5 Hz), 7.34 (1H, s), 7.22 (1H, dd, J=4.5 Hz, 3.4 Hz), 6.82 (1H, dd, J=3.4 Hz, 1.7 Hz), 3.66 (4H, br), 2.05 (4H, brs).
ES-MS (m/z): 465 (M+H)$^+$.

EXAMPLE 199

N-[5-(2-Furyl)-1,3,4-oxadiazol-2-yl]-2-piperidino-5-(2-thienyl)-7-thiazolo[4,5-b]pyridinecarboxamide (Compound Ib-27)

$^1$H-NMR (500MHz, DMSO-d$_6$) δ: 8.39 (1H, br), 8.08 (1H, s), 7.83 (1H, d, J=3.4 Hz), 7.66 (1H, d, J=5.1 Hz), 7.34 (1H, brs), 7.22 (1H, brs), 6.82 (1H, dd, J=3.4 Hz, 1.7 Hz), 3.71 (4H, brs), 1.67 (6H, brs)
ES-MS (m/z): 479 (M+H)$^+$..

EXAMPLE 200

N-[5-(2-Furyl)-1,3,4-oxadiazol-2-yl]-2-morpholino-5-(2-thienyl)-7-thiazolo[4,5-b]pyridinecarboxamide (Compound Ib-28)

$^1$H-NMR (500MHz, DMSO-d$_6$) δ: 8.40 (1H, br), 8.08 (1H, s), 7.84 (1H, d, J=3.4 Hz), 7.67 (1H, d, J=5.1 Hz), 7.34 (1H, brs), 7.22 (1H, t, J=4.0 Hz), 6.82 (1H, dd, J=3.4 Hz, 1.7 Hz), 3.77 (4H, brs), 3.71 (4H, brs).
ES-MS (m/z): 481 (M+H)$^+$.

EXAMPLE 201

N-[5-(2-Furyl)-1,3,4-oxadiazol-2-yl]-2-(1-pyrrolidinyl)-5-(3-pyridyl)-7-thiazolo[4,5-b]pyridinecarboxamide (Compound Ib-29)

$^1$H-NMR (500MHz, DMSO-d$_6$, @100° C.) δ: 9.22 (1H, brs), 8.58 (1H, brd, J=3.4 Hz), 8.36 (1H, brd, J=6.8 Hz), 8.16 (1H, brs), 7.90 (1H, brs), 7.46 (1H, brm), 7.14 (1H, brd, J=1.5 Hz), 6.73 (1H, brs), 3.46 (4H, br), 1.96 (4H, br).
ES-MS (m/z): 460 (M+H)$^+$.

EXAMPLE 202

N-[5-(2-Furyl)-1,3,4-oxadiazol-2-yl]-5-phenyl-2-(4-thiomorpholinyl)-7-thiazolo[4,5-b]pyridinecarboxamide (Compound Ib-30)

The title compound was synthesized in accordance with the synthesis method of compound Ib-1, using 5-phenyl-2-(4-thiomorpholinyl)-7-thiazolo[4,5-b]pyridinecarboxylic acid prepared in Reference Example 14 instead of 5-phenyl-2-piperidino-7-thiazolo[4,5-b]pyridinecarboxylic acid.

$^1$H-NMR (500MHz, DMSO-d$_6$) δ: 8.49 (1H, br), 8.21 (2H, brs), 8.08 (1H, s), 7.56-7.53 (2H, m), 7.47 (1H, t, J=7.4 Hz), 7.33 (1H, brs), 6.82 (1H, brs), 4.03 (4H, brs), 2.79 (4H, brs).
ES-MS (m/z): 491 (M+H)$^+$.

EXAMPLE 203

N-[5-(2-Furyl)-1,3,4-oxadiazol-2-yl]-2-(1-methyl-4-piperazinyl)-5-phenyl-7-thiazolo[4,5-b]pyridinecarboxamide (Compound Ib-31)

The title compound was synthesized in accordance with the synthesis method of compound Ib-1, using 2-(1-methyl-4-piperazinyl)-5-phenyl-7-thiazolo[4,5-b]pyridinecarboxylic acid prepared in Reference Example 15 instead of 5-phenyl-2-piperidino-7-thiazolo[4,5-b]pyridinecarboxylic acid.

$^1$H-NMR (500MHz, DMSO-d$_6$, @100° C.) δ: 8.23 (1H, br), 8.10-8.09 (2H, br), 7.92 (1H, br), 7.50-7.38 (3H, br), 7.17 (1H, br), 6.74 (1H, br), 3.70-3.61 (4H, br), 2.81-2.76 (4H, br), 2.28 (3H, brs).
ES-MS (m/z): 488 (M+H)$^+$.

EXAMPLE 204

2-(4,4-Difluoropiperidino)-N-[5-(2-furyl)-1,3,4-oxadiazol-2-yl]-5-phenyl-7-thiazolo[4,5-b]pyridinecarboxamide (Compound Ib-32)

The title compound was synthesized in accordance with the synthesis method of compound Ib-1, using 2-(4,4-difluoropiperidino)-5-phenyl-7-thiazolo[4,5-b]pyridinecarboxylic acid prepared in Reference Example 16 instead of 5-phenyl-2-piperidino-7-thiazolo[4,5-b]pyridinecarboxylic acid.

$^1$H-NMR (500M Hz, DMSO-d$_6$) δ: 8.51 (1H, br), 8.22 (2H, d, J=6.2 Hz), 8.08 (1H, s), 7.55 (2H, dd, J=7.4 Hz, 6.2 Hz), 7.47 (1H, t, J=7.4 Hz), 7.34 (1H, brs), 6.82 (1H, dd, J=3.4 Hz, 1.7 Hz), 3.87 (4H, brs), 2.22-2.17 (4H, m).

ES-MS (m/z): 509 (M+H)$^+$.

EXAMPLE 205

(dl)-N-[5-(2-Furyl)-1,3,4-oxadiazol-2-yl]-2-(2-methylpiperidino)-5-phenyl-7-thiazolo[4,5-b]pyridinecarboxamide (Compound Ib-33)

The title compound was synthesized in accordance with the synthesis method of compound Ib-1, using (dl)-2-(2-methylpiperidino)-5-phenyl-7-thiazolo[4,5-b]pyridinecarboxylic acid prepared in Reference Example 17 instead of 5-phenyl-2-piperidino-7-thiazolo[4,5-b]pyridinecarboxylic acid.

ES-MS (m/z): 487 (M+H)$^+$.

EXAMPLE 206

(dl)-N-[5-(2-Furyl)-1,3,4-oxadiazol-2-yl]-5-phenyl-2-(3-trifluoromethylpiperidino)-7-thiazolo[4,5-b]pyridinecarboxamide (Compound Ib-34)

The title compound was synthesized in accordance with the synthesis method of compound Ib-1, using (dl)-5-phenyl-2-(3-trifluoromethylpiperidino)-7-thiazolo[4,5-b]pyridinecarboxylic acid prepared in Reference Example 18 instead of 5-phenyl-2-piperidino-7-thiazolo[4,5-b]pyridinecarboxylic acid.

ES-MS (m/z): 541 (M+H)$^+$.

EXAMPLE 207

N-[5-(2-Furyl)-1,3,4-oxadiazol-2-yl]-5-phenyl-2-(4-trifluoromethylpiperidino)-7-thiazolo[4,5-b]pyridinecarboxamide (Compound Ib-35)

The title compound was synthesized in accordance with the synthesis method of compound Ib-1, using 5-phenyl-2-(4-trifluoromethylpiperidino)-7-thiazolo[4,5-b]pyridinecarboxylic acid prepared in Reference Example 19 instead of 5-phenyl-2-piperidino-7-thiazolo[4,5-b]pyridinecarboxylic acid.

ES-MS (m/z): 541 (M+H)$^+$.

EXAMPLE 208

2-(4-Cyanopiperidino)-N-[5-(2-furyl)-1,3,4-oxadiazol-2-yl]-5-phenyl-7-thiazolo[4,5-b]pyridinecarboxamide (Compound Ib-36)

The title compound was synthesized in accordance with the synthesis method of compound Ib-1, using 2-(4-cyanopiperidino)-5-phenyl-7-thiazolo[4,5-b]pyridinecarboxylic acid prepared in Reference Example 20 instead of 5-phenyl-2-piperidino-7-thiazolo[4,5-b]pyridinecarboxylic acid.

$^1$H-NMR (500M Hz, DMSO-d$_6$) δ: 8.28-7.94 (4H, m), 7.46-7.36 (3H, m), 7.25-7.11 (1H, m), 6.83-6.73 (1H, m), 3.85 (2H, brs), 3.60 (2H, brs), 3.18 (1H, brs), 1.83-1.66 (4H, m).

ES-MS (m/z): 498 (M+H)$^+$.

EXAMPLE 209

N-[5-(2-Furyl)-1,3,4-oxadiazol-2-yl]-2-morpholino-5-phenyl-7-thiazolo[4,5-b]pyridinecarboxamide (Compound Ib-37)

The title compound was synthesized in accordance with the synthesis method of compound Ib-1, using 2-morpholino-5-phenyl-7-thiazolo[4,5-b]pyridinecarboxylic acid prepared in Reference Example 21 instead of 5-phenyl-2-piperidino-7-thiazolo[4,5-b]pyridinecarboxylic acid.

ES-MS (m/z): 475 (M+H)$^+$.

EXAMPLE 210

2-(1-Azetidinyl)-N-[5-(2-furyl)-1,3,4-oxadiazol-2-yl]-5-phenyl-7-thiazolo[4,5-b]pyridinecarboxamide (Compound Ib-38)

The title compound was synthesized in accordance with the synthesis method of compound Ib-1, using 2-(1-azetidinyl)-5-phenyl-7-thiazolo[4,5-b]pyridinecarboxylic acid prepared in Reference Example 22 instead of 5-phenyl-2-piperidino-7-thiazolo[4,5-b]pyridinecarboxylic acid.

ES-MS (m/z): 445 (M+H)$^+$.

EXAMPLE 211

N-[5-(2-Furyl)-1,3,4-oxadiazol-2-yl]-5-phenyl-2-(1-pyrrolidinyl)-7-thiazolo[4,5-b]pyridinecarboxamide (Compound Ib-39)

The title compound was synthesized in accordance with the synthesis method of compound Ib-1, using 5-phenyl-2-(1-pyrrolidinyl)-7-thiazolo[4,5-b]pyridinecarboxylic acid prepared in Reference Example 23 instead of 5-phenyl-2-piperidino-7-thiazolo[4,5-b]pyridinecarboxylic acid.

ES-MS (m/z): 459 (M+H)$^+$.

EXAMPLE 212

N-[5-(2-Furyl)-1,3,4-oxadiazol-2-yl]-5-phenyl-2-(1,2,3,4-tetrahydro-1-quinolyl)-7-thiazolo[4,5-b]pyridinecarboxamide (Compound Ib-40)

The title compound was synthesized in accordance with the synthesis method of compound Ib-1, using 5-phenyl-2-(1,2,3,4-tetrahydro-1-quinolyl)-7-thiazolo[4,5-b]pyridinecarboxylic acid prepared in Reference Example 24 instead of 5-phenyl-2-piperidino-7-thiazolo[4,5-b]pyridinecarboxylic acid.

ES-MS (m/z): 521 (M+H)$^+$.

EXAMPLE 213

2-Acetylamino-N-[5-(2-furyl)-1,3,4-oxadiazol-2-yl]-5-phenyl-7-thiazolo[4,5-b]pyridinecarboxamide (Compound Ib-41)

The title compound was synthesized in accordance with the synthesis method of compound Ib-1, using 2-acetylamino-5-phenyl-7-thiazolo[4,5-b]pyridinecarboxylic acid prepared in Reference Example 25 instead of 5-phenyl-2-piperidino-7-thiazolo[4,5-b]pyridinecarboxylic acid.

ES-MS (m/z): 447 (M+H)$^+$.

EXAMPLE 214

2-tert-Butoxycarbonylamino-N-[5-(2-furyl)-1,3,4-oxadiazol-2-yl]-5-phenyl-7-thiazolo[4,5-b]pyridinecarboxamide (Compound Ib-42)

The title compound was synthesized in accordance with the synthesis method of compound Ib-1, using 2-tert-butoxycarbonylamino-5-phenyl-7-thiazolo[4,5-b]pyridinecarboxylic acid prepared in Reference Example 26 instead of 5-phenyl-2-piperidino-7-thiazolo[4,5-b]pyridinecarboxylic acid.
ES-MS (m/z): 505 (M+H)$^+$.

EXAMPLE 215

N-[5-(2-Furyl)-1,3,4-oxadiazol-2-yl]-2-(N-methylanilino)-5-phenyl-7-thiazolo[4,5-b]pyridinecarboxamide (Compound Ib-43)

The title compound was synthesized in accordance with the synthesis method of compound Ib-1, using 5-phenyl-2-(N-methylanilino)-7-thiazolo[4,5-b]pyridinecarboxylic acid prepared in Reference Example 27 instead of 5-phenyl-2-piperidino-7-thiazolo[4,5-b]pyridinecarboxylic acid.
ES-MS (m/z): 495 (M+H)$^+$.

EXAMPLE 216

N-[5-(2-Furyl)-1,3,4-oxadiazol-2-yl]-2-(4-hydroxypiperidino)-5-phenyl-7-thiazolo[4,5-b]pyridinecarboxamide (Compound Ib-44)

The title compound was synthesized in accordance with the synthesis method of compound Ib-1, using 2-(4-hydroxypiperidino)-5-phenyl-7-thiazolo[4,5-b]pyridinecarboxylic acid prepared in Reference Example 28 instead of 5-phenyl-2-piperidino-7-thiazolo[4,5-b]pyridinecarboxylic acid.
ES-MS (m/z): 489 (M+H)$^+$.

EXAMPLE 217

N-[5-(2-Furyl)-1,3,4-oxadiazol-2-yl]-5-phenyl-2-(4-phenylpiperidino)-7-thiazolo[4,5-b]pyridinecarboxamide (Compound Ib-45)

The title compound was synthesized in accordance with the synthesis method of compound Ib-1, using 5-phenyl-2-(4-phenylpiperidino)-7-thiazolo[4,5-b]pyridinecarboxylic acid prepared in Reference Example 29 instead of 5-phenyl-2-piperidino-7-thiazolo[4,5-b]pyridinecarboxylic acid.
ES-MS (m/z): 549 (M+H)$^+$.

EXAMPLE 218

N-[5-(2-Furyl)-1,3,4-oxadiazol-2-yl]-5-phenyl-2-(4-piperidinopiperidino)-7-thiazolo[4,5-b]pyridinecarboxamide (Compound Ib-46)

The title compound was synthesized in accordance with the synthesis method of compound Ib-1, using 5-phenyl-2-(4-piperidinopiperidino)-7-thiazolo[4,5-b]pyridinecarboxylic acid prepared in Reference Example 30 instead of 5-phenyl-2-piperidino-7-thiazolo[4,5-b]pyridinecarboxylic acid.
ES-MS (m/z): 556 (M+H)$^+$.

EXAMPLE 219

2-(2,2-Dimethylmorpholino)-N-[5-(2-furyl)-1,3,4-oxadiazol-2-yl]-5-phenyl-7-thiazolo[4,5-b]pyridinecarboxamide (Compound Ib-47)

The title compound was synthesized in accordance with the synthesis method of compound Ib-1, using 2-(2,2-dimethylmorpholino)-5-phenyl-7-thiazolo[4,5-b]pyridinecarboxylic acid prepared in Reference Example 31 instead of 5-phenyl-2-piperidino-7-thiazolo[4,5-b]pyridinecarboxylic acid.
ES-MS (m/z): 503 (M+H)$^+$.

EXAMPLE 220

(dl)-2-[2-(2-Azabicyclo[2.2.1]heptyl]-N-[5-(2-furyl)-1,3,4-oxadiazol-2-yl]-5-phenyl-7-thiazolo[4,5-b]pyridinecarboxamide (Compound Ib-48)

The title compound was synthesized in accordance with the synthesis method of compound Ib-1, using (dl)-2-[2-(2-azabicyclo[2.2.1]heptyl]-5-phenyl-7-thiazolo[4,5-b]pyridinecarboxylic acid prepared in Reference Example 32 instead of 5-phenyl-2-piperidino-7-thiazolo[4,5-b]pyridinecarboxylic acid.
ES-MS (m/z): 485 (M+H)$^+$.

EXAMPLE 221

2-[N-Methyl-N-(3,3,3-trifluoro-1-propyl)amino]-N-[5-(2-furyl)-1,3,4-oxadiazol-2-yl]-5-phenyl-7-thiazolo[4,5-b]pyridinecarboxamide (Compound Ib-49)

The title compound was synthesized in accordance with the synthesis method of compound Ib-1, using 5-phenyl-2-[N-methyl-N-(3,3,3-trifluoro-1-propyl)amino]-7-thiazolo[4,5-b]pyridinecarboxylic acid prepared in Reference Example 33 instead of 5-phenyl-2-piperidino-7-thiazolo[4,5-b]pyridinecarboxylic acid.
ES-MS (m/z): 515 (M+H)$^+$.

EXAMPLE 222

2-(N,N-Dimethylamino)-N-[5-(2-furyl)-1,3,4-oxadiazol-2-yl]-5-phenyl-7-thiazolo[4,5-b]pyridinecarboxamide (Compound Ib-50)

The title compound was synthesized in accordance with the synthesis method of compound Ib-1, using 2-(N,N-dimethylamino)-5-phenyl-7-thiazolo[4,5-b]pyridinecarboxylic acid prepared in Reference Example 34 instead of 5-phenyl-2-piperidino-7-thiazolo[4,5-b]pyridinecarboxylic acid.
$^1$H-NMR (500M Hz, DMSO-$d_6$) δ: 8.44 (1H, brs), 8.21 (2H, d, J=7.9 Hz), 8.08 (1H, s), 7.56-7.53 (2H, m), 7.47 (1H, t, J=7.4 Hz), 7.34 (1H, d, J=3.4 Hz), 6.82 (1H, dd, J=3.4 Hz, 1.7 Hz), 3.27 (6H, s).
ES-MS (m/z): 433 (M+H)$^+$.

EXAMPLE 223

2-Amino-N-[5-(2-furyl)-1,3,4-oxadiazol-2-yl]-5-phenyl-7-thiazolo[4,5-b]pyridinecarboxamide (Compound Ib-51)

The title compound was synthesized by treating compound Ib-42 with trifluoroacetic acid.
ES-MS (m/z): 405 (M+H)$^+$.

EXAMPLE 224

N-[5-(2-Furyl)-1,3,4-oxadiazol-2-yl]-5-phenyl-2-furancarboxamide (Compound Ic-1)

The title compound was synthesized in accordance with the synthesis method of compound Ic-2 described below, using commercially available 5-phenyl-2-furancarbonyl chloride instead of 5-(2-fluorophenyl)-2-furancarbonyl chloride.

$^1$H-NMR (500M Hz, DMSO-d$_6$) δ: 8.00 (1H, d, J=1.7 Hz), 7.95 (2H, d, J=7.4 Hz), 7.55 (1H, brs), 7.45 (2H, d, J=7.4 Hz), 7.37 (1H, t, J=7.4 Hz), 7.23 (1H, d, J=3.4 Hz), 7.19 (1H, d, J=3.4 Hz), 6.75 (1H, dd, J=3.4 Hz, 1.7 Hz).

ES-MS (m/z): 322 (M+H)$^+$.

EXAMPLE 225

5-(2-Fluorophenyl)-N-[5-(2-furyl)-1,3,4-oxadiazol-2-yl]-2-furancarboxamide (Compound Ic-2)

Commercially available 5-(2-fluorophenyl)-2-furancarbonyl chloride (93 mg, 0.41 mmol) was added to a solution of commercially available 2-amino-5-(2-furyl)-1,3,4-oxadiazole (50 mg, 0.33 mmol) in pyridine (1.3 mL) under ice-cooling, followed by stirring at room temperature for 2.5 hr and then at 60° C. for 2 hr. Methanol was added to the reaction solution. The solvent was distilled off, and water was added to the residue. The precipitated crystals were collected by filtration, washed with water, methanol, and ethyl acetate sequentially, and then dried to obtain the title compound (77 mg, 0.23 mmol) (yield: 70%).

$^1$H-NMR (500M Hz, DMSO-d$_6$) δ: 8.26 (1H, brs), 8.07 (1H, d, J=1.7 Hz), 7.65 (1H, brs), 7.51 (1H, m), 7.43-7.39 (2H, m), 7.30 (1H, d, J=3.4 Hz), 7.09 (1H, m), 6.81 (1H, dd, J=3.4 Hz, 1.7 Hz).

ES-MS (m/z): 340 (M+H)$^+$.

The following compounds Ic-3 to Ic-6 were synthesized in accordance with the synthesis method of compound Ic-2, using commercially available corresponding acid chloride instead of 5-(2-fluorophenyl)-2-furancarbonyl chloride.

EXAMPLE 226

N-[5-(2-Furyl)-1,3,4-oxadiazol-2-yl]-5-(2-nitrophenyl)-2-furancarboxamide (Compound Ic-3)

$^1$H-NMR (500M Hz, DMSO-d$_6$) δ: 12.37 (1H, br), 8.06-8.02 (3H, m), 7.85 (1H, dd, J=7.8 Hz, 7.3 Hz), 7.74-7.66 (2H, m), 7.29 (1H, d, J=3.9 Hz), 7.05 (1H, d, J=3.4 Hz), 6.80 (1H, dd, J=3.4 Hz, 2.4 Hz).

ES-MS (m/z): 367 (M+H)$^+$.

EXAMPLE 227

5-(3-Chlorophenyl)-N-[5-(2-furyl)-1,3,4-oxadiazol-2-yl]-2-furancarboxamide (Compound Ic-4)

$^1$H-NMR (500M Hz, DMSO-d$_6$) δ: 8.17 (1H, brs), 8.07 (1H, s), 7.99 (1H, m), 7.60 (1H, brs), 7.54 (1H, t, J=8.0 Hz), 7.49 (1H, m), 7.38 (1H, d, J=3.4 Hz), 7.30 (1H, d, J=3.4 Hz), 6.81 (1H, dd, J=3.4 Hz, 1.7 Hz).

ES-MS (m/z): 358 ($^{37}$Cl M+H)$^+$, 356 ($^{35}$Cl M+H)$^+$.

EXAMPLE 228

N-[5-(2-Furyl)-1,3,4-oxadiazol-2-yl]-5-(3-nitrophenyl)-2-furancarboxamide (Compound Ic-5)

$^1$H-NMR (500M Hz, DMSO-d$_6$) δ: 12.49 (1H, brs), 8.82 (1H, s), 8.45 (1H, d, J=7.8 Hz), 8.26 (1H, m), 8.07 (1H, d, J=1.5 Hz), 7.81 (1H, m), 7.63 (1H, d, J=3.4 Hz), 7.53 (1H, d, J=3.4 Hz), 7.30 (1H, d, J=3.4 Hz), 6.82 (1H, dd, J=3.4 Hz, 1.5 Hz).

ES-MS (m/z): 367 (M+H)$^+$.

EXAMPLE 229

5-(4-Fluorophenyl)-N-[5-(2-furyl)-1,3,4-oxadiazol-2-yl]-2-furancarboxamide (Compound Ic-6)

$^1$H-NMR (500M Hz, CDCl$_3$+MeOH-d$_4$+DMSO-d$_6$, @45° C.) δ: 7.80-7.78 (2H, br), 7.68 (1H, br), 7.28 (1H, br), 7.12-7.04 (3H, br), 6.79 (1H, br), 6.61 (1H, br).

ES-MS (m/z): 340 (M+H)$^+$.

EXAMPLE 230

5-(4-Chlorophenyl)-N-[5-(2-furyl)-1,3,4-oxadiazol-2-yl]-2-furancarboxamide (compound Ic-7)

The title compound was synthesized in accordance with the synthesis method of compound Ib-1, using commercially available 5-(4-chlorophenyl)furancarboxylic acid instead of 5-phenyl-2-piperidino-7-thiazolo[4,5-b]pyridinecarboxylic acid, HBTU instead of HOAt, and HOBt instead of HOAt.

$^1$H-NMR (500M Hz, DMSO-d$_6$) δ: 12.39 (1H, brs), 8.07-8.06 (3H, m), 7.61 (1H, d, J=3.4 Hz), 7.60 (2H, d, J=8.5 Hz), 7.31 (1H, d, J=3.4 Hz), 7.29 (1H, d, J=3.4 Hz), 6.82 (1H, dd, J=3.4 Hz, 1.7 Hz).

ES-MS (m/z): 358 ($^{37}$Cl M+H)$^+$, 356 ($^{35}$Cl M+H)$^+$.

EXAMPLE 231

N-[5-(2-Furyl)-1,3,4-oxadiazol-2-yl]-5-(4-methoxyphenyl)-2-furancarboxamide (compound Ic-8)

The title compound was synthesized in accordance with the synthesis method of compound Ic-2 described below, using an acid chloride prepared from commercially available 5-(4-methoxyphenyl)-2-furancarboxylic acid by a routine method instead of 5-(2-fluorophenyl)-2-furancarbonyl chloride.

ES-MS (m/z): 352 (M+H)$^+$.

EXAMPLE 232

5-(4-Aminophenyl)-N-[5-(2-furyl)-1,3,4-oxadiazol-2-yl]-2-furancarboxamide (compound Ic-9)

The title compound was prepared by reducing compound Ic-11 described below with a zinc powder in acetic acid in accordance with a routine method.

$^1$H-NMR (500M Hz, DMSO-d$_6$) δ: 8.00 (1H, brs), 7.47 (2H, d, J=8.3 Hz), 7.24 (1H, brs), 7.20 (1H, d, J=3.4 Hz), 6.77 (1H, brs), 6.73 (1H, d, J=3.4 Hz), 6.63 (2H, d, J=8.3 Hz), 5.50 (2H, brs).

ES-MS (m/z): 337 (M+H)$^+$.

EXAMPLE 233

5-(4-Acetylaminophenyl)-N-[5-(2-furyl)-1,3,4-oxadiazol-2-yl]-2-furancarboxamide (compound Ic-10)

The title compound was prepared by acetylating compound Ic-9 with acetic anhydride in accordance with a routine method.

$^1$H-NMR (500M Hz, DMSO-$d_6$) δ: 10.07 (1H, brs), 7.91 (1H, brs), 7.67 (4H, brs), 7.19 (1H, brs), 7.13 (1H, brs), 6.97 (1H, brs), 6.70 (1H, brs), 2.05 (3H, s).

ES-MS (m/z): 379 (M+H)$^+$.

The following compounds Ic-11 to Ic-14 were synthesized in accordance with the synthesis method of compound Ic-2, using commercially available corresponding acid chloride instead of 5-(2-fluorophenyl)-2-furancarbonyl chloride.

EXAMPLE 234

N-[5-(2-Furyl)-1,3,4-oxadiazol-2-yl]-5-(4-nitrophenyl)-2-furancarboxamide (Compound Ic-11)

$^1$H-NMR (500M Hz, DMSO-$d_6$) δ: 12.50 (1H, brs), 8.36 (2H, d, J=8.8 Hz), 8.28 (2H, d, J=8.8 Hz), 8.06 (1H, s), 7.64 (1H, s), 7.54 (1H, d, J=3.9 Hz), 7.29 (1H, d, J=3.4 Hz), 6.81 (1H, dd, J=3.4 Hz, 1.5 Hz).

ES-MS (m/z): 367 (M+H)$^+$.

EXAMPLE 235

5-(4-Ethoxycarbonylphenyl)-N-[5-(2-furyl)-1,3,4-oxadiazol-2-yl]-2-furancarboxamide (Compound Ic-12)

$^1$H-NMR (500M Hz, DMSO-$d_6$) δ: 8.17 (2H, d, J=8.0 Hz), 8.08-8.06 (3H, m), 7.65 (1H, d, J=3.4 Hz), 7.44 (1H, d, J=3.4 Hz), 7.29 (1H, d, J=3.4 Hz), 6.82 (1H, d, J=3.4 Hz, 1.7 Hz), 4.35 (2H, q, J=7.4 Hz), 1.35 (3H, t, J=7.4 Hz).

ES-MS (m/z): 394 (M+H)$^+$.

EXAMPLE 236

5-(2,4-Dichlorophenyl)-N-[5-(2-furyl)-1,3,4-oxadiazol-2-yl]-2-furancarboxamide (Compound Ic-13)

$^1$H-NMR (500M Hz, DMSO-$d_6$) δ: 8.15 (1H, s), 8.08 (1H, s), 7.97 (1H, d, J=8.6 Hz), 7.92 (1H, d, J=4.0 Hz), 7.86 (1H, d, J=1.7 Hz), 7.66 (1H, dd, J=8.6 Hz, 1.7 Hz), 7.51 (1H, d, J=3.4 Hz), 7.46 (1H, d, J=4.0 Hz), 6.86 (1H, dd, J=3.4 Hz, 1.7 Hz).

ES-MS (m/z): 392 ($^{37}$Cl M+H)$^+$, 390 ($^{35}$Cl M+H)$^+$.

EXAMPLE 237

5-(2-Chloro-4-nitrophenyl)-N-[5-(2-furyl)-1,3,4-oxadiazol-2-yl]-2-furancarboxamide (Compound Ic-14)

$^1$H-NMR (500M Hz, DMSO-$d_6$) δ: 12.64 (1H, br), 8.56 (1H, d, J=8.3 Hz), 8.45 (1H, d, J=2.0 Hz), 8.37 (1H, d, J=8.3 Hz), 8.07 (1H, s), 7.68 (2H, brs), 7.29 (1H, d, J=3.4 Hz), 6.81 (1H, dd, J=3.4 Hz, 2.0 Hz).

ES-MS (m/z): 403 ($^{37}$Cl M+H)$^+$, 401 ($^{35}$Cl M+H)$^+$.

EXAMPLE 238

5-(4-Amino-2-methylphenyl)-N-[5-(2-furyl)-1,3,4-oxadiazol-2-yl]-2-furancarboxamide (Compound Ic-15)

The title compound was prepared by reducing compound Ic-17 described below with a zinc powder in acetic acid in accordance with a routine method.

ES-MS (m/z): 351 (M+H)$^+$.

EXAMPLE 239

5-(4-Acetylamino-2-methylphenyl)-N-[5-(2-furyl)-1,3,4-oxadiazol-2-yl]-2-furancarboxamide (Compound Ic-16)

The title compound was prepared by acetylating compound Ic-15 with acetic anhydride in accordance with a routine method.

$^1$H-NMR (500M Hz, DMSO-$d_6$) δ: 12.23 (1H, br), 10.09 (1H, brs), 8.06 (1H, s), 7.90 (1H, d, J=8.3 Hz), 7.63 (1H, brs), 7.58 (2H, brs), 7.28 (1H, d, J=3.4 Hz), 6.91 (1H, d, J=3.4 Hz), 6.80 (1H, dd, J=3.4 Hz, 1.5 Hz).

ES-MS (m/z): 393 (M+H)$^+$.

The following compounds Ic-17 to Ic-23 were synthesized in accordance with the synthesis method of compound Ic-2, using commercially available corresponding acid chloride instead of 5-(2-fluorophenyl)-2-furancarbonyl chloride.

EXAMPLE 240

N-[5-(2-Furyl)-1,3,4-oxadiazol-2-yl]-5-(2-methyl-4-nitrophenyl)-2-furancarboxamide (Compound Ic-17)

$^1$H-NMR (500M Hz, DMSO-$d_6$) δ: 12.50 (1H, br), 8.31 (1H, d, J=8.8 Hz), 8.26 (1H, d, J=2.4 Hz), 8.20 (1H, dd, J=8.8 Hz, 2.4 Hz), 8.06 (1H, d, J=1.0 Hz), 7.69 (1H, d, J=3.9 Hz), 7.29 (1H, d, J=3.9 Hz), 7.29 (1H, d, J=3.9 Hz), 6.81 (1H, dd, J=3.4 Hz, 1.0 Hz), 2.67 (3H, s).

ES-MS (m/z): 381 (M+H)$^+$.

EXAMPLE 241

N-[5-(2-Furyl)-1,3,4-oxadiazol-2-yl]-5-(2-methoxy-4-nitrophenyl)-2-furancarboxamide (Compound Ic-18)

$^1$H-NMR (500M Hz, DMSO-$d_6$) δ: 12.55 (1H, br), 8.47 (1H, d, J=8.8 Hz), 8.06 (1H, d, J=1.0 Hz), 8.00 (1H, dd, J=8.8 Hz, 1.5 Hz), 7.92 (1H, d, J=1.5 Hz), 7.63 (1H, d, J=3.9 Hz), 7.39 (1H, d, J=3.4 Hz), 7.29 (1H, d, J=3.9 Hz), 6.81 (1H, dd, J=3.4 Hz, 1.0 Hz), 4.11 (3H, s).

ES-MS (m/z): 397 (M+H)$^+$.

EXAMPLE 242

5-(2-Chloro-5-nitrophenyl)-N-[5-(2-furyl)-1,3,4-oxadiazol-2-yl]-2-furancarboxamide (Compound Ic-19)

$^1$H-NMR (500M Hz, DMSO-$d_6$) δ: 12.60 (1H, br), 8.98 (1H, brs), 8.25 (1H, dd, J=8.8 Hz, 2.9 Hz), 8.07 (1H, d, J=1.5 Hz), 7.93 (1H, d, J=8.8 Hz), 7.69 (1H, brs), 7.57 (1H, d, J=3.4 Hz), 7.30 (1H, d, J=3.4 Hz), 6.81 (1H, dd, J=3.4 Hz, 1.5 Hz).

ES-MS (m/z): 403 ($^{37}$Cl M+H)$^+$, 401 ($^{35}$Cl M+H)$^+$.

EXAMPLE 243

5-(4-Chloro-3-nitrophenyl)-N-[5-(2-furyl)-1,3,4-oxadiazol-2-yl]-2-furancarboxamide (Compound Ic-20)

$^1$H-NMR (500M Hz, DMSO-$d_6$) δ: 12.41 (1H, br), 8.69 (1H, d, J=1.5 Hz), 8.32 (1H, dd, J=8.3 Hz, 1.5 Hz), 8.06 (1H, d, J=1.0 Hz), 7.94 (1H, d, J=8.3 Hz), 7.61 (1H, d, J=3.9 Hz), 7.49 (1H, d, J=3.9 Hz), 7.29 (1H, d, J=3.4 Hz), 6.81 (1H, dd, J=3.4 Hz, 1.0 Hz).
ES-MS (m/z): 403 ($^{37}$Cl M+H)$^+$, 401 ($^{35}$Cl M+H)$^+$.

EXAMPLE 244

5-(3,5-Dichlorophenyl)-N-[5-(2-furyl)-1,3,4-oxadiazol-2-yl]-2-furancarboxamide (Compound Ic-21)

$^1$H-NMR (500M Hz, DMSO-$d_6$) δ: 8.14 (1H, s), 8.08 (1H, brs), 7.94-7.91 (2H, m), 7.72 (1H, d, J=3.4 Hz), 7.57 (1H, d, J=3.4 Hz), 7.53 (1H, d, J=3.4 Hz), 6.86 (1H, dd, J=3.4 Hz, 1.7 Hz).
ES-MS (m/z): 392 ($^{37}$Cl M+H)$^+$, 390 ($^{35}$Cl M+H)$^+$.

EXAMPLE 245

N-[5-(2-Furyl)-1,3,4-oxadiazol-2-yl]-2-methyl-5-phenyl-3-furancarboxamide (Compound Ic-22)

$^1$H-NMR (500M Hz, DMSO-$d_6$) δ: 8.06 (1H, s), 7.66 (2H, d, J=8.0 Hz), 7.52-7.46 (3H, m), 7.35 (1H, t, J=7.4 Hz), 7.29 (1H, d, J=3.4 Hz), 6.81 (1H, dd, J=3.4 Hz, 1.7 Hz), 2.67 (3H, s).
ES-MS (m/z): 336 (M+H)$^+$.

EXAMPLE 246

N-[5-(2-Furyl)-1,3,4-oxadiazol-2-yl]-5-phenyl-2-thiophenecarboxamide (Compound Ic-23)

$^1$H-NMR (500M Hz, DMSO-$d_6$) δ: 12.36 (1H, brs), 8.14 (1H, brs), 8.07 (1H, s), 7.78 (2H, d, J=7.4 Hz), 7.67 (1H, s), 7.49 (2H, t, J=7.4 Hz), 7.42 (1H, t, J=7.4 Hz), 7.30 (1H, s), 6.81 (1H, dd, J=3.4 Hz, 1.7 Hz).
ES-MS (m/z): 338 (M+H)$^+$.

EXAMPLE 247

5-(4-Cyanophenyl)-N-[5-(2-furyl)-1,3,4-oxadiazol-2-yl]-2-thiophenecarboxamide (Compound Ic-24)

The title compound was synthesized in accordance with the synthesis method of compound Ia-50, using 5-bromo-N-[5-(2-furyl)-1,3,4-oxadiazol-2-yl]-2-thiophenecarboxamide prepared in Reference Example 4 instead of N-[5-(2-furyl)-1,3,4-oxadiazol-2-yl]-3-iodobenzenecarboxamide and using commercially available 4-cyanophenylboronic acid instead of 1-methyl-5-indoleboronic acid pinacol ester.
$^1$H-NMR (500M Hz, DMSO-$d_6$, @85° C.) δ: 7.87-7.81 (5H, m), 7.64 (1H, d, J=3.4 Hz), 7.60 (1H, d, J=3.4 Hz), 7.07 (1H, d, J=2.4 Hz), 6.69 (1H, dd, J=3.4 Hz, 2.0 Hz).
ES-MS (m/z): 363 (M+H)$^+$.

The following compounds Ic-25 and Ic-26 were synthesized in accordance with the synthesis method of compound Ib-1, using commercially available corresponding carboxylic acid instead of 5-phenyl-2-piperidino-7-thiazolo[4,5-b]pyridinecarboxylic acid.

EXAMPLE 248

N-[5-(2-Furyl)-1,3,4-oxadiazol-2-yl]-3-phenyl-1-(6,7,8,9-tetrahydro-5H-imidazo[1,5-a]azepinecarboxamide (Compound Ic-25)

$^1$H-NMR (500M Hz, DMSO-$d_6$) δ: 11.05 (1H, brs), 8.11 (1H, s), 7.60 (2H, m), 7.52 (3H, m), 7.26 (1H, d, J=3.5 Hz), 6.77 (1H, m), 4.09 (2H, m), 3.20 (2H, m), 1.81 (2H, m), 1.73 (2H, m), 1.65 (2H, m).
ES-MS (m/z): 390 (M+H)$^+$.

EXAMPLE 249

3-(4-Fluorophenyl)-N-[5-(2-furyl)-1,3,4-oxadiazol-2-yl]-1-(6,7,8,9-tetrahydro-5H-imidazo[1,5-a]azepinecarboxamide (Compound Ic-26)

$^1$H-NMR (500M Hz, DMSO-$d_6$) δ: 11.15 (1H, brs), 8.15 (1H, s), 7.69 (2H, m), 7.43 (2H, m), 7.25 (1H, d, J=2.5 Hz), 6.79 (1H, d, J=1.7 Hz), 4.09 (2H, m), 3.20 (2H, m), 1.83 (2H, m), 1.75 (2H, m), 1.67 (2H, m).
ES-MS (m/z): 408 (M+H)$^+$.

EXAMPLE 250

4-(4-Biphenylyl)-N-[5-(2-furyl)-1,3,4-oxadiazol-2-yl]-2-thiophenecarboxamide (Compound Ic-27)

The title compound was synthesized in accordance with the synthesis method of compound Ia-50, using 4-bromo-N-[5-(2-furyl)-1,3,4-oxadiazol-2-yl]-2-thiophenecarboxamide prepared in Reference Example 12 instead of compound Ia-50 and using commercially available 4-biphenylboronic acid instead of 1-methyl-5-indoleboronic acid pinacol ester.
ES-MS (m/z): 414 (M+H)$^+$.

EXAMPLE 251

4-(4'-Ethyl-4-biphenylyl)-N-[5-(2-furyl)-1,3,4-oxadiazol-2-yl]-2-thiophenecarboxamide (Compound Ic-28)

The title compound was synthesized in accordance with the synthesis method of compound Ia-50, using 4-bromo-N-[5-(2-furyl)-1,3,4-oxadiazol-2-yl]-2-thiophenecarboxamide prepared in Reference Example 12 instead of compound Ia-50 and using commercially available 4'-ethyl-4-biphenylboronic acid instead of 1-methyl-5-indoleboronic acid pinacol ester.
ES-MS (m/z): 442 (M+H)$^+$.

EXAMPLE 252

5-(4-Carboxyphenyl)-N-[5-(2-furyl)-1,3,4-oxadiazol-2-yl]-2-furancarboxamide (Compound Ic-29)

The title compound was prepared by hydrolyzing compound Ic-12 with an aqueous sodium hydroxide solution in accordance with a routine method.
ES-MS (m/z): 364 (M−H)$^−$.

REFERENCE EXAMPLE 1

N-[5-(2-Furyl)-1,3,4-oxadiazol-2-yl]-4-iodo-benzenecarboxamide

4-Iodobenzoyl chloride (2.65 g, 9.95 mmol) was gradually added to a solution of commercially available 2-amino-5-(2- furyl)-1,3,4-oxadiazole (1.00 g, 6.62 mmol) in pyridine (20 mL), followed by stirring at room temperature for 2.5 hr and then at 50° C. overnight. The reaction solution was concentrated. Water and methylene chloride were added to the residue, and precipitated crystals were collected by filtration. The crystals were washed with water and methylene chloride and then dried to obtain the title compound (1.39 g, 3.65 mmol) (yield: 55%).

ES-MS (m/z): 382 (M+H)$^+$.

REFERENCE EXAMPLE 2

3-(5-Sulfamoyl-2-thienyl)benzoic acid (1) 1,1'-Bis(diphenylphosphino)ferrocene-palladium(II) dichloride-dichloromethane complex (272 mg, 0.33 mmol), 3-methoxycarbonylphenylboronic acid (898 mg, 4.99 mmol), and tripotassium phosphate (1.41 g, 6.64 mmol) were added to a solution of commercially available 5-bromothiophene-2-sulfonamide (805 mg, 3.33 mmol) in mixture of 1,4-dioxane (10 mL) and DMF (1 mL), followed by stirring at 85° C. overnight in an argon atmosphere. The reaction solution was concentrated. A saturated aqueous solution of sodium chloride was added to the residue, followed by extraction with methylene chloride and drying over anhydrous sodium sulfate. The solvent was distilled off, and methanol was added to the residue. The precipitated solid was filtered off. The residue obtained by distilling the solvent off was subjected to purification by silica gel column chromatography to obtain 3-(5-sulfamoyl-2-thienyl)benzoic acid methyl ester (529 mg, 1.78 mmol) (yield: 53%).

ES-MS (m/z): 296 (M−H)$^−$.

(2) The title compound was prepared by hydrolyzing 3-(5-sulfamoyl-2-thienyl)benzoic acid methyl ester prepared above with an aqueous sodium hydroxide solution in accordance with a routine method.

ES-MS (m/z): 282 (M−H)$^−$.

REFERENCE EXAMPLE 3

N-[5-(2-Furyl)-1,3,4-oxadiazol-2-yl]-3-iodo-benzenecarboxamide

The title compound was synthesized in accordance with the synthesis method of the compound described in Reference Example 1, using 3-iodobenzoyl chloride instead of 4-iodobenzoyl chloride.

ES-MS (m/z): 382 (M+H)$^+$.

Compounds in the following Reference Examples 4 to 8 were synthesized in accordance with the synthesis method of compound Ib-1 using commercially available corresponding carboxylic acids instead of 5-phenyl-2-piperidino-7-thiazolo[4,5-b]pyridinecarboxylic acid.

REFERENCE EXAMPLE 4

5-Bromo-N-[5-(2-furyl)-1,3,4-oxadiazol-2-yl]-2-thiophenecarboxamide

ES-MS (m/z): 342($^{81}$Br M+H)$^+$, 340($^{79}$Br M+H)$^+$.

REFERENCE EXAMPLE 5

3-Bromo-2-fluoro-N-[5-(2-furyl)-1,3,4-oxadiazol-2-yl]benzenecarboxamide

ES-MS (m/z): 354($^{81}$Br M+H)$^+$, 352($^{79}$Br M+H)$^+$.

REFERENCE EXAMPLE 6

3-Bromo-5-fluoro-N-[5-(2-furyl)-1,3,4-oxadiazol-2-yl]benzenecarboxamide

ES-MS (m/z): 354($^{81}$Br M+H)$^+$, 352($^{79}$Br M+H)$^+$.

REFERENCE EXAMPLE 7

5-Bromo-2-fluoro-N-[5-(2-furyl)-1,3,4-oxadiazol-2-yl]benzenecarboxamide

ES-MS (m/z): 354($^{81}$Br M+H)$^+$, 352($^{79}$Br M+H)$^+$.

REFERENCE EXAMPLE 8

5-Bromo-N-[5-(2-furyl)-1,3,4-oxadiazol-2-yl]-3-pyridinecarboxamide

ES-MS (m/z): 337($^{81}$Br M+H)$^+$, 335($^{79}$Br M+H)$^+$.

Compounds in the following Reference Examples 9 to 12 were synthesized in accordance with the synthesis method of compound Ib-1 using commercially available corresponding carboxylic acids instead of 5-phenyl-2-piperidino-7-thiazolo[4,5-b]pyridinecarboxylic acid.

REFERENCE EXAMPLE 9

3-Bromo-4-fluoro-N-[5-(2-furyl)-1,3,4-oxadiazol-2-yl]benzenecarboxamide

ES-MS (m/z): 354($^{81}$Br M+H)$^+$, 352($^{79}$Br M+H)$^+$.

REFERENCE EXAMPLE 10

N-[5-(2-Furyl)-1,3,4-oxadiazol-2-yl]-3-iodo-4-methyl benzenecarboxamide

ES-MS (m/z): 396 (M+H)$^+$.

REFERENCE EXAMPLE 11

6-Bromo-N-[5-(2-furyl)-1,3,4-oxadiazol-2-yl]-2-pyridinecarboxamide

ES-MS (m/z): 337($^{81}$Br M+H)$^+$, 335($^{79}$Br M+H)$^+$.

REFERENCE EXAMPLE 12

4-Bromo-N-[5-(2-furyl)-1,3,4-oxadiazol-2-yl]-2-thiophenecarboxamide

ES-MS (m/z): 342($^{81}$Br M+H)$^+$, 340($^{79}$Br M+H)$^+$.

Compounds in the following Reference Examples 13 to 15 were synthesized in accordance with Reference Example 16 described below, using commercially available corresponding amines instead of 4,4-difluoropiperidine hydrochloride.

REFERENCE EXAMPLE 13

5-(2-Naphthyl)-2-piperidino-7-thiazolo[4,5-b]pyridinecarboxylic acid

ES-MS (m/z): 390 (M+H)$^+$.

REFERENCE EXAMPLE 14

5-Phenyl-2-(4-thiomorpholinyl)-7-thiazolo[4,5-b]pyridinecarboxylic acid

ES-MS (m/z): 358 (M+H)$^+$.

REFERENCE EXAMPLE 15

2-(1-Methyl-4-piperazinyl)-5-phenyl-7-thiazolo[4,5-b]pyridinecarboxylic acid

ES-MS (m/z): 355 (M+H)$^+$.

REFERENCE EXAMPLE 16

2-(4,4-Difluoropiperidino)-5-phenyl-7-thiazolo[4,5-b]pyridinecarboxylic acid (1) Commercially available 4,4-difluoropiperidine hydrochloride (883 mg, 5.60 mmol) and triethylamine (0.85 mL, 6.10 mmol) were added to a solution of 1,1-thiocarbonyldiimidazole (1.05 g, 5.89 mmol) in THF (20 mL) under ice-cooling, followed by stirring at room temperature for 3 hr in an argon atmosphere. The reaction solution was concentrated. Concentrated aqueous ammonia (30 mL) was added to the residue, followed by stirring overnight at room temperature. The precipitated crystals were collected by filtration, washed with water, and dried to obtain 4,4-difluoropiperidinothiocarboxamide (850 mg, 4.72 mmol) as a light yellow powder.

ES-MS (m/z): 181 (M+H)$^+$.

(2) Chloroacetonitrile (0.32 mL, 5.06 mmol) was added to a solution of 4,4-difluoropiperidinothiocarboxamide (839 mg, 4.66 mmol) prepared above in methanol (15 mL), followed by heating overnight under reflux. The reaction solution was concentrated, and the residue was dissolved in acetic acid (15 mL), followed by addition of commercially available ethyl 4-phenyl-2,4-dioxobutyrate (1.03 g, 4.68 mmol) and sodium acetate (573 mg, 6.99 mmol) thereto. The mixture was heated for 1.5 hr under reflux in an argon atmosphere. The reaction solution was concentrated, and the residue was put into a saturated aqueous solution of sodium hydrogen carbonate. The precipitated crystals were collected by filtration, washed with water, and dried to obtain 2-(4,4-difluoropiperidino)-5-phenyl-7-thiazolo[4,5-b]pyridinecarboxylic acid ethyl ester (1.63 g, 4.04 mmol) as a brown powder.

ES-MS (m/z): 404 (M+H)$^+$.

(3) An aqueous solution of 4 mol/L sodium hydroxide (1.55 mL, 6.20 mmol) and water (1 mL) were added to a solution of 2-(4,4-difluoropiperidino)-5-phenyl-7-thiazolo[4,5-b]pyridinecarboxylic acid ethyl ester (500 mg, 1.24 mmol) prepared above in 1,4-dioxane (5 mL), followed by stirring at room temperature for 3 hr. The reaction solution was concentrated, and a saturated aqueous solution of ammonium chloride was added to the residue. The precipitated crystals were collected by filtration, washed with water, and dried. The resulting crude crystals were subjected to recrystallization from acetic acid-water to obtain the title compound (442 mg, 1.18 mmol) as a yellow powder.

ES-MS (m/z): 376 (M+H)$^+$.

Compounds in the following Reference Examples 17 to 24 were synthesized in accordance with Reference Example 16, using commercially available corresponding amines instead of 4,4-difluoropiperidine hydrochloride.

REFERENCE EXAMPLE 17

(dl)-2-(2-Methylpiperidino)-5-phenyl-7-thiazolo[4,5-b]pyridinecarboxylic acid

ES-MS (m/z): 354 (M+H)$^+$.

REFERENCE EXAMPLE 18

(dl)-5-Phenyl-2-(3-trifluoromethylpiperidino)-7-thiazolo[4,5-b]pyridinecarboxylic acid ES-MS (m/z): 408 (M+H)$^+$.

REFERENCE EXAMPLE 19

5-Phenyl-2-(4-trifluoromethylpiperidino)-7-thiazolo[4,5-b]pyridinecarboxylic acid ES-MS (m/z): 408 (M+H)$^+$.

REFERENCE EXAMPLE 20

2-(4-Cyanopiperidino)-5-phenyl-7-thiazolo[4,5-b]pyridinecarboxylic acid

ES-MS (m/z): 365 (M+H)$^+$.

REFERENCE EXAMPLE 21

2-Morpholino-5-phenyl-7-thiazolo[4,5-b]pyridinecarboxylic acid

ES-MS (m/z): 342 (M+H)$^+$.

REFERENCE EXAMPLE 22

2-(1-Azetidinyl)-5-phenyl-7-thiazolo[4,5-b]pyridinecarboxylic acid

ES-MS (m/z): 312 (M+H)$^+$.

REFERENCE EXAMPLE 23

5-Phenyl-2-(1-pyrrolidinyl)-7-thiazolo[4,5-b]pyridinecarboxylic acid

ES-MS (m/z): 326 (M+H)$^+$.

REFERENCE EXAMPLE 24

5-Phenyl-2-(1,2,3,4-tetrahydro-1-quinolyl)-7-thiazolo[4,5-b]pyridinecarboxylic acid ES-MS (m/z): 388 (M+H)$^+$.

REFERENCE EXAMPLE 25

2-Acetylamino-5-phenyl-7-thiazolo[4,5-b]pyridinecarboxylic acid (1) 2-Acetylamino-5-phenyl-7-thiazolo[4,5-b]pyridinecarboxylic acid ethyl ester was obtained as a byproduct in the step (1) of Reference Example 26 described below.

ES-MS (m/z): 342 (M+H)$^+$.

(2) The title compound was obtained from 2-acetylamino-5-phenyl-7-thiazolo[4,5-b]pyridinecarboxylic acid ethyl ester prepared above in accordance with the step (3) of Reference Example 16.
ES-MS (m/z): 314 (M+H)$^+$.

REFERENCE EXAMPLE 26

2-tert-Butoxycarbonylamino-5-phenyl-7-thiazolo[4,5-b]pyridinecarboxylic acid (1) 2-Amino-5-phenyl-7-thiazolo[4,5-b]pyridinecarboxylic acid ethyl ester was prepared from commercially available thiourea in accordance with the step (2) of Reference Example 16.
ES-MS (m/z): 300 (M+H)$^+$.
(2) 2-tert-Butoxycarbonylamino-5-phenyl-7-thiazolo[4,5-b]pyridinecarboxylic acid ethyl ester was prepared by butyroxycarbonylating 2-amino-5-phenyl-7-thiazolo[4,5-b]pyridinecarboxylic acid ethyl ester prepared above, by a routine method.
ES-MS (m/z): 400 (M+H)$^+$.
(3) The title compound was prepared from 2-tert-butoxycarbonylamino-5-phenyl-7-thiazolo[4,5-b]pyridinecarboxylic acid ethyl ester prepared above in accordance with the step (3) of Reference Example 16.
ES-MS (m/z): 372 (M+H)$^+$.

REFERENCE EXAMPLE 27

5-Phenyl-2-(N-methylanilino)-7-thiazolo[4,5-b]pyridinecarboxylic acid

The title compound was prepared from commercially available N-methyl-N'-phenylthiourea in accordance with the steps (2) and (3) of Reference Example 16.
ES-MS (m/z): 362 (M+H)$^+$.
Compounds in the following Reference Examples 28 to 35 were synthesized in accordance with Reference Example 16, using commercially available corresponding amines instead of 4,4-difluoropiperidine hydrochloride.

REFERENCE EXAMPLE 28

2-(4-Hydroxypiperidino)-5-phenyl-7-thiazolo[4,5-b]pyridinecarboxylic acid

ES-MS (m/z): 356 (M+H)$^+$.

REFERENCE EXAMPLE 29

5-Phenyl-2-(4-phenylpiperidino)-7-thiazolo[4,5-b]pyridinecarboxylic acid

ES-MS (m/z): 416 (M+H)$^+$.

REFERENCE EXAMPLE 30

5-Phenyl-2-(4-piperidinopiperidino)-7-thiazolo[4,5-b]pyridinecarboxylic acid

ES-MS (m/z): 423 (M+H)$^+$.

REFERENCE EXAMPLE 31

2-(2,2-Dimethylmorpholino)-5-phenyl-7-thiazolo[4,5-b]pyridinecarboxylic acid

ES-MS (m/z): 370 (M+H)$^+$.

REFERENCE EXAMPLE 32

(dl)-2-[2-(2-Azabicyclo[2.2.1]heptyl]-5-phenyl-7-thiazolo[4,5-b]pyridinecarboxylic acid ES-MS (m/z): 352 (M+H)$^+$.

REFERENCE EXAMPLE 33

5-Phenyl-2-[N-methyl-N-(3,3,3-trifluoro-1-propyl)amino]-7-thiazolo[4,5-b]pyridinecarboxylic acid ES-MS (m/z): 382 (M+H)$^+$.

REFERENCE EXAMPLE 34

2-(N,N-Dimethylamino)-5-phenyl-7-thiazolo[4,5-b]pyridinecarboxylic acid

ES-MS (m/z): 300 (M+H)$^+$.

REFERENCE EXAMPLE 35

2-(4-Methylpiperidino)-5-phenyl-7-thiazolo[4,5-b]pyridinecarboxylic acid

ES-MS (m/z): 354 (M+H)$^+$.
Compounds in the following Reference Examples 36 to 42 were synthesized in accordance with the synthesis method of compound Ib-1 using commercially available corresponding carboxylic acids instead of 5-phenyl-2-piperidino-7-thiazolo[4,5-b]pyridinecarboxylic acid.

REFERENCE EXAMPLE 36

3-Bromo-5-chloro-N-[5-(2-furyl)-1,3,4-oxadiazol-2-yl]benzenecarboxamide

ES-MS (m/z): 370(M+H)$^+$, 368(M+H)$^+$.

REFERENCE EXAMPLE 37

3-Bromo-N-[5-(2-furyl)-1,3,4-oxadiazol-2-yl]-5-nitrobenzenecarboxamide

ES-MS (m/z): 381($^{81}$Br M+H)$^+$, 379($^{79}$Br M+H)$^+$.

REFERENCE EXAMPLE 38

5-Acetylamino-3-bromo-N-[5-(2-furyl)-1,3,4-oxadiazol-2-yl]benzenecarboxamide

ES-MS (m/z): 393($^{81}$Br M+H)$^+$, 391($^{79}$Br M+H)$^+$.

REFERENCE EXAMPLE 39

3-Bromo-N-[5-(2-furyl)-1,3,4-oxadiazol-2-yl]-5-trifluoromethyl benzenecarboxamide ES-MS (m/z): 404($^{81}$Br M+H)$^+$, 402($^{79}$Br M+H)$^+$.

REFERENCE EXAMPLE 40

3-Bromo-N-[5-(2-furyl)-1,3,4-oxadiazol-2-yl]-5-trifluoromethoxybenzenecarboxamide ES-MS (m/z): 420($^{81}$Br M+H)$^+$, 418($^{79}$Br M+H)$^+$.

REFERENCE EXAMPLE 41

3-Bromo-5-cyano-N-[5-(2-furyl)-1,3,4-oxadiazol-2-yl]benzenecarboxamide

ES-MS (m/z): 361($^{81}$Br M+H)$^+$, 359($^{79}$Br M+H)$^+$.

REFERENCE EXAMPLE 42

3-Bromo-N-[5-(2-furyl)-1,3,4-oxadiazol-2-yl]-5-pentafluorothiobenzenecarboxamide ES-MS (m/z): 462($^{81}$Br M+H)$^+$, 460($^{79}$Br M+H)$^+$.

FORMULATION EXAMPLE 1

Tablets each having a composition consisting of 10 mg of the compound (Ia-50), 70 mg of lactose, 15 mg of starch, 4 mg of polyvinyl alcohol, and 1 mg of magnesium stearate (100 mg in total) are prepared by a routine method.

FORMULATION EXAMPLE 2

An injection having a composition consisting of 70 mg of the compound (Ib-1), 50 mg of purified soybean oil, 10 mg of egg yolk lecithin, and 25 mg of glycerin is prepared by a routine method through adjustment of the total volume to 100 mL with distilled water for injection, packing in a vial, and then heat sterilization.

Industrial Applicability

A 1,3,4-oxadiazole-2-carboxamide compound of the present invention has STAT3 inhibitory activity, and can be used as an anticancer agent or the like for various cancers.

The invention claimed is:

1. A 1,3,4-oxadiazole-2-carboxamide compound of formula (Ia) or a pharmaceutically acceptable salt thereof:

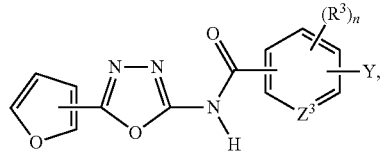
(Ia)

wherein
each $R^3$ is the same or different and is
i) a hydrogen atom,
ii) a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, aromatic heterocyclic alkyl group,
iii) COR$^{11}$, wherein R$^{11}$ is a hydrogen atom, or a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, or aromatic heterocyclic alkyl group,
iv) COOR$^{12}$, wherein R$^{12}$ is as defined in R$^{11}$,
v) C(=Q$^1$)NR$^{13}$R$^{14}$, wherein Q$^1$ is an oxygen atom, a sulfur atom, or NR$^{15}$ (wherein R$^{15}$ is as defined in R$^{11}$); and R$^{13}$ and R$^{14}$ are the same or different and are a hydrogen atom, a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, or aromatic heterocyclic alkyl group; or a group formed by linking R$^{13}$ and R$^{14}$ together, which is a nitrogen-comprising heterocyclic group,
vi) OR$^{16}$, wherein R$^{16}$ is as defined in R$^{11}$,
vii) OCOR$^{17}$, wherein R$^{17}$ is as defined in R$^{11}$,
viii) S(O)pR$^{18}$, wherein p is an integer of 0 to 3, and R$^{18}$ is as defined in R$^{11}$
ix) SO$_2$NR$^{19}$R$^{20}$, wherein R$^{19}$ and R$^{20}$ are the same or different and are as defined in R$^{13}$ and R$^{14}$, respectively,
x) NR$^{21}$R$^{22}$ wherein R$^{21}$ and R$^{22}$ are the same or different and are each a hydrogen atom, a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, aromatic heterocyclic alkyl group, COR$^{23}$ (wherein R$^{23}$ is as defined in R$^{11}$), COOR$^{24}$ (wherein R$^{24}$ is as defined in R$^{11}$), or SO$_2$R$^{25}$ (wherein R$^{25}$ is as defined in R$^{11}$) or a group formed by linking R$^{21}$ and R$^{22}$ together, which is a nitrogen-comprising heterocyclic group,
xi) N(R$^{26}$)C(=Q$^2$)NR$^{27}$R$^{28}$, wherein, Q$^2$ represents an oxygen atom, a sulfur atom, or NR$^{29}$ (wherein R$^{29}$ is as defined in R$^{11}$), NCN, CHNO$_2$, or C(CN)$_2$; R$^{26}$ is as defined in R$^{11}$; and R$^{27}$ and R$^{28}$ are the same or different and are as in R$^{13}$ and R$^{14}$, respectively,
xii) N(R$^{30}$)SO$_2$NR$^{31}$R$^{32}$, wherein R$^{30}$ is as defined in R$^{11}$; and R$^{31}$ and R$^{32}$ are the same or different and are as defined in R$^{13}$ and R$^{14}$, respectively,
xiii) SiR$^{33}$R$^{34}$R$^{35}$, wherein R$^{33}$, R$^{34}$, and R$^{35}$ are the same or different and are each as defined in R$^{11}$,
xiv) a nitro group,
xv) a cyano group,
xvi) a halogen atom, or
xvii) a pentahalogenothio group;
n is an integer of 0 to 2;
Z$^3$ is —CH= or —N=;
Y is an aryl, aromatic heterocyclic, or dioxaborolanyl group which optionally comprises one to three substituents selected from the group consisting of:
i) a substituted or unsubstituted alkyl group, cycloalkyl group, alkenyl group, alkynyl group, alicyclic heterocyclic group, alicyclic heterocyclic alkyl group,
ii) COR$^{41}$, wherein R$^{41}$ is as defined in R$^{11}$,
iii) COOR$^{42}$, wherein R$^{42}$ is as defined in R$^{11}$,
iv) C(=Q$^3$)NR$^{43}$R$^{44}$, wherein Q$^3$ is as defined in Q$^1$, and R$^{43}$ and R$^{44}$ are the same or different and are as defined in R$^{13}$ and R$^{14}$, respectively,
v) OR$^{45}$, wherein R$^{45}$ is as defined in R$^{11}$,
vi) OCOR$^{46}$, wherein R$^{46}$ is as defined in R$^{11}$,
vii) S(O)qR$^{47}$, wherein q is an integer of 0 to 3, and R$^{47}$ is as defined in R$^{11}$,
viii) SO$_2$NR$^{48}$R$^{49}$, wherein R$^{48}$ and R$^{49}$ are the same or different and are as defined in R$^{13}$ and R$^{14}$, respectively,
ix) NR$^{50}$R$^{51}$, wherein R$^{50}$ and R$^{51}$ are the same or different and are as defined in R$^{21}$ and R$^{22}$, respectively, x) $N(R^{52})C(=Q^4)NR^{53}R^{54}$, wherein $Q^4$ is as defined in $Q^2$ $R^{52}$ is as defined in $R^{11}$, and $R^{53}$ and $R^{54}$ are the same or different and are as defined in $R^{13}$ and $R^{14}$, respectively, xi) $N(R^{55})SO_2NR^{56}R^{57}$, wherein $R^{55}$ is as defined in $R^{11}$, and $R^{56}$ and $R^{57}$ are the same or different and are as defined in $R^{13}$ and $R^{14}$, respectively, xii) $SiR^{58}R^{59}R^{60}$, wherein $R^{58}$, $R^{59}$, and $R^{60}$ are the same or different and are each as defined in $R^{11}$, xiii) a nitro group, xiv) a cyano group, and xv) a halogen atom.

2. The compound or salt of claim 1, wherein, in formula (Ia), $Z^3$ is —CH=, and having a formula (Iaa):

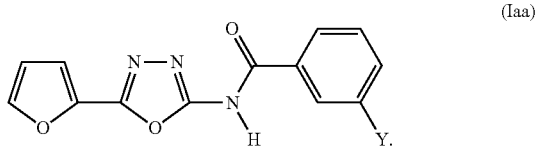

(Iaa)

3. A 1,3,4-oxadiazole-2-carboxamide compound of formula (Ib) or a pharmaceutically acceptable salt thereof:

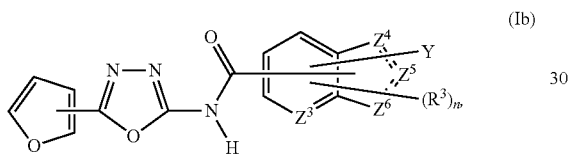

(Ib)

wherein
each $R^3$ is the same or different and is
  i) a hydrogen atom,
  ii) a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, aromatic heterocyclic alkyl group,
  iii) $COR^{11}$, wherein $R^{11}$ is a hydrogen atom, or a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, or aromatic heterocyclic alkyl group,
  iv) $COOR^{12}$, wherein $R^{12}$ is as defined in $R^{11}$,
  v) $C(=Q^1)NR^{13}R^{14}$, wherein $Q^1$ is an oxygen atom, a sulfur atom, or $NR^{15}$ (wherein $R^{15}$ is as defined in $R^{11}$); and $R^{13}$ and $R^{14}$ are the same or different and are a hydrogen atom, a substituted or unsubstituted alkyl group, cycloalkyl group, alkenyl group, alkynyl group, alicyclic heterocyclic group alicyclic heterocyclic alkyl group, aryl group, aralkyl group, aromatic heterocyclic group, or aromatic heterocyclic alkyl group; or a group formed by linking $R^{13}$ and $R^{14}$ together, which is a nitrogen-comprising heterocyclic group,
  vi) $OR^{16}$, wherein $R^{16}$ is as defined in $R^{11}$,
  vii) $OCOR^{17}$, wherein $R^{17}$ is as defined in $R^{11}$,
  viii) $S(O)pR^{18}$, wherein p is an integer of 0 to 3, and $R^{18}$ is as defined in $R^{11}$,
  ix) $SO_2NR^{19}R^{20}$, wherein $R^{19}$ and $R^{20}$ are the same or different and are as defined in $R^{13}$ and $R^{14}$, respectively,
  x) $NR^{21}R^{22}$, wherein $R^{21}$ and $R^{22}$ are the same or different and are each a hydrogen atom, a substituted or unsubstituted alkyl group cycloalkyl group, alkenyl group, alkynyl group, alicyclic heterocyclic group, alicyclic heterocyclic alkyl group, aryl group, aralkyl group, aromatic heterocyclic group, aromatic heterocyclic alkyl group, $COR^{23}$ (wherein $R^{23}$ is as defined in $R^{11}$), $COOR^{24}$ (wherein $R^{24}$ is as defined in $R^{11}$), or $SO_2R^{25}$ (wherein $R^{25}$ is as defined in $R^{11}$); or a group formed by linking $R^{21}$ and $R^{22}$ together, which is a nitrogen-comprising heterocyclic group,
  xi) $N(R^{26})C(=Q^2)NR^{27}R^{28}$, wherein $Q^2$ represents an oxygen atom, a sulfur atom, or $NR^{29}$ (wherein $R^{29}$ is as defined in $R^{11}$), NCN, $CHNO_2$ or $C(CN)_2$; $R^{26}$ is as defined in $R^{11}$; and $R^{27}$ and $R^{28}$ are the same or different and are as in $R^{13}$ and $R^{14}$, respectively,
  xii) $N(R^{30})SO_2NR^{31}R^{32}$, wherein $R^{30}$ is as defined in $R^{11}$; and $R^{31}$ and $R^{32}$ are the same or different and are as defined in $R^{13}$ and $R^{14}$, respectively,
  xiii) $SiR^{33}R^{34}R^{35}$, wherein $R^{33}$, $R^{34}$, and $R^{35}$ are the same or different and are each as defined in $R^{11}$,
  xiv) a nitro group,
  xv) a cyano group,
  xvi) a halogen atom, or
  xvii) a pentahalogenothio group;
n is an integer of 0 to 2;
$Z^3$ and $Z^5$ are the same or different and are —CH= or —N=;
one of $Z^4$ and $Z^6$ is —O— or —S—, and the other is —CH= or —N=;
Y is an aryl, aromatic heterocyclic, or dioxaborolanyl group which optionally comprises one to three substituents selected from the group consisting of:
  i) a substituted or unsubstituted alkyl group, cycloalkyl group, alkenyl group, alkynyl group, alicyclic heterocyclic group, alicyclic heterocyclic alkyl group,
  ii) $COR^{41}$, wherein $R^{41}$ is as defined in $R^{11}$,
  iii) $COOR^{42}$, wherein $R^{42}$ is as defined in $R^{11}$,
  iv) $C(=Q^3)NR^{43}R^{44}$ wherein $Q^3$ is as defined in $Q^1$, and $R^{43}$ and $R^{44}$ are the same or different and are as defined in $R^{13}$ and $R^{14}$, respectively,
  v) $OR^{45}$, wherein $R^{45}$ is as defined in $R^{11}$,
  vi) $OCOR^{46}$, wherein $R^{46}$ is as defined in $R^{11}$,
  vii) $S(O)qR^{47}$, wherein q is an integer of 0 to 3, and $R^{47}$ is as defined in $R^{11}$,
  viii) $SO_2NR^{48}R^{49}$, wherein $R^{48}$ and $R^{49}$ are the same or different and are as defined in $R^{13}$ and $R^{14}$, respectively,
  ix) $NR^{50}R^{51}$, wherein $R^{50}$ and $R^{51}$ are the same or different and are as defined in $R^{21}$ and $R^{22}$, respectively,
  x) $N(R^{52})C(=Q^4)NR^{53}R^{54}$, wherein $Q^4$ is as defined in $Q^2 R^{52}$ is as defined in $R^{11}$, and $R^{53}$ and $R^{54}$ are the same or different and are as defined in $R^{13}$ and $R^{14}$, respectively,
  xi) $N(R^{55})SO_2NR^{56}R^{57}$, wherein $R^{55}$ is as defined in $R^{11}$, and $R^{56}$ and $R^{57}$ are the same or different and are as defined in $R^{13}$ and $R^{14}$, respectively,
  xii) $SiR^{58}R^{59}R^{60}$, wherein $R^{58}$, $R^{59}$, and $R^{60}$ are the same or different and are each as defined in $R^{11}$,
  xiii) a nitro group,
  xiv) a cyano group, and
  xv) a halogen atom.

4. The compound or salt of claim 3, wherein, in formula (Ib):
$Z^3$ and $Z^6$ are —N=;
$Z^5$ is —CH= and
$Z^4$ is —S—, and having a formula (Iba):

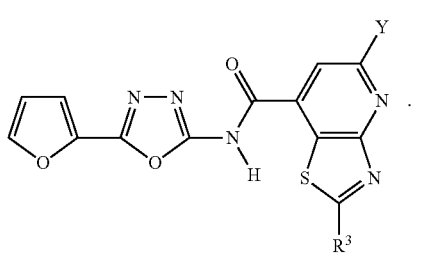

(Iba)

5. A 1,3,4-oxadiazole-2-carboxamide compound of formula (Ic) or a pharmaceutically acceptable salt thereof:

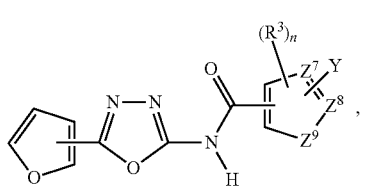

(Ic)

wherein
each $R^3$ is the same or different and is
  i) a hydrogen atom,
  ii) a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, aromatic heterocyclic alkyl group,
  iii) $COR^{11}$, wherein $R^{11}$ is a hydrogen atom, or a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, or aromatic heterocyclic alkyl group,
  iv) $COOR^{12}$, wherein $R^{12}$ is as defined in $R^{11}$,
  v) $C(=Q^1)NR^{13}R^{14}$, wherein $Q^1$ is an oxygen atom, a sulfur atom, or $NR^{15}$ (wherein $R^{15}$ is as defined in $R^{11}$); and $R^{13}$ and $R^{14}$ are the same or different and are a hydrogen atom a substituted or unsubstituted alkynyl group, alicyclic heterocyclic group, alicyclic heterocyclic alkyl group, aryl group, aralkyl group, aromatic heterocyclic group, or aromatic heterocyclic alkyl or a group; formed by linking $R^{13}$ and $R^{14}$ together, which is a nitrogen-comprising heterocyclic group,
  vi) $OR^{16}$, wherein $R^{16}$ is as defined in $R^{11}$,
  vii) $OCOR^{17}$, wherein $R^{17}$ is as defined in $R^{11}$,
  viii) $S(O)pR^{18}$, wherein p is an integer of 0 to 3, and $R^{11}$ is as defined in $R^{11}$,
  ix) $SO_2NR^{19}R^{20}$, wherein $R^{19}$ and $R^{20}$ are the same or different and are as defined in $R^{13}$ and $R^{14}$, respectively,
  x) $NR^{21}R^{22}$, wherein $R^{21}$ and $R^{22}$ are the same or different and are each a hydrogen atom, a substituted or unsubstituted alkyl group, cycloalkyl group, alkenyl group, alkynyl group, alicyclic heterocyclic group, alicyclic heterocyclic alkyl group, aryl group, aralkyl group, aromatic heterocyclic group, aromatic heterocyclic alkyl group, $COR^{23}$ (wherein $R^{23}$ is as defined in $R^{11}$, $COOR^{24}$ (wherein $R^{24}$ is as defined in $R^{11}$), or $SO_2R^{25}$ (wherein $R^{25}$ is as defined in $R^{11}$); or a group formed by linking $R^{21}$ and $R^{22}$ together, which is a nitrogen-comprising heterocyclic group,
  xi) $N(R^{26})C(=Q^2)NR^{27}R^{28}$, wherein, $Q^2$ represents an oxygen atom, a sulfur atom, or $NR^{29}$ (wherein $R^{29}$ is as defined in $R^{11}$), NCN, $CHNO_2$ or $C(CN)_2$; $R^{26}$ is as defined in $R^{11}$; and $R^{27}$ and $R^{28}$ are the same or different and are as in $R^{13}$ and $R^{14}$, respectively,
  xii) $N(R^{30})SO_2NR^{31}R^{32}$, wherein $R^{30}$ is as defined in $R^{11}$; and $R^{31}$ and $R^{32}$ are the same or different and are as defined in $R^{13}$ and $R^{14}$, respectively,
  $SiR^{33}R^{34}R^{35}$, wherein $R^{33}$, $R^{34}$, and $R^{35}$ are the same or different and are each as defined in $R^{11}$,
  xiv) a nitro group,
  xv a c group,
  xvi) a halogen atom, or
  xvii) a pentahalogenothio group;
n is an integer of 0 to 2;
$Z^7$ and $Z^8$ are the same or different and are —CH= or —N=;
$Z^9$ is —O—, —S—, or —N($R^4$)—, wherein $R^4$ is a hydrogen atom, a substituted or unsubstituted alkyl group, or may form a ring together with an adjacent carbon atom through —$(CH_2)_r$— (wherein r is an integer of 3 to 6);
Y is an aryl, aromatic heterocyclic, or dioxaborolanyl group which optionally comprises one to three substituents selected from the group consisting of:
  i) a substituted or unsubstituted alkyl group, cycloalkyl group, alkenyl group, alkynyl group, alicyclic heterocyclic group, alicyclic heterocyclic alkyl group,
  ii) $COR^{41}$, wherein $R^{41}$ is as defined in $R^{11}$,
  iii) $COOR^{42}$, wherein $R^{42}$ is as defined in $R^{11}$,
  iv) $C(=Q^3)NR^{43}R^{44}$, wherein $Q^3$ is as defined in $Q^1$, and $R^{43}$ and $R^{44}$ are the same or different and are as defined in $R^{13}$ and $R^{14}$, respectively,
  v) $OR^{45}$, wherein $R^{45}$ is as defined in $R^{11}$,
  vi) $OCOR^{46}$, wherein $R^{46}$ is as defined in $R^{11}$,
  vii) $S(O)qR^{47}$, wherein q is an integer of 0 to 3, and $R^{47}$ is as defined in $R^{11}$,
  viii) $SO_2NR^{48}R^{49}$, wherein $R^{48}$ and $R^{49}$ are the same or different and are as defined in $R^{13}$ and $R^{14}$, respectively,
  ix) $NR^{50}R^{51}$, wherein $R^{50}$ and $R^{51}$ are the same or different and are as defined in $R^{21}$ and $R^{22}$, respectively,
  x) $N(R^{52})C(=Q^4)NR^{53}R^{54}$, wherein $Q^4$ is as defined in $Q^2$ $R^{52}$ is as defined in $R^{11}$, $R^{53}$ and $R^{54}$ are the same or different and are as defined in $R^{13}$ and $R^{14}$, respectively,
  xi) $N(R^{55})SO_2NR^{56}R^{57}$, wherein $R^{55}$ is as defined in $R^{11}$, and $R^{56}$ and $R^{57}$ are the same or different and are as defined in $R^{13}$ and $R^{14}$, respectively,
  xii) $SiR^{58}R^{59}R^{60}$, wherein $R^{58}$, $R^{59}$, and $R^{60}$ are the same or different and are each as defined in $R^{11}$,
  xiii) a nitro group,
  xiv) a cyano group, and
  xv) a halogen atom.

6. The compound or salt of claim 5, wherein, in formula (Ic):
  $Z^7$ and $Z^8$ are —CH=; and
  $Z^9$ is —O—, and having a formula (Ica):

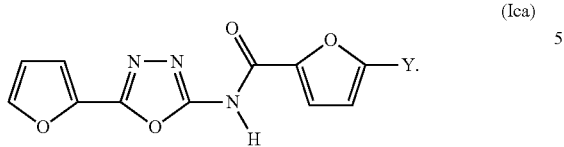

7. The compound or salt of claim 5, wherein, in formula (Ic):
$Z^7$ and $Z^8$ are —CH=; and
$Z^9$ is —S—, and
having a formula (Icb):

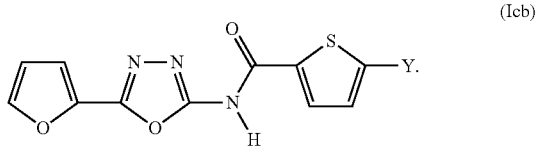

8. A 1,3,4-oxadiazole-2-carboxamide compound selected from the group consisting of:
- N-[5-(2-furyl)-1,3,4-oxadiazol-2-yl]-3-biphenylcarboxamide (Compound Ia-1);
- N-[5(2-furyl)-1,3,4-oxadiazol-2-yl]-2'-hydroxy-3-biphenyl carboxamide (Compound Ia-2);
- 2'-formyl-N-[5-(2-furyl)-1,3,4-oxadiazol-2-yl]-3-biphenylcarboxamide (Compound Ia-3);
- N-[5-(2-furyl)- 1,3,4-oxadiazol-2-yl]-3'-hydroxy-3-biphenylcarboxamide (Compound Ia-4);
- N-[5-(2-furyl)-1,3,4-oxadiazol-2-yl]-3'-nitro-3-biphenylcarboxamide (Compound Ia-5);
- 3'-formyl-N[5-(2-furyl)- 1,3,4-oxadiazol-2-yl]-3-biphenylcarboxamide (Compound Ia-6);
- N-[5-(2-furyl)-1,3,4-oxadiazol-2-yl]-3'-methoxycarbonyl-3-biphenylcarboxamide (Compound Ia-7);
- 3'-carboxy-N-[5-(2-furyl)-1,3,4-oxadiazol-2-yl]-3-biphenylcarboxamide (Compound Ia-8);
- 3'-cyano-N-[5-(2-furyl)-1,3,4-oxadiazol-2-yl]-3-biphenylcarboxamide (Compound Ia-9);
- 4'-fluoro-N-[5-(2-furyl)-1,3,4-oxadiazol-2-yl]-3-biphenylcarboxamide (Compound Ia-10);
- 4'-chloro-N-[5-(2-furyl)-1,3,4-oxadiazol-2-yl]-3-biphenylcarboxamide (Compound Ia-11);
- N-[5-(2-furyl)-1,3,4-oxadiazol-2-yl]-4'-methyl-3-biphenylcarboxamide (Compound Ia-12);
- N-[5-(2-furyl)-1,3,4-oxadiazol-2-yl]-4'-vinyl-3-biphenylcarboxamide (Compound Ia-13);
- 4'-tert-butyl-N-[5-(2-furyl)-1,3,4-oxadiazol-2-yl]-3-biphenylcarboxamide (Compound Ia-14);
- N-[5-(2-furyl)-1,3,4-oxadiazol-2-yl]-4'-hydroxy-3-biphenylcarboxamide (Compound Ia-15);
- N-[5-(2-furyl)-1,3,4-oxadiazol-2-yl]-4'-methoxy-3-biphenylcarboxamide (Compound Ia-16);
- 4'-formyl-N-[5-(2-furyl)-1,3,4-oxadiazol-2-yl]-3-biphenylcarboxamide (Compound Ia-17);
- 4'-acetyl-N-[5-(2-furyl)-1,3,4-oxadiazol-2-yl]-3-biphenylcarboxamide (Compound Ia-18);
- 4'-benzoyl-N-[5-(2-furyl)-1,3,4-oxadiazol-2-yl]-3-biphenylcarboxamide (Compound Ia-19);
- 4'-carbamoyl-N-[5-(2-furyl)-1,3,4-oxadiazol-2-yl]-3-biphenylcarboxamide (Compound Ia-20);
- 4'-cyano-N-[5-(2-furyl)-1,3,4-oxadiazol-2-yl]-3-biphenylcarboxamide (Compound Ia-21);
- 4'-cyanomethyl-N-[5-(2-furyl)-1,3,4-oxadiazol-2-yl]-3-biphenylcarboxamide (Compound Ia-22);
- 4'-n-butoxycarbonyl-N-[5-(2-furyl)-1,3,4-oxadiazol-2-yl]-3-biphenylcarboxamide (Compound Ia-23);
- N-[5-(2-furyl)-1,3,4-oxadiazol-2-yl]-4'-nitro-3-biphenylcarboxamide (Compound Ia-24);
- N-[5-(2-furyl)-1,3,4-oxadiazol-2-yl]-4'-sulfamoyl-3-biphenylcarboxamide (Compound Ia-25);
- N-[5-(2-furyl)-1,3,4-oxadiazol-2-yl]-4'-(N-methylsulfamoyl)-3-biphenylcarboxamide (Compound Ia-26);
- N-[5-(2-furyl)-1,3,4-oxadiazol-2-yl]-4'-(N,N-dimethylsulfamoyl)-3-biphenylcarboxamide (Compound Ia-27);
- N-[5-(2-furyl)-1,3,4-oxadiazol-2-yl]-4'-methanesulfonyl-3-biphenylcarboxamide (Compound Ia-28);
- 4'-cyano-N-[5-(2-furyl)-1,3,4-oxadiazol-2-yl]-2'-methyl-3-biphenylcarboxamide (Compound Ia-29);
- 4'-acetyl-3'-fluoro-N-[5-(2-furyl)-1,3,4-oxadiazol-2-yl]-3-biphenylcarboxamide (Compound Ia-30);
- N-[5-(2-furyl)-1,3,4-oxadiazol-2-yl]-4'-sulfamoyl-4-biphenylcarboxamide (Compound Ia-31);
- N-[5-(2-furyl)-1,3,4-oxadiazol-2-yl]-3-(1-naphthyl)benzenecarboxamide (Compound Ia-32);
- N-[5-(2-furyl)-1,3,4-oxadiazol-2-yl]-3-(2-naphthyl) benzenecarboxamide (Compound Ia-33);
- N-[5-(2-furyl)-1,3,4-oxadiazol-2-yl]-3-(5-methyl-2-furyl)benzenecarboxamide (Compound Ia-34);
- 3-(2-cyano-5-pyridyl)-N-[5-(2-furyl)-1,3,4-oxadiazol-2-yl]benzenecarboxamide (Compound Ia-35);
- N-[5-(2-furyl)-1,3,4-oxadiazol-2-yl]-3-(5-sulfamoyl-2-thienyl)benzenecarboxamide (Compound Ia-36);
- N-[5-(2-furyl)-1,3,4-oxadiazol-2-yl]-3-(3-pyridyl)benzenecarboxamide trifluoroacetate (Compound Ia-37);
- N-[5-(2-furyl)-1,3,4-oxadiazol-2-yl]-3-(2-hydroxy-5-pyridyl)benzenecarboxamide (Compound Ia-38);
- 3-(2-amino-5-pyridyl)-N-[5-(2-furyl)-1,3,4-oxadiazol-2-yl]benzenecarboxamide (Compound Ia-39);
- N-[5-(2-furyl)-1,3,4-oxadiazol-2-yl]-3-(2-methylthio-5-pyridyl)benzenecarboxamide (Compound Ia-40);
- N-[5-(2-furyl)-1,3,4-oxadiazol-2-yl]-3-(4-pyridyl)benzenecarboxamide (Compound Ia-41);
- N-[5-(2-furyl)-1,3,4-oxadiazol-2-yl]-3-(3,4-methylenedioxyphenyl)-benzenecarboxamide (Compound Ia-42);
- N-[5-(2-furyl)-1,3,4-oxadiazol-2-yl]-3-(1-methyl-6-indolyl)benzenecarboxamide (Compound Ia-43);
- N-[5-(2-furyl)-1,3,4-oxadiazol-2-yl]-3-(1-methyl-5-indolinyl)benzenecarboxamide (Compound Ia-44);
- N-[5-(2-furyl)-1,3,4-oxadiazol-2-yl]-3-(1-methyl-5-indazolyl)benzenecarboxamide (Compound Ia-45);
- N-[5-(2-furyl)-1,3,4-oxadiazol-2-yl]-3-(1-methyl-6-benzimidazolyl)-benzenecarboxamide (Compound Ia-46);
- 3-(5-benzothienyl)-N-[5-(2-furyl)-1,3,4-oxadiazol-2-yl] benzenecarboxamide (Compound Ia-47);
- 3-(5-benzothiazolyl)-N-[5-(2-furyl)-1,3,4-oxadiazol-2-yl]benzenecarboxamide (Compound Ia-48);
- N-[5-(2-furyl)-1,3,4-oxadiazol-2-yl]-3-[9-methyl-3-(9H-carbazolyl)]benzenecarboxamide (Compound Ia-49);
- N-[5-(2-furyl)-1,3,4-oxadiazol-2-yl]-3-(1-methyl-5-indolyl)benzenecarboxamide (Compound Ia-50);
- 2-fluoro-N-[5-(2-furyl)-1,3,4-oxadiazol-2-yl]-3-(1-methyl-5-indolyl)benzenecarboxamide (Compound Ia-51);
- 5-fluoro-N-[5-(2-furyl)-1,3,4-oxadiazol-2-yl]-3-(1-methyl-5-indolyl)benzenecarboxamide (Compound Ia-52);

2-fluoro-N-[5-(2-furyl)-1,3,4-oxadiazol-2-yl]-5-(1-methyl-5-indolyl)benzenecarboxamide (Compound Ia-53);
N-[5-(2-furyl)-1,3,4-oxadiazol-2-yl]-2-phenyl-4-pyridinecarboxamide (Compound Ia-54);
N-[5-(2-furyl)-1,3,4-oxadiazol-2-yl]-2,6-diphenyl-4-pyridinecarboxamide (Compound Ia-55);
2-(4-bromophenyl)-6-(4-chlorophenyl)-N-[5-(2-furyl)-1,3,4-oxadiazol-2-yl]-4-pyridinecarboxamide (Compound Ia-56);
N-[5-(2-furyl)-1,3,4-oxadiazol-2-yl]-2-phenyl-5-pyridinecarboxamide (Compound Ia-57);
N-[5-(2-furyl)-1,3,4-oxadiazol-2-yl]-5-(1-methyl-5-indolyl)-3-pyridinecarboxamide (Compound Ia-58);
4'-cyano-3'-fluoro-N-[5-(2-furyl)-1,3,4-oxadiazol-2-yl]-3-biphenylcarboxamide (Compound Ia-59);
4'-(2-cyano-2-propyl)-N-[5-(2-furyl)-1,3,4-oxadiazol-2-yl]-3-biphenylcarboxamide (Compound Ia-60);
4'-tert-butyl-N-[5-(2-furyl)-1,3,4-oxadiazol-2-yl]-3$^1$-nitro-3-biphenylcarboxamide (Compound Ia-61);
N-[5-(2-furyl)-1,3,4-oxadiazol-2-yl]-4'-trimethylsilyl-3-biphenylcarboxamide (Compound Ia-62);
N-[5-(2-furyl)-1,3,4-oxadiazol-2-yl]-4'-trifluoromethyl-3-biphenylcarboxamide (Compound Ia-63);
N-[5-(2-furyl)-1,3,4-oxadiazol-2-yl]-4'-trifluoromethoxy-3-biphenylcarboxamide (Compound Ia-64);
4'-benzyl-N-[5-(2-furyl)-1,3,4-oxadiazol-2-yl]-3-biphenylcarboxamide (Compound Ia-65);
N-[5-(2-furyl)-1,3,4-oxadiazol-2-yl]-4'-phenoxy-3-biphenylcarboxamide (Compound Ia-66);
4'-diphenylamino-N-[5-(2-furyl)-1,3,4-oxadiazol-2-yl]-3-biphenylcarboxamide (Compound Ia-67);
N-[5-(2-furyl)-1,3,4-oxadiazol-2-yl]-4'-ureido-3-biphenylcarboxamide (Compound Ia-68);
N-[5-(2-furyl)-1,3,4-oxadiazol-2-yl]-4'-methoxycarbonyl-3-biphenylcarboxamide (Compound Ia-69);
N-[5-(2-furyl)-1,3,4-oxadiazol-2-yl]-4'-propionyl-3-biphenylcarboxamide (Compound Ia-70);
N-[5-(2-furyl)-1,3,4-oxadiazol-2-yl]-4'-piperidinosulfonyl-3-biphenylcarboxamide (Compound Ia-71);
N-[5-(2-furyl)-1,3,4-oxadiazol-2-yl]-4'-sulfo-3-biphenylcarboxamide (Compound Ia-72);
N-[5-(2-furyl)-1,3,4-oxadiazol-2-yl]-3-(o-terphenyl)carboxamide (Compound Ia-73);
N-[5-(2-furyl)-1,3,4-oxadiazol-2-yl]-3-(m-terphenyl)carboxamide (Compound Ia-74);
N-[5-(2-furyl)-1,3,4-oxadiazol-2-yl]-3-(p-terphenyl)carboxamide (Compound Ia-75);
3'-fluoro-N-[5-(2-furyl)-1,3,4-oxadiazol-2-yl]-3-(p-terphenyl)carboxamide (Compound Ia-76);
4"-chloro-N-[5-(2-furyl)-1,3,4-oxadiazol-2-yl]-3-(p-terphenyl)carboxamide (Compound Ia-77);
4"-ethyl-N-[5-(2-furyl)-1,3,4-oxadiazol-2-yl]-3-(p-terphenyl)carboxamide (Compound Ia-78);
4"-ethoxy-N-[5-(2-furyl)-1,3,4-oxadiazol-2-yl]-3-(p-terphenyl)carboxamide (Compound Ia-79);
N-[5-(2-furyl)-1,3,4-oxadiazol-2-yl]-4"-propoxy-3-(p-terphenyl)carboxamide (Compound Ia-80);
N-[5-(2-furyl)-1,3,4-oxadiazol-2-yl]-4"-isopropoxy-3-(p-terphenyl)carboxamide (Compound Ia-81);
N-[5-(2-furyl)-1,3,4-oxadiazol-2-yl]-4'-(1-naphthyl)-3-biphenylcarboxamide (Compound Ia-82);
N-[5-(2-furyl)-1,3,4-oxadiazol-2-yl]-4'-(2-naphthyl)-3-biphenylcarboxamide (Compound Ia-83);
4'-cyclohexyl-N-[5-(2-furyl)-1,3,4-oxadiazol-2-yl]-3-biphenylcarboxamide (Compound Ia-84);
N-[5-(2-furyl)-1,3,4-oxadiazol-2-yl]-4'-(trans-4-n-propylcyclohexyl)-3-biphenylcarboxamide (Compound Ia-85);
N-[5-(2-furyl)-1,3,4-oxadiazol-2-yl]-3'-morpholino-3-biphenylcarboxamide (Compound 1a-86);
N-[5-(2-furyl)-1,3,4-oxadiazol-2-yl]-4'-morpholino-3-biphenylcarboxamide (Compound Ia-87);
4'-(4-tert-butoxycarbonyl-1-piperazinyl)-N-[5-(2-furyl)-1,3,4-oxadiazol-2-yl]-3-biphenylcarboxamide (Compound Ia-88);
N-[5-(2-furyl)-1,3,4-oxadiazol-2-yl]-4'-(1-piperazinyl)-3-biphenylcarboxamide (Compound Ia-89);
N-[5-(2-furyl)-1,3,4-oxadiazol-2-yl]-4'-(2-morpholinoethyl)-3-biphenylcarboxamide (Compound Ia-90);
N-[5-(2-furyl)-1,3,4-oxadiazol-2-yl]-3-(2-pyridyl)benzenecarboxamide (Compound Ia-91);
3-(2-cyano-5-pyridyl)-N-[5-(2-furyl)-1,3,4-oxadiazol-2-yl]benzenecarboxamide (Compound Ia-92);
N-[5-(2-furyl)-1,3,4-oxadiazol-2-yl]-3-(2-trifluoromethyl-5-pyridyl)benzenecarboxamide (Compound Ia-93);
N-[5-(2-furyl)-1,3,4-oxadiazol-2-yl]-3-(2-morpholino-3-pyridyl)benzenecarboxamide (Compound Ia-94);
N-[5-(2-furyl)-1,3,4-oxadiazol-2-yl]-3-(2-morpholino-4-pyridyl)benzenecarboxamide (Compound Ia-95);
N-[5-(2-furyl)-1,3,4-oxadiazol-2-yl]-3-[2-(1-piperazinyl)-5-pyridyl]benzenecarboxamide (Compound Ia-96);
N-[5-(2-furyl)-1,3,4-oxadiazol-2-yl]-3-(5-phenyl-2-thienyl)benzenecarboxamide (Compound Ia-97);
N-[5-(2-furyl)-1,3,4-oxadiazol-2-yl]-3-(2-morpholino-5-pyrimidinyl)benzenecarboxamide (Compound Ia-98);
N-[5-(2-furyl)-1,3,4-oxadiazol-2-yl]-3-(3-quinolyl)benzenecarboxamide (Compound Ia-99);
N-[5-(2-furyl)-1,3,4-oxadiazol-2-yl]-3-(6-quinoxalinyl)benzenecarboxamide (Compound Ia-100);
3-(5-benzofurazanyl)-N-[5-(2-furyl)-1,3,4-oxadiazol-2-yl]benzenecarboxamide (Compound Ia-101);
3-(3,4-ethylenedioxyphenyl)-N-[5-(2-furyl)-1,3,4-oxadiazol-2-yl]benzenecarboxamide (Compound Ia-102);
N-[5-(2-furyl)-1,3,4-oxadiazol-2-yl]-3-(4-methyl-1-naphthyl)benzenecarboxamide (Compound Ia-103);
3-(2-ethoxy-1-naphthyl)-N-[5-(2-furyl)-1,3,4-oxadiazol-2-yl]benzenecarboxamide (Compound Ia-104);
3-(4-fluoro-1-naphthyl)-N-[5-(2-furyl)-1,3,4-oxadiazol-2-yl]benzenecarboxamide (Compound Ia-105);
N-[5-(2-furyl)-1,3,4-oxadiazol-2-yl]-3-(3-methoxy-2-naphthyl)benzenecarboxamide (Compound Ia-106);
N-[5-(2-furyl)-1,3,4-oxadiazol-2-yl]-3-(6-methoxy-2-naphthyl)benzenecarboxamide (Compound Ia-107);
3-(6-ethoxy-2-naphthyl)-N-[5-(2-furyl)-1,3,4-oxadiazol-2-yl]benzenecarboxamide (Compound Ia-108);
3-(6-benzyloxy-2-naphthyl)-N-[5-(2-furyl)-1,3,4-oxadiazol-2-yl]benzenecarboxamide (Compound Ia-109);
3-(9-anthryl)-N-[5-(2-furyl)-1,3,4-oxadiazol-2-yl]benzenecarboxamide (Compound Ia-110);
3-(5-acenaphthenyl)-N-[5-(2-furyl)-1,3,4-oxadiazol-2-yl]benzenecarboxamide (Compound Ia-111);
N-[5-(2-furyl)-1,3,4-oxadiazol-2-yl]-3-(4,4,5,5-tetramethyl-1,3,2-dioxaborolane-2-yl)benzenecarboxamide (Compound Ia-112);
4"-ethyl-2-fluoro-N-[5-(2-furyl)-1,3,4-oxadiazol-2-yl]-3-(p-terphenyl)carboxamide (Compound Ia-113);
4"-ethyl-4-fluoro-N-[5-(2-furyl)-1,3,4-oxadiazol-2-yl]-3-(p-terphenyl)carboxamide (Compound Ia-114);
4"-ethyl-N-[5-(2-furyl)-1,3,4-oxadiazol-2-yl]-4-methyl-3-(p-terphenyl)carboxamide (Compound Ia-115);

4"-ethyl-5-fluoro-N-[5-(2-furyl)-1,3,4-oxadiazol-2-yl]-3-(p-terphenyl)carboxamide (Compound Ia-116);
6-(4-biphenylyl)-N-[5-(2-furyl)-1,3,4-oxadiazol-2-yl]-2-pyridinecarboxamide (Compound Ia-117);
6-(4'-ethyl-4-biphenylyl)-N-[5-(2-furyl)-1,3,4-oxadiazol-2-yl]-2-pyridinecarboxamide (Compound Ia-118);
5-(4-biphenylyl)-N-[5-(2-furyl)-1,3,4-oxadiazol-2-yl]-3-pyridinecarboxamide (Compound Ia-119);
5-(4'-ethyl-4-biphenylyl)-N-[5-(2-furyl)-1,3,4-oxadiazol-2-yl]-3-pyridinecarboxamide (Compound Ia-120);
4'-bromo-N-[5-(2-furyl)-1,3,4-oxadiazol-2-yl]1-3-biphenylcarboxamide (Compound Ia-121);
2"-fluoro-N-[5-(2-furyl)-1,3,4-oxadiazol-2-yl]-3-(p-terphenyl)carboxamide (Compound Ia-122);
2"-chloro-N-[5-(2-furyl)-1,3,4-oxadiazol-2-yl]-3-(p-terphenyl)carboxamide (Compound Ia-123);
N-[5-(2-furyl)-1,3,4-oxadiazol-2-yl]-2"-methyl-3-(p-terphenyl)carboxamide (Compound Ia-124);
N-[5-(2-furyl)-1,3,4-oxadiazol-2-yl]-2"-methoxy-3-(p-terphenyl)carboxamide (Compound Ia-125);
N-[5-(2-furyl)-1,3,4-oxadiazol-2-yl]-2"-trifluoromethyl-3-(p-terphenyl)carboxamide (Compound Ia-126);
N-[5-(2-furyl)-1,3,4-oxadiazol-2-yl]-2"-trifluoromethoxy-3-(p-terphenyl)carboxamide (Compound Ia-127);
2"-cyano-N-[5-(2-furyl)-1,3,4-oxadiazol-2-yl]-3-(p-terphenyl)carboxamide (Compound Ia-128);
N-[5-(2-furyl)-1,3,4-oxadiazol-2-yl]-3-(1,1':4',1":2",1'"-quaterphenyl)carboxamide (Compound Ia-129);
3"-fluoro-N-[5-(2-furyl)-1,3,4-oxadiazol-2-yl]-3-(p-terphenyl)carboxamide (Compound Ia-130);
3"-chloro-N-[5-(2-furyl)-1,3,4-oxadiazol-2-yl]-3-(p-terphenyl)carboxamide (Compound Ia-131);
N-[5-(2-furyl)-1,3,4-oxadiazol-2-yl]-3"-methyl-3-(p-terphenyl)carboxamide (Compound Ia-132);
N-[5-(2-furyl)-1,3,4-oxadiazol-2-yl]-3"-methoxy-3-(p-terphenyl)carboxamide (Compound Ia-133);
N-[5-(2-furyl)-1,3,4-oxadiazol-2-yl]-3"-trifluoromethyl-3-(p-terphenyl)carboxamide (Compound Ia-134);
N-[5-(2-furyl)-1,3,4-oxadiazol-2-yl]-3"-trifluoromethoxy-3-(p-terphenyl)carboxamide (Compound Ia-135);
3"-cyano-N-[5-(2-furyl)-1,3,4-oxadiazol-2-yl]-3-(p-terphenyl)carboxamide (Compound Ia-136);
N-[5-(2-furyl)-1,3,4-oxadiazol-2-yl]3-(1,1':4',1":3",1'"-quaterphenyl)carboxamide (Compound Ia-137);
4"-fluoro-N-[5-(2-furyl)-1,3,4-oxadiazol-2-yl]-3-(p-terphenyl)carboxamide (Compound Ia-138);
N-[5-(2-furyl)-1,3,4-oxadiazol-2-yl]-4"-methyl-3-(p-terphenyl)carboxamide (Compound Ia-139);
N-[5-(2-furyl)-1,3,4-oxadiazol-2-yl]-4"-methoxy-3-(p-terphenyl)carboxamide (Compound Ia-140);
N-[5-(2-furyl)-1,3,4-oxadiazol-2-yl]-4"-trifluoromethyl-3-(p-terphenyl)carboxamide (Compound Ia-141);
N-[5-(2-furyl)-1,3,4-oxadiazol-2-yl]1-4"-trifluoromethoxy-3-(p-terphenyl)carboxamide (Compound Ia-142);
4"-cyano-N-[5-(2-furyl)-1,3,4-oxadiazol-2-yl]-3-(p-terphenyl)carboxamide (Compound Ia-143);
N-[5-(2-furyl)-1,3,4-oxadiazol-2-yl]-3-(1,1':4',1"4",1'"-quaterphenyl)carboxamide (Compound Ia-144);
N-[5-(2-furyl)-1,3,4-oxadiazol-2-yl]-4"-trimethylsilyl-3-(p-terphenyl)carboxamide (Compound Ia-145);
4'-(1-cyclohexenyl)-N-[5-(2-furyl)-1,3,4-oxadiazol-2-yl]-3-biphenylcarboxamide (Compound Ia-146);
4'-(4,4-dimethyl-1-cyclohexenyl)-N-[5-(2-furyl)-1,3,4-oxadiazol-2-yl]-3-biphenylcarboxamide (Compound Ia-147);
4'-(4-tert-butyl-1-cyclohexenyl)-N-[5-(2-furyl)-1,3,4-oxadiazol-2-yl]-3-biphenylcarboxamide (Compound Ia-148);
N-[5-(2-furyl)-1,3,4-oxadiazol-2-yl]-4'-(2,2,6,6-tetramethyl-3,6-dihydro-4-pyranyl)-3-biphenylcarboxamide (Compound Ia-149);
N-[5-(2-furyl)-1,3,4-oxadiazol-2-yl]-4'-(1-methyl -1,2,3,6-tetrahydro-4-pyridyl)-3-biphenylcarboxamide (Compound Ia-150);
4'-(2-furyl)-N-[5-(2-furyl)-1,3,4-oxadiazol-2-yl]-3-biphenylcarboxamide (Compound Ia-151);
N-[5-(2-furyl)-1,3,4-oxadiazol-2-yl]-4'-(2-thienyl)-3-biphenylcarboxamide (Compound Ia-152);
N-[5-(2-furyl)-1,3,4-oxadiazol-2-yl]-4'-(3-thienyl)-3-biphenylcarboxamide (Compound Ia-153);
N-[5-(2-furyl)-1,3,4-oxadiazol-2-yl]-4'-(1-methyl-4-pyrazolyl)-3-biphenylcarboxamide (Compound Ia-154);
N-[5-(2-furyl)-1,3,4-oxadiazol-2-yl]-4'-(4-pyridyl)-3-biphenylcarboxamide (Compound Ia-155);
N-[5-(2-furyl)-1,3,4-oxadiazol-2-yl]-4'-(1-methyl-5-indolyl)-3-biphenylcarboxamide (Compound Ia-156);
N-[5-(2-furyl)-1,3,4-oxadiazol-2-yl]-3"-hydroxy-3-(p-terphenyl)carboxamide (Compound Ia-157);
N-[5-(2-furyl)-1,3,4-oxadiazol-2-yl]-4"-(1-propyl)-3-(p-terphenyl)carboxamide (Compound Ia-158);
N-[5-(2-furyl)-1,3,4-oxadiazol-2-yl]-4"-isopropyl-3-(p-terphenyl)carboxamide (Compound Ia-159);
4"-(1-butyl)-N-[5-(2-furyl)-1,3,4-oxadiazol-2-yl]-3-(p-terphenyl)carboxamide (Compound Ia-160);
4"-tert-butyl-N-[5-(2-furyl)-1,3,4-oxadiazol-2-yl]-3-(p-terphenyl)carboxamide (Compound Ia-161);
N-[5-(2-furyl)-1,3,4-oxadiazol-2-yl]-4"-hydroxy-3-(p-terphenyl)carboxamide (Compound Ia-162);
4"-(N,N-dimethylamino)-N-[5-(2-furyl)-1,3,4-oxadiazol-2-yl]-3-(p-terphenyl)carboxamide (Compound Ia-163);
N-[5-(2-furyl)-1,3,4-oxadiazol-2-yl]-4"-methanesulfonyl-3-(p-terphenyl)carboxamide (Compound Ia-164);
N-[5-(2-furyl)-1,3,4-oxadiazol-2-yl]-4"-sulfamoyl-3-(p-terphenyl)carboxamide (Compound Ia-165);
5-chloro-4"-ethyl-N-[5-(2-furyl)-1,3,4-oxadiazol-2-yl]-3-(p-terphenyl)carboxamide (Compound Ia-166);
4"-ethyl-N-[5-(2-furyl)-1,3,4-oxadiazol-2-yl]-5-nitro-3-(p-terphenyl)carboxamide (Compound Ia-167);
5-acetylamino-4"-ethyl-N-[5-(2-furyl)-1,3,4-oxadiazol-2-yl]-3-(p-terphenyl)carboxamide (Compound Ia-168);
4"-ethyl-N-[5-(2-furyl)-1,3,4-oxadiazol-2-yl]-5-trifluoromethyl-3-(p-terphenyl)carboxamide (Compound Ia-169);
4"-ethyl-N-[5-(2-furyl)-1,3,4-oxadiazol-2-yl]-5-trifluoromethoxy-3-(p-terphenyl)carboxamide (Compound Ia-170);
5-cyano-4"-ethyl-N-[5-(2-furyl)-1,3,4-oxadiazol-2-yl]-3-(p-terphenyl)carboxamide (Compound Ia-171);
4"-ethyl-N-[5-(2-furyl)-1,3,4-oxadiazol-2-yl]-5-pentafluorothio-3-(p-terphenyl)carboxamide (Compound Ia-172);
N-[5-(2-furyl)-1,3,4-oxadiazol-2-yl]-5-phenyl-2-piperidino-7-thiazolo[4,5-b]pyridinecarboxamide (Compound Ib-1);
5-(3-chlorophenyl)-N-[5-(2-furyl)-1,3,4-oxadiazol-2-yl]-2-piperidino-7-thiazolo[4,5-b]pyridinecarboxamide (Compound Ib-2);

N-[5-(2-furyl)-1,3,4-oxadiazol-2-yl]-5-(4-methylphenyl)-2-piperidino-7-thiazolo[4,5-b]pyridinecarboxamide (Compound Ib-3);

N-[5-(2-furyl)-1,3,4-oxadiazol-2-yl]-5-(3,4-dimethoxyphenyl)-2-piperidino-7-thiazolo[4,5-b]pyridinecarboxamide (Compound Ib-4);

N-[5-(2-furyl)-1,3,4-oxadiazol-2-yl]-3-methyl-6-phenyl-4-benzo[d]isoxazolecarboxamide (Compound Ib-5);

N-[5-(2-furyl)-1,3,4-oxadiazol-2-yl]-5-(2-naphthyl)-2-piperidino-7-thiazolo[4,5-b]pyridinecarboxamide (Compound Ib-6);

N-[5-(2-furyl)-1,3,4-oxadiazol-2-yl]-2-(4-methylpiperidino)-5-phenyl-7-thiazolo[4,5-b]pyridinecarboxamide (Compound Ib-7);

5-phenyl-N-(5-phenyl-1,3,4-oxadiazol-2-yl)-2-piperidino-7-thiazolo[4,5-b]pyridinecarboxamide (Compound Ib-8);

N-[5-(2-chlorophenyl)-1,3,4-oxadiazol-2-yl]-5-phenyl-2-piperidino-7-thiazolo[4,5-b]pyridinecarboxamide (Compound Ib-9);

N-[5-(4-chlorophenyl)-1,3,4-oxadiazol-2-yl]-5-phenyl-2-piperidino-7-thiazolo[4,5-b]pyridinecarboxamide (Compound Ib-10);

N-[5-(4-methoxyphenyl)-1,3,4-oxadiazol-2-yl]-5-phenyl-2-piperidino-7-thiazolo[4,5-b]pyridinecarboxamide (Compound Ib-11);

N-[5-(4-nitrophenyl)-1,3,4-oxadiazol-2-yl]-5-phenyl-2-piperidino-7-thiazolo[4,5-b]pyridinecarboxamide (Compound Ib-12);

N-(5-benzyl-1,3,4-oxadiazol-2-yl)-5-phenyl-2-piperidino-7-thiazolo[4,5-b]pyridinecarboxamide (Compound Ib-13);

N-[5-(2-methyl-3-furyl)-1,3,4-oxadiazol-2-yl]-5-phenyl-2-piperidino-7-thiazolo[4,5-b]pyridinecarboxamide (Compound Ib-14);

N-[5-(2,5-dimethyl-3-furyl)-1,3,4-oxadiazol-2-yl]-5-phenyl-2-piperidino-7-thiazolo[4,5-b]pyridinecarboxamide (Compound Ib-15);

5-phenyl-2-piperidino-N-[5-(2-thienyl)-1,3,4-oxadiazol-2-yl]-7-thiazolo[4,5-b]pyridinecarboxamide (Compound Ib-16);

N-[5-(3-methyl-2-thienyl)-1,3,4-oxadiazol-2-yl]-5-phenyl-2-piperidino-7-thiazolo[4,5-b]pyridinecarboxamide (Compound Ib-17);

N-[5-(5-methyl-2-thienyl)-1,3,4-oxadiazol-2-yl]-5-phenyl-2-piperidino-7-thiazolo[4,5-b]pyridinecarboxamide (Compound Ib-18);

5-phenyl-2-piperidino-N-[5-(3-thienyl)-1,3,4-oxadiazol-2-yl]-7-thiazolo[4,5-b]pyridinecarboxamide (Compound Ib-19);

N-[5-(5-isoxazolyl)-1,3,4-oxadiazol-2-yl]-5-phenyl-2-piperidino-7-thiazolo[4,5-b]pyridineearboxamide (Compound Ib-20);

N-[5-(1-methyl-3-pyrazolyl)-1,3,4-oxadiazol-2-yl]-5-phenyl-2-piperidino-7-thiazolo[4,5-b]pyridinecarboxamide (Compound Ib-21);

N-[5-(2,4-dimethyl-5-thiazolyl)-1,3,4-oxadiazol-2-yl]-5-phenyl-2-piperidino-7-thiazolo[4,5-b]pyridinecarboxamide (Compound Ib-22);

N-[5-(3-pyridyl)-1,3,4-oxadiazol-2-yl]-5-phenyl-2-piperidino-7-thiazolo[4,5-b]pyridinecarboxamide (Compound Ib-23);

N-{5-[(2,3-dihydrobenzo[1,4]dioxinyl)]-1,3,4-oxadiazol-2-yl}-5-phenyl-2-piperidino-7-thiazolo[4,5-b]pyridinecarboxamide (Compound Ib-24);

5-phenyl-2-piperidino-N-{5-[2-(4,5,6,7-tetrahydrobenzothienyl)]-1,3 ,4-oxadiazol-2-yl}-7-thiazolo[4,5-b]pyridinecarboxamide (Compound Ib-25);

N-[5-(2-furyl)-1,3,4-oxadiazol-2-yl]-2-(1-pyrrolidinyl)-5-(2-thienyl)-7-thiazolo[4,5-b]pyridinecarboxamide (Compound Ib-26);

N-[5-(2-furyl)-1,3,4-oxadiazol-2-yl]-2-piperidino-5-(2-thienyl)-7-thiazolo[4,5-b]pyridinecarboxamide (Compound Ib-27);

N-[5-(2-furyl)-1,3,4-oxadiazol-2-yl]-2-morpholino-5-(2-thienyl)-7-thiazolo[4,5-b]pyridinecarboxamide (Compound Ib-28);

N-[5-(2-furyl)-1,3,4-oxadiazol-2-yl]-2-(1-pyrrolidinyl)-5-(3-pyridyl)-7-thiazolo[4,5-b]pyridinecarboxamide (Compound Ib-29);

N-[5-(2-furyl)-1,3,4-oxadiazol-2-yl]-5-phenyl-2-(4-thiomorpholinyl)-7-thiazolo[4,5-b]pyridinecarboxamide (Compound Ib-30);

N-[5-(2-furyl)-1,3,4-oxadiazol-2-yl]-2-(1-methyl-4-piperazinyl)-5-phenyl-7-thiazolo[4,5-b]pyridinecarboxamide (Compound Ib-31);

2-(4,4-difluoropiperidino)-N-[5-(2-furyl)-1,3,4-oxadiazol-2-yl]-5-phenyl-7-thiazolo[4,5-b]pyridinecarboxamide (Compound Ib-32);

(dl)-N-[5-(2-furyl)-1,3,4-oxadiazol-2-yl]-2-(2-methylpiperidino)-5-phenyl-7-thiazolo[4,5-b]pyridinecarboxamide (Compound Ib-33);

(dl)-N-[5-(2-furyl)-1,3,4-oxadiazol-2-yl]-5-phenyl-2-(3-trifluoromethylpiperidino)-7-thiazolo[4,5-b]pyridinecarboxamide (Compound Ib-34);

N-[5-(2-furyl)-1,3,4-oxadiazol-2-yl]-5-phenyl-2-(4-trifluoromethylpiperidino)-7-thiazolo[4,5-b]pyridinecarboxamide (Compound Ib-35);

2-(4-cyanopiperidino)-N-[5-(2-furyl)-1,3,4-oxadiazol-2-yl]-5-phenyl-7-thiazolo[4,5-b]pyridinecarboxamide (Compound Ib-36);

N-[5-(2-furyl)-1,3,4-oxadiazol-2-yl]-2-morpholino-5-phenyl-7-thiazolo[4,5-b]pyridinecarboxamide (Compound Ib-37);

2-(1-azetidinyl)-N-[5-(2-furyl)-1,3,4-oxadiazol-2-yl]1-5-phenyl-7-thiazolo[4,5-b]pyridinecarboxamide (Compound Ib-38);

N-[5-(2-furyl)-1,3,4-oxadiazol-2-yl]-5-phenyl-2-(1-pyrrolidinyl)-7-thiazolo[4,5-b]pyridinecarboxamide (Compound Ib-39);

N-[5-(2-furyl)-1,3,4-oxadiazol-2-yl]-5-phenyl-2-(1,2,3,4-tetrahydro-1-quinolyl)-7-thiazolo[4,5-b]pyridinecarboxamide (Compound Ib-40);

2-acetylamino-N-[5-(2-furyl)-1,3,4-oxadiazol-2-yl]-5-phenyl-7-thiazolo[4,5-b]pyridinecarboxamide (Compound Ib-41);

2-tert-butoxycarbonylamino-N-[5-(2-furyl)-1,3,4-oxadiazol-2-yl]-5-phenyl-7-thiazolo[4,5-b]pyridinecarboxamide (Compound Ib-42);

N-[5-(2-furyl)-1,3,4-oxadiazol-2-yl]-2-(N-methylanilino)-5-phenyl-7-thiazolo[4,5-b]pyridinecarboxamide (Compound Ib-43);

N-[5-(2-furyl)-1,3,4-oxadiazol-2-yl]-2-(4-hydroxypiperidino)-5-phenyl-7-thiazolo[4,5-b]pyridinecarboxamide (Compound Ib-44);

N-[5-(2-furyl)-1,3,4-oxadiazol-2-yl]-5-phenyl-2-(4-phenylpiperidino)-7-thiazolo[4,5-b]pyridinecarboxamide (Compound Ib-45);

N-[5-(2-furyl)-1,3,4-oxadiazol-2-yl]-5-phenyl-2-(4-piperidinopiperidino)-7-thiazolo[4,5-b]pyridinecarboxamide (Compound Ib-46);

2-(2,2-dimethylmorpholino)-N-[5-(2-furyl)-1,3,4-oxadiazol-2-yl]-5-phenyl-7-thiazolo[4,5-b]pyridinecarboxamide (Compound Ib-47);

(dl)-2-[2(2-azabicyclo[2.2.1]heptyl]-N-[5-(2-furyl)-1,3,4-oxadiazol-2-yl]-5-phenyl-7-thiazolo[4,5-b]pyridinecarboxamide (Compound Ib-48);

2-[N-methyl-N-(3,3,3-trifluoro-1-propypamino]-N-[5-(2-furyl)-1,3,4-oxadiazol-2-yl]-5-phenyl-7-thiazolo[4,5-b]pyridinecarboxamide (Compound Ib-49);

2-(N,N-dimethylamino)-N-[5-(2-furyl)-1,3,4-oxadiazol-2-yl]-5-phenyl-7-thiazolo[4,5-b]pyridinecarboxamide (Compound Ib-50);

2-amino-N-[5-(2-furyl)-1,3,4-oxadiazol-2-yl]-5-phenyl-7-thiazolo[4,5-b]pyridinecarboxamide (Compound Ib-51);

N-[5-(2-furyl)-1,3,4-oxadiazol-2-yl]-5-phenyl-2-furancarboxamide (Compound Ic-1);

5-(2-fluorophenyl)-N-[5-(2-furyl)-1,3,4-oxadiazol-2-yl]-2-furancarboxamide (Compound Ic-2);

N-[5-(2-furyl)-1,3,4-oxadiazol-2-yl]-5-(2-nitrophenyl)-2-furancarboxamide (Compound Ic-3);

5-(3-chlorophenyl)-N-[5-(2-furyl)-1,3,4-oxadiazol-2-yl]-2-furancarboxamide (Compound Ic-4);

N-[5-(2-furyl)-1,3,4-oxadiazol-2-yl]-5-(3-nitrophenyl)-2-furancarboxamide (Compound Ic-5);

5-(4-fluorophenyl)-N-[5-(2-furyl)-1,3,4-oxadiazol-2-yl]-2-furancarboxamide (Compound Ic-6);

5-(4-chlorophenyl)-N-[5-(2-furyl)-1,3,4-oxadiazol-2-yl]-2-furancarboxamide (Compound Ic-7);

N-[5-(2-furyl)-1,3,4-oxadiazol-2-yl]-5-(4-methoxyphenyl)-2-furancarboxamide (Compound Ic-8);

5-(4-aminophenyl)-N-[5-(2-furyl)-1,3,4-oxadiazol-2-yl]-2-furancarboxamide (Compound Ic-9);

5-(4-acetylaminophenye-N-[5-(2-furyl)-1,3,4-oxadiazol-2-yl]-2-furancarboxamide (Compound Ic-10);

N-[5-(2-furyl)-1,3,4-oxadiazol-2-yl]-5-(4-nitrophenyl)-2-furancarboxamide (Compound Ic-11);

5-(4-ethoxycarbonylphenyl)-N-[5-(2-furyl)-1,3,4-oxadiazol-2-yl]-2-furancarboxamide (Compound Ic-12);

5-(2,4-dichlorophenyl)-N-[5-(2-furyl)-1,3,4-oxadiazol-2-yl]-2-furancarboxamide (Compound Ic-13);

5-(2-chloro-4-nitrophenyl)-N-[5-(2-furyl)-1,3,4-oxadiazol-2-yl]-2-furancarboxamide (Compound Ic-14);

5-(4-amino-2-methylphenyl)-N-[5-(2-furyl)-1,3,4-oxadiazol-2-yl]-2-furancarboxamide (Compound Ic-15);

5-(4-acetylamino-2-methylphenyl)-N-[5-(2-furyl)-1,3,4-oxadiazol-2-yl]-2-furancarboxamide (Compound Ic-16);

N-[5-(2-furyl)-1,3,4-oxadiazol-2-yl]-5-(2-methyl-4-nitrophenyl)-2-furancarboxamide (Compound Ic-17);

N-[5-(2-furyl)-1,3,4-oxadiazol-2-yl]-5-(2-methoxy-4-nitrophenyl)-2-furancarboxamide (Compound Ic-18);

5-(2-chloro-5-nitrophenyl)-N-[5-(2-furyl)-1,3,4-oxadiazol-2-yl]-2-furancarboxamide (Compound Ic-19);

5-(4-chloro-3-nitrophenye-N-[5-(2-furyl)-1,3,4-oxadiazol-2-yl]-2-furancarboxamide (Compound Ic-20);

5-(3,5-dichlorophenyl)-N-[5-(2-furyl)-1,3,4-oxadiazol-2-yl]-2-furancarboxamide (Compound Ic-21);

N-[5-(2-furyl)-1,3,4-oxadiazol-2-yl]-2-methyl-5-phenyl-3-furancarboxamide (Compound Ic-22);

N-[5-(2-furyl)-1,3,4-oxadiazol-2-yl]-5-phenyl-2-thiophenecarboxamide (Compound Ic-23);

5-(4-cyanophenyl)-N-[5-(2-furyl)-1,3,4-oxadiazol-2-yl]-2-thiophenecarboxamide (Compound Ic-24);

N-[5-(2-furyl)-1,3,4-oxadiazol-2-yl]-3-phenyl-1-(6,7,8,9-tetrahydro-5H-imidazo[1,5-a]azepinecarboxamide (Compound Ic-25);

3-(4-fluorophenyl)-N-[5-(2-furyl)-1,3,4-oxadiazol-2-yl]-1-(6,7,8,9-tetrahydro-5H-imidazo[1,5-a]azepinecarboxamide (Compound Ic-26);

4-(4-biphenylyl)-N-[5-(2-furyl)-1,3,4-oxadiazol-2-yl]-2-thiophenecarboxamide (Compound Ic-27);

4-(4'-ethyl-4-biphenylyl)-N-[5-(2-furyl)-1,3,4-oxadiazol-2-yl]-2-thiophenecarboxamide (Compound Ic-28); and 5-(4-carboxyphenyl)-N-[5-(2-furyl)-1,3,4-oxadiazol-2-yl]-2-furancarboxamide (Compound Ic-29), or a pharmaceutically acceptable salt thereof.

9. A medicine, comprising a pharmaceutically acceptable carrier and the compound or salt of claim 1.

10. An anticancer agent, comprising a pharmaceutically acceptable carrier and an active ingredient comprising the compound or salt of claim 1.

11. A STAT3 inhibitor, comprising a pharmaceutically acceptable carrier and an active ingredient comprising the compound or salt of claim 1.

12. A method of treating cancer in which STAT3 is activated, the method comprising:
administering an effective amount of the anticancer agent of claim 10 to a patient in need thereof.

13. A method for manufacturing an anticancer agent, the method comprising:
mixing the compound or salt of claim 1 with a pharmaceutically acceptable carrier.

14. A method of treating cancer in which STAT3 is activated, the method comprising:
administering an effective amount of the compound or salt of claim 1 to a patient in need thereof.

15. A medicine, comprising a pharmaceutically acceptable carrier and the compound or salt of claim 8.

16. An anticancer agent, comprising a pharmaceutically acceptable carrier and an active ingredient comprising the compound or salt of claim 8.

17. A STAT3 inhibitor, comprising a pharmaceutically acceptable carrier and an active ingredient comprising the compound or salt of claim 8.

18. A method of treating cancer in which STAT3 is activated, the method comprising:
administering an effective amount of the anticancer agent of claim 16 to a patient in need thereof.

19. A method for manufacturing an anticancer agent, the method comprising:
mixing the compound or salt of claim 8 with a pharmaceutically acceptable carrier.

20. A method of treating cancer in which STAT3 is activated, the method comprising:
administering an effective amount of the compound or salt of claim 8 to a patient in need thereof.

* * * * *

UNITED STATES PATENT AND TRADEMARK OFFICE
CERTIFICATE OF CORRECTION

PATENT NO. : 8,796,320 B2  Page 1 of 1
APPLICATION NO. : 13/519707
DATED : August 5, 2014
INVENTOR(S) : Asai et al.

It is certified that error appears in the above-identified patent and that said Letters Patent is hereby corrected as shown below:

In the Claims

Column 94, Line 13, Claim 5 should read:

--xiii) $SiR^{33}R^{34}R^{35}$, wherein $R^{33}$, $R^{34}$, and $R^{35}$ are the same or--

Column 94, Line 16, Claim 5 should read:

--xv) a cyano groups,--

Column 96, Lines 18-19, Claim 8 should read:

--4'-cyano-N-[5-(2-furyl)-1,3,4-oxadiazol-2-yl]-2'-methyl-3-biphenylcarboxamide (Compound Ia-29);--

Signed and Sealed this
Twenty-fifth Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO.      : 8,796,320 B2
APPLICATION NO. : 13/519707
DATED           : August 5, 2014
INVENTOR(S)     : Akira Asai et al.

It is certified that error appears in the above-identified patent and that said Letters Patent is hereby corrected as shown below:

On the title page, Item (73), the Assignees' Information is incorrect. Item (73) should read:

--(73) Assignees: General Incorporated Association Pharma Valley Project Supporting Organization, Mishima-shi (JP); Pharma Design, Inc., Tokyo (JP); Shizuoka Prefecture, Shizuoka-city (JP); Kumamoto Health Science University, Kumamoto-shi (JP); Kabushiki Kaisha Yakult Honsha, Tokyo (JP)--

Signed and Sealed this
Twentieth Day of January, 2015

Michelle K. Lee
*Deputy Director of the United States Patent and Trademark Office*